United States Patent
Lee et al.

(10) Patent No.: US 9,873,722 B2
(45) Date of Patent: *Jan. 23, 2018

(54) WNT COMPOSITIONS AND THERAPEUTIC USES OF SUCH COMPOSITIONS

(75) Inventors: Tom Tong Lee, San Diego, CA (US); Michael J. Fitch, Carlsbad, CA (US); Kevin Lai, San Diego, CA (US); Peter Flynn, San Diego, CA (US); Monica Bennett, San Diego, CA (US)

(73) Assignee: Fate Therapeutics, Inc., San Diego, CA (US)

(*) Notice: Subject to any disclaimer, the term of this patent is extended or adjusted under 35 U.S.C. 154(b) by 453 days.

This patent is subject to a terminal disclaimer.

(21) Appl. No.: 14/344,310

(22) PCT Filed: Sep. 14, 2012

(86) PCT No.: PCT/US2012/055336
§ 371 (c)(1),
(2), (4) Date: Dec. 19, 2014

(87) PCT Pub. No.: WO2013/040309
PCT Pub. Date: Mar. 21, 2013

(65) Prior Publication Data
US 2015/0099708 A1    Apr. 9, 2015

Related U.S. Application Data

(60) Provisional application No. 61/535,913, filed on Sep. 16, 2011.

(51) Int. Cl.
*C07K 14/47*   (2006.01)
*C07K 14/475*  (2006.01)
*A61K 38/00*   (2006.01)

(52) U.S. Cl.
CPC ............ *C07K 14/47* (2013.01); *C07K 14/475* (2013.01); *A61K 38/00* (2013.01); *C07K 2319/02* (2013.01); *C07K 2319/20* (2013.01); *C07K 2319/21* (2013.01); *C07K 2319/30* (2013.01); *C07K 2319/40* (2013.01); *C07K 2319/41* (2013.01); *C07K 2319/42* (2013.01); *C07K 2319/43* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,544,752 A | 10/1985 | Beck et al. |
| 4,751,180 A | 6/1988 | Cousens et al. |
| 4,935,233 A | 6/1990 | Bell et al. |
| 5,679,647 A | 10/1997 | Carson et al. |
| 5,739,118 A | 4/1998 | Carrano et al. |
| 5,837,533 A | 11/1998 | Boutin |
| 6,297,030 B1 | 10/2001 | Barnes et al. |
| 6,337,184 B1 | 1/2002 | Miller |
| 6,590,075 B2* | 7/2003 | Ruben ............ C07K 14/47 435/6.14 |
| 7,153,832 B2 | 12/2006 | Nusse et al. |
| 7,335,643 B2 | 2/2008 | Nusse et al. |
| 7,541,183 B2 | 6/2009 | Rudnicki et al. |
| 9,403,885 B2 | 8/2016 | Lee et al. |
| 2004/0005579 A1* | 1/2004 | Birse ............... C07K 14/47 435/6.14 |
| 2005/0130181 A1 | 6/2005 | McSwiggen |
| 2006/0171931 A1 | 8/2006 | Rudnicki et al. |
| 2008/0226707 A1 | 9/2008 | Helms et al. |
| 2008/0299135 A1 | 12/2008 | Zou |
| 2009/0074777 A1 | 3/2009 | Wands et al. |
| 2011/0319337 A1 | 12/2011 | Bravo et al. |
| 2012/0213744 A1 | 8/2012 | Rudnicki et al. |
| 2014/0142046 A1 | 5/2014 | Lee et al. |
| 2014/0200179 A1* | 7/2014 | Garcia ............. G01N 33/566 514/7.6 |
| 2015/0111822 A1 | 4/2015 | Rudnicki et al. |

FOREIGN PATENT DOCUMENTS

| | | |
|---|---|---|
| JP | 2010-520286 A | 6/2010 |
| JP | 2014-506568 A | 3/2014 |
| WO | WO 92/06180 A1 | 4/1992 |
| WO | WO 92/22635 A1 | 12/1992 |
| WO | WO 93/14188 A1 | 7/1993 |
| WO | WO 93/20221 A1 | 10/1993 |
| WO | WO 2004/029229 A2 | 4/2004 |
| WO | WO 2004/113513 A2 | 12/2004 |
| WO | WO 2006/026652 A2 | 3/2006 |

(Continued)

OTHER PUBLICATIONS

Alland, L. et al. "Dual myristylation and palmitylation of Src family member p59fyn affects subcellular localization", Journal of Biological Chemistry, 269:16701-16705 (1994).

Altschul et al., "Gapped BLAST and PSI-BLAST: a new generation of protein database search programs", Nucleic Acids Research, 25(17): 3389-402 (1997).

Amerongen, "Alternative Wnt Pathways and Receptors", Cold Spring Harbor Perspectives in Biology, 4(10): a007914, 18 pages (2012).

Anakwe et al., "Wnt signalling regulates myogenic differentiation in the developing avian wing", Development, 130(15): 3503-3514 (2003).

Anastas, et al., "WNT signalling pathways as therapeutic targets in cancer," Nature Reviews Cancer, 13(1):11-26 (2012).

Asakura et al., "Myogenic specification of side population cells in skeletal muscle", The Journal of Cell Biology, 159(1):123-134 (2002).

Bae et al., "Regulation of myoblast motility and fusion by the CXCR4-associated sialomucin, CD164," J Biol Chem, 283(13):8301-8309 (2008).

(Continued)

Primary Examiner — Daniel C Gamett
(74) Attorney, Agent, or Firm — Jones Day

(57) ABSTRACT

The invention provides novel Wnt polypeptides that have improved production characteristics, solubility, systemic delivery, and tissue uptake, and polynucleotides encoding the Wnt polypeptides of the invention. The Wnt polypeptides of the invention can be used therapeutically, such as, for example, in methods of preventing or treating muscle loss and/or promoting muscle hypertrophy and growth.

12 Claims, 32 Drawing Sheets

(56) References Cited

FOREIGN PATENT DOCUMENTS

| WO | WO 2006/072016 A2 | 7/2006 |
|---|---|---|
| WO | WO 2007/059612 A1 | 5/2007 |
| WO | WO 2008/109119 A2 | 9/2008 |
| WO | WO 2010/014948 A1 | 2/2010 |
| WO | WO 2010/124365 A1 | 4/2010 |
| WO | WO 2010/078458 A1 | 7/2010 |
| WO | WO 2011/088127 A1 | 7/2011 |
| WO | WO 2012/097093 A2 | 7/2012 |
| WO | WO 2012/103360 A2 | 8/2012 |
| WO | WO 2013/040309 A2 | 3/2013 |
| WO | WO 2013/040341 A2 | 3/2013 |

OTHER PUBLICATIONS

Bass et al., "Syndecan-4-dependent Rac1 regulation determines directional migration in response to the extracellular matrix", The Journal of Cell Biology, 177(3): 527-538 (2007).
Bazan, et al., "Structural architecture and functional evolution of Wnts," Dev Cell., 23(2): 227-232 (2012).
Bentzinger et al., "Extrinsic regulation of satellite cell specification", Stem Cell Res Ther, 1(3): 27 (2010).
Bhanot, et al., "A new member of the frizzled family from *Drosophila* functions as a Wingless receptor," Nature, 382(6588):225-230 (1996).
Bird et al., "Single-chain antigen-binding proteins", Science, 242: 423-426 (1988).
Bodine et al., "Akt/mTOR pathway is a crucial regulator of skeletal muscle hypertrophy and can prevent muscle atrophy in vivo", Nature Cell Biology, 3: 1014-1019 (2001).
Bönnemann, "Beyond dystrophin: current progress in the muscular dystrophies", C. G. et al., Curr. Opin. Ped., 8(6): 569-582 (1996).
Bosnakovski et al., "Prospective isolation of skeletal muscle stem cells with a Pax7 reporter", Stem Cells, 26(12): 3194-3204 (2008). Epub Sep. 18, 2008.
Borello et al., "The Wnt/β-catenin pathway regulates Gli-mediated Myf5 expression during somitogenesis", Development, 133: 3723-3732 (2006).
Brack et al., "A Temporal Switch from Notch to Wnt Signaling in Muscle Stem Cells Is Necessary for Normal Adult Myogenesis", Cell Stem Cell, 2: 50-59 (2008).
Bradley, et al., "A soluble form of Wnt-1 protein with mitogenic activity on mammary epithelial cells," Mol Cell Biol, 15(8):4616-4622 (1995).
Brown, R.H., Jr., "Dystrophin-associated proteins and the muscular dystrophies", Annu. Rev. Med., 48: 457-466 (1997).
Burrus et al., "Biochemical analysis of murine Wnt proteins reveals both shared and distinct properties", Exp Cell Res., 220(2): 363-373 (1995).
Cerletti et al., "Highly efficient, functional engraftment of skeletal muscle stem cells in dystrophic muscles," Cell, 134:37-47 (2008).
Chargé and Rudnicki, "Cellular and molecular regulation of muscle regeneration", Physiol Rev., 84(1): 209-238 (2004).
Charge et al., "Aging-related satellite cell differentiation defect occurs prematurely after Ski-induced muscle hypertrophy," Am J Physiol Cell Physiol, 283:C1228-1241 (2002).
Chaudhary et al., "A rapid method of cloning functional variable-region antibody genes in *Escherichia coli* as single-chain immunotoxins", Proc. Natl. Acad. Sci. U.S.A., 87: 1066-1070 (1990).
Chen et al., "Protein kinase A signalling via CREB controls myogenesis induced by Wnt proteins", Nature, 433: 317-322 (2005).
Ching et al. "Lipid-independent Secretion of a *Drosophila* Wnt Protein", Journal of Biological Chemistry, 283(25): 17092-17098 (2008).
Ciciliot and Schiaffino, "Regeneration of mammalian skeletal muscle. Basic mechanisms and clinical implications", Current Pharmaceutical Design,16(8): 906-914 (2010).
Ciruna et al., "Planar cell polarity signalling couples cell division and morphogenesis during neurulation," Nature 439:220-224. 2006.
Clevers, "Wnt/β-Catenin Signaling in Development and Disease," Cell 127:469-480 (2006).
Collins et al., "Stem Cell Function, Self-Renewal, and Behavioral Heterogeneity of Cells from the Adult Muscle Satellite Cell Niche," Cell 122, 289-301 (2005).
Cooper, "Advances in membrane receptor screening and analysis," Journal of Molecular Recognition, 17(4):286-315 (2004).
Cornelison et al., "Essential and separable roles for Syndecan-3 and Syndecan-4 in skeletal muscle development and regeneration," Genes & Development,18:2231-2236, 2004.
Cornelison et al., "Syndecan-3 and Syndecan-4 Specifically Mark Skeletal Muscle Satellite Cells and are Implicated in Satellite Cell Maintenance and Muscle Regeneration," Dev Biol, 239:79-94 (2001).
Cosgrove et al., "A home away from home: challenges and opportunities in engineering in vitro muscle satellite cell niches", Differentiation, 78(2-3): 185-194 (2009).
Cossu et al., "Wnt signaling and the activation of myogenesis in mammals," Embo J ,18, 6867-6872, 1999.
Couso, et al., "Notch is Required for wingless Signaling in the Epidermis of *Drosophila*," Cell, 79(2): 259-272 (1994).
Crise et al., "Identification of palmitoylation sites on CDR, the Human Immunodeficiency Virus receptor", Journal of Biological Chemistry 267: 13593-13597 (1992).
Daley et al., "Identification of a mechanochemical checkpoint and negative feedback loop regulating branching morphogenesis", Developmental Biology, 336(2):169-182 (2009). Epub Oct. 3, 2009.
Daley et al., "A focal adhesion protein-based mechanochemical checkpoint regulates cleft progression during branching morphogenesis", Dev Dyn., 240(9): 2069-2083 (2011).
Dann et al., "Insights into Wnt binding and signalling from the structures of two Frizzled cysteine-rich domains," Nature, 412:86-90, 2001.
Database EMBL [Online] "Rattus norvegicus (Norway rat) rCG56255", Aug. 9, 2005 (Sep. 8, 2005), NPL reference No. XP002734433: obtained on NCBI, NCBI Accession No. EDL91364.
De Vos et al., "Human growth hormone and extracellular domain of its receptor: crystal structure of the complex", Science, 255:306-312 (1992).
Del Alamo and Miodzik, "Frizzled/PCP-Dependent Asymmetric Neuralized Expression Determines R3/R4 Fates in the *Drosophilia* Eye," Developmental Cell, 11:887-894 (2006).
Diatchenko et al., "Suppression subtractive hybridization: a method for generating differentially regulated or tissue-specific cDNA probes and libraries," Proc Natl Acad Sci U S A, 93:6025-6030 (1997).
Dierick and Bejsovec, "Cellular Mechanisms of Wingless/Wnt Signal Transduction", Current Topics in Developmental Biology, 43: 153-178 (1999).
Doubravska et al. "Fatty acid modification of Wnt1 and Wnt3a at serine is prerequisite for lipidation at cysteine and is essential for Wnt signalling", Cellular Signalling, 23(5): 837-848 (2011).
Egger-Adam et al., "Trimeric G protein-dependent signaling by Frizzled receptors in animal development," Front Biosci, 13:4740-4755 (2008).
EMBL Accession No. EDL91364, Aug. 9, 2005, XP-002934433, 1 page.
European Application No. 10769170.1, (Corrected) European Search Report dated May 27, 2013.
European Application No. 10769170.1, European Search Report dated Apr. 24, 2013.
European Application No. 12734079.2, Extended European Search Report dated Apr. 2, 2015.
European Application No. 12734079.2, Partial European Search Report Dec. 4, 2014.
European Application No. 12738949.2, Extended European Search Report dated Jul. 4, 2014.
European Application No. 12831452.3, Extended European Search Report dated Dec. 23, 2014.

(56) References Cited

OTHER PUBLICATIONS

European Application No. 12831715.3, Extended European Search Report dated Feb. 9, 2015.
Fisher and Upadhyaya, "Molecular genetics of facioscapulohumeral muscular dystrophy (FSHD)", Neuromuscular Disorders, 7(1): 55-62 (1997).
Franch-Marro et al., "Wingless secretion requires endosome-to-Golgi retrieval of Wntless/Evi/Sprinter by the retromer complex", Nature Cell Biology, 10(2): 170-177 (2008). Published online: Jan. 13, 2008.
Fredriksson et al., "Protein detection using proximity-dependent DNA ligation assays", Nature Biotechnology, 20: 473-477 (2002).
Funakoshi et al., "Emerin and cardiomyopathy in Emery-Dreifuss muscular dystrophy", Neuromuscular Disorders, 9(2): 108-114 (1999).
Galli and Burrus, "Differential Palmit(e)oylation of Wnt1 on C93 and S224 Residues Has Overlapping and Distinct Consequences", PLoS One, 6(10): e26636, pp. 1-17 (2011).
GenBank Accession No. G36470, "Wnt-7a protein—mouse". Downloaded Apr. 30, 2013. http://www.ncbi.nlm.nih.gov/protein/G36470?report=genpept.
GenBank Accession No. H36470, "Wnt-7b protein—mouse". Downloaded Apr. 30, 2013. http://www.ncbi.nlm.nih.gov/protein/H36470?report=genpept.
GenBank Accession No. M89801, "Mouse Wnt-7a mRNA, complete cds." Downloaded Apr. 30, 2013. http://www.ncbi.nlm.nih.gov/nuccore/M89801.
GenBank Accession No. NM_004625, "*Homo sapiens* wingless-type MMTV integration site family, member 7A (WNT7A), mRNA." Downloaded Apr. 30, 2013. http://www.ncbi.nlm.nih.gov/nuccore/NM_004625.
GenBank Accession No. NP_004616, "protein Wnt-7a precursor [*Homo sapiens*]." Downloaded Apr. 30, 2013. http://www.ncbi.nlm.nih.gov/protein/NP_004616.
GenBank Accession No. 000755, RecName: Full=Protein Wnt-7a; Flags: Precursor. Downloaded Apr. 30, 2013. http://www.ncbi.nlm.nih.gov/protein/O00755.
GenBank Accession No. P24383, RecName: Full=Protein Wnt-7a; Flags: Precursor. Downloaded Apr. 30, 2013. http://www.ncbi.nlm.nih.gov/protein/P24383.
GenBank Accession No. P28047, RecName: Full=Protein Wnt-7b; Flags: Precursor. Downloaded Apr. 30, 2013. http://www.ncbi.nlm.nih.gov/protein/P28047.
GenBank Accession No. PF6706, Uncultured bacterium clone PF6706 16S ribosomal RNA gene, partial sequence. Downloaded Apr. 30, 2013. http://www.ncbi.nlm.nih.gov/nuccore/290611196.
Giles, et al., "Caught up in a Wnt storm: Wnt signaling in cancer," Biochim Biophys Acta, 1653(1):1-24 (2003).
Glass et al., "Signalling pathways that mediate skeletal muscle hypertrophy and atrophy", Nature Cell Biology, 5: 87-90 (2003).
Goto et al., "Planar Cell Polarity Genes Regulate Polarized Extracellular Matrix Deposition During Frog Gastrulation," Curr Biol, 15:787-793 (2005).
Green et al., "Opposing Wnt pathways orient cell polarity during organogenesis," Nature, 134:646-656 (2008).
Gros et al., "WNT11 acts as a directional cue to organize the elongation of early muscle fibres", Nature, 457: 589-593 (2009).
Hall et al., "Axonal Remodeling and Synaptic Differentiation in the Cerebellum Is Regulated by WNT-7a Signaling," Cell, 100:525-535 (2000).
Hayman and Ruoslahti, "Distribution of fetal bovine serum fibronectin and endogenous rat cell fibronectin in extracellular matrix", The Journal of Cell Biology, 83(1): 255-259 (1979).
Henikoff and Henikoff, "Amino acid substitution matrices from protein blocks", Proc Natl Acad Sci U S A., 89(22): 10915-10919 (1992).
Hirabayashi et al., "The Wnt/β-catenin pathway directs neuronal differentiation of cortical neural precursor cells," Development 131:2791-2801, 2004.

Hoffman et al., "Characterization of dystrophin in muscle-biopsy specimens from patients with Duchenne's or Becker's muscular dystrophy", N. Engl. J. Med., 318(21): 1363-1368 (1988).
Hoppler, et al., "Expression of a dominant-negative Wnt blocks induction of MyoD in Xenopus embryos," Genes & Development, 10(21):2805-2817 (1996).
Hruby, "Designing peptide receptor agonists and antagonists," Nature Reviews Drug Discovery, 1(11):847-858 (2002).
Hsieh, et al., "Biochemical characterization of Wnt-Frizzled interactions using a soluble, biologically active vertebrate Wnt protein," Proceedings of the National Academy of Sciences, 96(7):3546-3551 (1999).
Huang et al., "Interference of tenascin-C with syndecan-4 binding to fibronectin blocks cell adhesion and stimulates tumor cell proliferation", Cancer Research, 61(23): 8586-8594 (2001).
Huston et al., "Protein engineering of antibody binding sites: recovery of specific activity in an anti-digoxin single-chain Fv analogue produced in *Escherichia coli*", Proc. Natl. Acad. Sci. U.S.A., 85: 5879-5883 (1988).
Hynes and Yamada, "Fibronectins: Multifunctional Modular Glycoproteins", The Journal of Cell Biology, 95: 369-377 (1982).
Ingham, "Has the quest for a Wnt receptor finally frizzled out?," Trends Genet., 12(10)382-384 (1996).
Ishibashi et al, "MyoD induces myogenic differentiation through cooperation of its NH2- and COOH-terminal regions," J Cell Biol, 171, 471-482 (2005).
Ishikawa et al., Seibutsugaku Jiten [Biology Dictionary], first print, Tokyo Kagaku Dojin K.K., (2010); Housekeeping gene (plants) (genes); A gene encoding a protein required for general functions of a cell, which is constitutively expressed (constitutive gene). (Japanese dictionary reference with English summary of relevant portion.).
Janda, et al., "Structural basis of Wnt Recognition by Frizzled," Science, 337(6090):59-64, (2012).
Kadowaki et al., "The segment polarity gene porcupine encodes a putative multitransmembrane protein involved in Wingless processing", Genes Development, 10: 3116-3128 (1996).
Kengaku et al., "Distinct WNT Pathways Regulating AER Formation and Dorsoventral Polarity in the Chick Limb Bud," Science 280:1274-1277, 1998.
Kikuchi, et al., "Multiplicity of the interactions of Wnt proteins and their receptors," Cell Signal, 19(4):659-671 (2007).
Klaus, et al., "Wnt signalling and its impact on development and cancer," Nature Reviews Cancer, 8(5):387-398 (2008).
Koller and Smithies, "Inactivating the $β_2$-microglobulin locus in mouse embryonic stem cells by homologous recombination", Proc. Natl. Acad. Sci. USA, 86: 8932-8935 (1989).
Komekado, H. et al. "Glycosylation and palmitoylation of Wnt-3a are coupled to produce an active form of Wnt-3a", Genes to Cells, 12(4): 521-534 (2007).
Kuang et al., "Asymmetric self-renewal and commitment of satellite stem cells in muscle," Cell, 129(5):999-1010 (2007).
Kuang et al., "Distinct roles for Pax7 and Pax3 in adult regenerative myogenesis," J Cell Biol,172:103-113 (2006).
Kuang et al., Niche Regulation of Muscle Satellite Cell Self-Renewal and Differentiation, Cell Stem Cell, 2: 22-31 (2008).
Kurayoshi et al. "Post-translational palmitoylation and glycosylation of Wnt-5a are necessary for its signalling", Biochem J., 402(3): 515-523 (2007).
Le Grand et al., "Wnt7a activates the planar cell polarity pathway to drive the symmetric expansion of satellite stem cells", Cell Stem Cell, 4: 535-547 (2009).
Lim et al. "Direct Binding of Syndecan-4 Cytoplasmic Domain to the Catalytic Domain of Protein Kinase C (PKCα) Increases Focal Adhesion Localization of PKCα", The Journal of Biological Chemistry, 278(16): 13795-13802 (2003).
Lim and Campbell, "The sarcoglycan complex in limb-girdle muscular dystrophy," Curr. Opin. Neurol., 11(5):443-452, 1998.
Logan, et al., "The Wnt Signaling Pathway in Development and Disease," (2004) Annu Rev Cell Dev Biol 20:781-810 (2004).
Lyon et al., "Elucidation of the structural features of heparan sulfate important for interaction with the Hep-2 domain of fibronectin", The Journal of Biological Chemistry, 275(7): 4599-4606 (2000).

(56) References Cited

OTHER PUBLICATIONS

Lyu and Joo, "Wnt-7a Up-regulates Matrix Metalloproteinase-12 Expression and Promotes Cell Prliferation in Corneal Epithelial Cells during Sound Healing," The Journal of Biological Chemistry, 280(22):21653-21660, 2005.
Maltzahn et al., "A truncated Wnt7a retains full biological activity in skeletal muscle", Nature Communications, 4: 2869, 9 pages (2013).
Maratea et al., "Deletion and fusion analysis of the phage phi X174 lysis gene E", Gene, 40: 39-46 (1985).
Massie et al., "New adenovirus vectors for protein production and gene transfer", Cytotechnology, 28(1-3): 53-64 (1998).
Mason et al., "Mutational analysis of mouse Wnt-1 identifies two temperature-sensitive alleles and attributes of Wnt-1 protein essential for transformation of a mammary cell line", Mol. Biol. Cell, 3: 521-533 (1992).
Matthews et al., "Directional migration of neural crest cells in vivo is regulated by Syndecan-4/Rac1 and non-canonical Wnt signaling/RhoA," Development, 135:1771-1780 (2008).
McKinnell et al., "Pax7 activates myogenic genes by recruitment of a histone methyltransferase complex," Nat Cell Biol,,10:77-84, 2008.
McMahon, "The Wnt family of developmental regulators," Trends Genet., 8(7):236-242 (1992).
Miller, "The Wnts," Genome Biol., 3(1)reviews3001.1-3001.15 (2001).
Miller and Sassoon, "Wnt-7a maintains appropriate uterine patterning during the development of the mouse female reproductive tract," Development, 125:3201-3211 (1998).
Montarras et al., "Direct Isolation of Satellite Cells for Skeletal Muscle Regeneration," Science, 309:2064-2067 (2005).
Montcouquiol et al., "Asymmetric localization of Vangl2 and Fz3 indicate novel mechanisms for planar cell polarity in mammals," J Neurosci, 26:5265-5275 (2006).
Montcouquiol et al., "Identification of Vangl2 and Scrb1 as planar polarity genes in mammals," Nature, 423:173-177 (2003).
Morrell, et al., "Liposomal Packaging Generates Wnt Protein with In Vivo Biological Activity," PLoS One, 3(8):e2930 (2008).
Munoz et al., "Syndecan-4 regulates non-canonical Wnt signalling and is essential for convergent and extension movements in Xenopus embryos," Nat Cell Biol, 8:492-500 (2006).
Murakami et al., "Non-canonical fibroblast growth factor signalling in angiogenesis", Cardiovascular Research, 78: 223-231 (2008).
Murphy et al., "Genetic construction, expression, and melanoma-selective cytotoxicity of a diphtheria toxin-related alpha-melanocyte-stimulating hormone fusion protein", Proc. Natl. Acad. Sci. USA, 83: 8258-8262 (1986).
Nagaoka et al., "Cripto-1 enhances the canonical Wnt/β-catenin signaling pathway by binding to LRP5 and LRP6 co-receptors", Cell Signal, 25(1): 178-189 (2013). Published online Sep. 27, 2012. doi: 10.1016/j.cellsig.2012.09.024.
Nusse, "Wnt signaling in disease and in development," Cell Research, 15(1):28-32 (2005).
Nusse, et al., "Many Tumors Induced by the Mouse Mammary Tumor Virus Contain a Provirus Integrated in the Same Region of the Host Genome," Cell, 31(1):99-109 (1982).
Nusse, R., "Wnts and Hedgehogs: lipid-modified proteins and similarities in signaling mechanisms at the cell surface", Development, 130: 5297-5305 (2003).
O'Dowd et al., "Palmitoylation of the human beta 2 adrenergic receptor" Journal of Biological Chemistry 269: 7564-7569 (1989).
Oustanina et al., "Pax7 directs postnatal renewal and propagation of myogenic satellite cells but not their specification," The EMBO Journal, 23:3430-3439, 2004.
Papkoff, et al., "Wnt-1 Regulates Free Pools of Catenins and Stabilizes APC-Catenin Complexes," Mol. Cell Biol., 16(5):2128-2134 (1996).
Park and Moon, "The planar cell-polarity gene stbm regulates cell behaviour and cell fate in vertebrate embryos," Nat Cell Biol, 4:20-25, 2002.

PCT Application No. International PCT/CA2010/000601, International Search Report mailed Jul. 22, 2010, 7 pages.
PCT Application No. PCT/CA2010/000601, Written Opinion mailed Jul. 22, 2010, 9 pages.
PCT Application No. PCT/CA2010/000601, International Preliminary Report on Patentability mailed Nov. 1, 2011, 10 pages.
PCT Application No. PCT/US2012/020984, International Search Report and Written Opinion, mailed Jul. 30, 2012, 14 pages.
PCT Application No. PCT/US2012/020984, International Preliminary Report on Patentability, dated Jul. 16, 2013, 7 pages.
PCT Application No. PCT/US2012/022761, International Search Report and Written Opinion dated Aug. 10, 2012, 10 pages.
PCT Application No. PCT/US2012/022761, International Preliminary Report on Patentability dated Aug. 10, 2012, 6 pages.
PCT Application No. PCT/US2012/055336, International Search Report and Written Opinion dated Feb. 25, 2013, 11 pages.
PCT Application No. PCT/US2012/055336, International Reliminary Report on Patentability dated Mar. 18, 2014, 7 pages.
PCT Application No. PCT/US2012/055396, International Search Report and Written Opinion dated Feb. 26, 2013, 14 pages.
PCT Application No. PCT/US2012/055396, International Reliminary Report on Patentability dated Feb. 26, 2013, 14 pages.
Peifer et al., "wingless signal and Zeste-white 3 kinase trigger opposing changes in the intracellular distribution of Armadillo," Development, 120(2):369-380 (1994).
Peters et al., "Fibronectin isoform distribution in the mouse. II. Differential distribution of the alternatively spliced EIIIB, EIIIA, and V segments in the adult mouse", Cell Adhesion and Communication, 4(2):127-48 (1996).
Pisconti et al., "Syndecan-3 and Notch cooperate in regulating adult myogenesis", J Cell Biol., 190(3): 427-441 (2010).
Polesskaya et al, "Wnt signaling induces the myogenic specification of resident CD45+ adult stem cells during muscle regeneration", Cell, 113(7): 841-52 (2003).
Resh, M.A. "Fatty acylation of proteins: new insights into membrane targeting of myristoylated and palmitoylated proteins" Biochimica et Biophysica Acta 1451:1-16 (1999).
Rochat et al., "Insulin and Wnt1 Pathways Cooperate to Induce Reserve Cell Activation in Differentiation and Myotube Hypertrophy", Molecular Biology of the Cell, 15: 4544-4555 (2004).
Sacco et al., "Self-renewal and expansion of single transplanted muscle stem cells," Nature, 56:502-506 (2008).
Seale et al., "Pax7 Is Required for the Specification of Myogenic Satellite Cells," Cell, 102(6):777-786 (2000).
Seifert et al., "Frizzled/PCP signalling: a conserved mechanism regulating cell polarity and directed motility," Nat Rev Genet, 8(2):126-138 (2007).
Singh et al., "Assembly of fibronectin extracellular matrix", Annual Review of Cell and Developmental Biology, 26: 397-419 (2010).
Smith et al., "Human interleukin 4. The solution structure of a four-helix bundle protein", J. Mol. Biol., 224: 899-904 (1992).
Smolich et al., "Wnt family proteins are secreted and associated with the cell surface", Molecular Biology of the Cell, 4(12): 1267-1275 (1993).
Srinivas et al., "Cre reporter strains produced by targeted insertion of EYFP and ECFP into the ROSA26 locus," BMC Dev Biol, 1:4 (2001).
Struewing, et al., "Mitochondrial and Nuclear Forms of Wnt13 Are Generated via Alternative Promoters, Alternative RNA Splicing, and Alternative Translation Start Sites," Journal of Biological Chemistry, 281(11):7282-7293 (2006).
Tajbakhsh et al., "Differential activation of Myf5 and MyoD by different Wnts in explants of mouse paraxial mesoderm and the later activation of myogenesis in the absence of Myf5", Development, 125: 4155-4162 (1998).
Takada et al. "Monounsaturated Fatty Acid Modification of Wnt Protein: Its Role in Wnt Secretion", Developmental Cell, 11(6): 791-801 (2006).
Tallquist et al., "Early myotome specification regulates PDGFA expression and axial skeleton development," Development 127:5059-5070 (2000).

(56) References Cited

OTHER PUBLICATIONS

Tanaka et al. "*Drosophila* segment polarity gene product porcupine stimulates the posttranslational N-glycosylation of wingless in the endoplasmic reticulum", J. Biol. Chem., 277: 12816-12823 (2002).
Torban et al., "Genetic interaction between members of the Vangl family causes neural tube defects in mice," Proc Natl Acad Sci U S A,105:3449-3454 (2008).
Torban et al., "Van Gogh-like2 (Strabismus) and its role in planar cell polarity and convergent extension in vertebrates," Trends Genet, 20(11):570-577 (2004).
Torrente et al., "Human circulating AC133+stem cells restore dystrophin expression and ameliorate function in dystrophic skeletal muscle", The Journal of Clinical Investigation, 114(2): 182-195 (2004).
U.S. Appl. No. 13/266,428, Advisory Action mailed Dec. 5, 2014.
U.S. Appl. No. 13/266,428, Office Action mailed Jun. 30, 2014.
U.S. Appl. No. 13/266,428, Office Action mailed Jun. 9, 2015.
U.S. Appl. No. 13/266,428, Office Action mailed Nov. 12, 2015.
U.S. Appl. No. 13/266,428, Office Action mailed Oct. 15, 2013.
U.S. Appl. No. 13/266,428, Office Action mailed Apr. 19, 2016.
U.S. Appl. No. 13/979,368, Office Action mailed Oct. 6, 2015.
U.S. Appl. No. 13/982,184, Office Action mailed Jun. 11, 2015.
U.S. Appl. No. 13/982,184, Office Action mailed Jan. 4, 2016.
U.S. Appl. No. 14/344,309, Office Action mailed Mar. 17, 2016.
Uhlman and Peyman, "Antisense Oligonucleotides: A New Therapeutic Principle", Chemical Reviews, 90(4): 544-584 (1990).
Van Den Heuvel et al., "Mutations in the segment polarity genes wingless and porcupine impair secretion of the wingless protein", 12(13): 5293-5302 (1993).
Van Leeuwen, et al., "Biological activity of soluble wingless protein in cultured *Drosophila* imaginal disc cells," Nature, 368(6469):342-344 (1994).
Veeman, et al., "A Second Canon: Functions and Mechanisms of Beta-Catenin-Independent Wnt Signaling," Dev. Cell 5(3):367-377 (2003).
Voit, T., "Congenital muscular dystrophies: 1997 update", Brain Development, 20(2): 65-74 (1998).

Von Maltzahn et al, "Wnt7a-Fzd7 signalling directly activates the Akt/mTOR anabolic growth pathway in skeletal muscle", Nature Cell Biology, 14(2): 186-191 (2012).
Wang, et al., "Wnt7b Activates Canonical Signaling in Epithelial and Vascular Smooth Muscle Cells through Interactions with Fzd1, Fzd10, and LRP5," Mol Cell Biol., 25(12): 5022-5030 (2005).
Willert et al., "Wnt Proteins are lipid-modified and can act as stem cell growth factors", Nature, 423(6938): 448-452 (2003).
Wodarz and Nusse, "Mechanisms of Wnt signaling in development", Annu. Rev. Cell. Dev. Biol., 14: 59-88 (1998).
Worton, R., "Muscular dystrophies: diseases of the dystrophin-glycoprotein complex", Science, 270: 755-756 (1995).
Woods et al., "Syndecan-4 binding to the high affinity heparin-binding domain of fibronectin drives focal adhesion formation in fibroblasts", Archives of Biochemistry and Biophysics, 374(1):66-72 (2000).
Xian et al. "Syndecans as receptors and organizers of the extracellular matrix", Cell and Tissue Research, 339(1): 31-46 (2010).
Yamanaka et al., "Wnt11 stimulation induces polarized accumulation of dishevelled at apical adherens junctions through Frizzled 7," Genes to Cells Devoted to Molecular & Cellular Mechanisms, 12:961-967 (2007).
Yang-Snyder, et al., "A frizzled homolog functions in a vertebrate Wnt signaling pathway," Curr Biol., 6(10):1302-1306 (1996).
Zallen, "Planar Polarity and Tissue Morphogenesis," Cell, 129(6): 1051-1063 (2007).
Zhai et al., "*Drosophila* Wnt-1 Undergoes a Hydrophobic Modification and Is Targeted to Lipid Rafts, a Process That Requires Porcupine", The Journal of Biological Chemistry, 279(32): 33220-33227 (2004).
Zhao, et al., "Controlling the In Vivo Activity of Wnt Liposomes," Methods Enzymol, 465:331-347 (2009).
Zijlstra et al., "Germ-line transmission of a disrupted $\beta_2$-microglobulin gene produced by homologous recombination in embryonic stem cells", Nature, 342: 435-438 (1989).
Zusinaite et al., "Mutations at the palmitoylation site of non-structural protein nsP1 of Semliki Forest virus attenuate virus replication and cause accumulation of compensatory mutations" Journal of General Virology 88: 1977-1985 (2007).

\* cited by examiner

| WNT7A | Fusion | Expression mg/L |
|---|---|---|
| Wild-type | | 0.9 |
| Wild-type | Fc | 4.6 |
| C73, S206A | | 1.7 |
| C73, S206A | Fc | 11.9 |
| C73A, S206A | | 1.4 |
| C73A, S206A | Fc | 12.0 |
| aa264-349 | Fc | 10.8 |

*FIG. 4*

| N (WT Mice) | Contralateral | Formulation | IGF-1 | wtWnt7a |
|---|---|---|---|---|
| | 7 | 6 | 6 | 5 |
| Median | 36.03 | 35.91 | 39.93 | 38.28 |
| 25% Percentile | 33.35 | 31.69 | 38.14 | 37.07 |
| 75% Percentile | 38.09 | 38.36 | 40.35 | 41.43 |
| Mean | 35.74 ± 2.09 | 34.65 ± 4.98 | 39.44 ± 1.23 | 39.05 ± 2.32 |
| P value* | 0.9974 | 0.6151 | 0.0007 | 0.0332 |
| Hypertrophy (%)* | 100 | N/A | 110.4 | 109.3 |

*FIG. 13D*

| | FC-Control | 264-349-FC (+Chaps) | 264-349-FC (-Chaps) |
|---|---|---|---|
| N (MDX Mice) | 4 | 4 | 4 |
| Mean | 33.28 ± 3.96 | 36.16 ± 3.15 | 38.13 ± 2.11 |
| P Value * | 0.9996 | 0.1648 | 0.0193 |
| N (Diameter values) | 4004 | 4004 | 4004 |
| 25% Percentile | 18.52 | 23.94 | 25.31 |
| Median | 30.93 | 33.94 | 35.35 |
| 75% Percentile | 43.83 | 45.37 | 48.59 |

FIG. 14C

WNT COMPOSITIONS AND THERAPEUTIC USES OF SUCH COMPOSITIONS

CROSS-REFERENCE TO RELATED APPLICATIONS

This application claims the benefit under 35 U.S.C. § 119(e) of U.S. Provisional Application No. 61/535,913, filed Sep. 16, 2011, which is herein incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FATE 109 01US ST25.txt. The text file is 77 KB, was created On Dec. 19, 2014, and is being submitted electronically via EFS-Web.

BACKGROUND

Technical Field

The invention relates generally to Wnt compositions and therapeutic methods of using the same. The Wnt polypeptides of the invention and compositions thereof may be used therapeutically, for example for promoting muscle regeneration by promoting stem cell expansion and muscle hypertrophy.

Description of the Related Art

The Wnt family of genes encodes over twenty cysteine-rich, secreted Wnt glycoproteins that act by binding to Frizzled (Fzd) receptors on target cells. Frizzled receptors are a family of G protein coupled receptor proteins. Binding of different members of the Wnt-family to certain members of the Fzd family can initiate signaling by one of several distinct pathways. In the "canonical pathway," activation of the signaling molecule, Disheveled, leads to the inactivation of glycogen synthase kinase-3 (GSK3β), a cytoplasmic serine-threonine kinase. The GSK-3β target, β-catenin, is thereby stabilized and translocates to the nucleus where it activates TCF (T-cell-factor)-dependant transcription of specific promoters (Wodarz, 1998, Dierick, 1999). "Non-canonical" Wnt pathway activation is less well-defined, but includes a subset of interactions between Wnt and Fzd that may activate $Ca^{2+}$ pathway signaling and potentially PI3K signaling, Rho pathway signaling, and planar cell polarity (PCP) pathway signaling.

Wnts are secreted glycoproteins that function as paracrine or autocrine signals active in several primitive cell types. Although Wnt proteins are secreted from cells, they are found to be hydrophobic and are believed to be post-translationally modified by addition of a lipid moiety at a conserved cysteine residue and a conserved serine residue. These lipid modifications are widely accepted to be important for the biological activity and secretion of Wnt proteins. Lipidation and the low solubility of lipidated Wnts, however, are associated with low production yields when detergents are not used during formulation and thus, present a unique challenge for clinical scale production of Wnt. Thus, while Wnts have a tremendous potential for use as therapeutics in a variety of clinical settings, the therapeutic potential of Wnts has yet to be fully realized due to Wnt insolubility and corresponding insufficient production as a purified, biologically active therapeutic.

Accordingly, the art is in need of soluble, Wnt polypeptides that retain Wnt biological activity, methods for generating the Wnts on a clinical scale, and methods of using the Wnts to promote tissue formation, regeneration, maintenance and repair.

BRIEF SUMMARY

The invention generally provides novel Wnt compositions and therapeutic methods for promoting muscle regeneration by promoting stem cell expansion and muscle hypertrophy.

In one embodiment, the present invention contemplates, in part, an isolated Wnt polypeptide comprising an N-terminal deletion, wherein the N-terminal deletion removes one or more lipidation sites.

In a particular embodiment, the N-terminal deletion comprises a deletion of 300 N-terminal amino acids.

In another particular embodiment, the N-terminal deletion comprises a deletion of 250 N-terminal amino acids.

In an additional particular embodiment, the N-terminal deletion comprises a deletion of 200 N-terminal amino acids.

In a further particular embodiment, the N-terminal deletion comprises a deletion of 150 N-terminal amino acids.

In one embodiment, the N-terminal deletion removes a single lipidation site.

In another embodiment, the N-terminal deletion removes at least two lipidation sites.

In yet another embodiment, the N-terminal deletion removes all lipidation sites.

In a related embodiment, the isolated Wnt polypeptide further comprises a C-terminal deletion of one or more C-terminal amino acids.

In another related embodiment, the isolated Wnt polypeptide further comprises a C-terminal deletion of at least 10 C-terminal amino acids.

In yet another related embodiment, the isolated Wnt polypeptide further comprises a C-terminal deletion of at least 20 C-terminal amino acids.

In still yet another related embodiment, the isolated Wnt polypeptide further comprises a C-terminal deletion of at least 50 C-terminal amino acids.

In a particular embodiment, the isolated Wnt polypeptide comprises a biologically active Wnt polypeptide.

In a certain particular embodiment, the isolated Wnt polypeptide retains non-canonical Wnt signaling activity.

In a related particular embodiment, the isolated Wnt polypeptide has improved production yield compared to a naturally occurring Wnt polypeptide.

In a further particular embodiment, the isolated Wnt polypeptide has improved secretory properties compared to a naturally occurring Wnt polypeptide.

In an additional particular embodiment, the Wnt polypeptide has improved stability or half-life compared to a naturally occurring Wnt polypeptide.

In various embodiments, the present invention provides, in part, a Wnt fusion polypeptide comprising an isolated Wnt polypeptide according to any one of the embodiments disclosed herein.

In one embodiment, the Wnt fusion polypeptide comprises an Fc-domain.

In another embodiment, the Wnt fusion polypeptide does not have antibody-dependent cell-mediated cytotoxicity (ADCC) or complement-dependent cytotoxicity (CDC) activity.

In one particular embodiment, the Wnt fusion polypeptide has improved production yield compared to a naturally occurring Wnt polypeptide.

In a certain embodiment, the Wnt fusion polypeptide has improved secretory properties compared to a naturally occurring Wnt polypeptide.

In a certain particular embodiment, the Wnt fusion polypeptide has improved stability or half-life compared to a naturally occurring Wnt polypeptide.

In a certain additional embodiment, the Wnt fusion polypeptide comprises a native signal peptide, a heterologous signal peptide, or a hybrid of a native and a heterologous signal peptide.

In a further certain embodiment, the Wnt fusion polypeptide comprises a heterologous signal peptide is selected from the group consisting of: a CD33 signal peptide, an immunoglobulin signal peptide, a growth hormone signal peptide, an erythropoietin signal peptide, an albumin signal peptide, a secreted alkaline phosphatase signal peptide, and a viral signal peptide.

In another embodiment, the heterologous signal peptide is a CD33 signal peptide, an IgGK signal peptide, or an IgGµ signal peptide.

In another related embodiment, the Wnt fusion polypeptide comprises a heterologous protease cleavage site.

In a particular related embodiment, the heterologous protease cleavage site is selected from the group consisting of: a tobacco etch virus (TEV) protease cleavage site, a heparin cleavage site, a thrombin cleavage site, an enterokinase cleavage site and a Factor Xa cleavage site.

In one embodiment, the Wnt fusion polypeptide comprises an epitope tag selected from the group consisting of: a HIS6 epitope, a MYC epitope, a FLAG epitope, a V5 epitope, a VSV-G epitope, and an HA epitope.

In various embodiments, the present invention contemplates, in part, a composition comprising a Wnt polypeptide according to any one of the embodiments disclosed herein or a Wnt fusion polypeptide according to any one of the embodiments disclosed herein.

In particular embodiments, the composition comprises a pharmaceutically-acceptable salt, carrier, or excipient.

In a certain embodiment, the excipient increases the half-life of the Wnt polypeptide or Wnt fusion polypeptide of the composition.

In a further embodiment, the excipient increases the stability of the Wnt polypeptide or Wnt fusion polypeptide of the composition.

In one embodiment, the present invention contemplates, in part, an isolated Wnt7a polypeptide comprising: an amino acid sequence at least 80% identical to the amino acid sequence set forth in SEQ ID NO: 2, and further comprising an N-terminal deletion of at least 220 amino acids of the amino acid sequence set forth in SEQ ID NO: 2; an amino acid sequence at least 80% identical to the amino acid sequence set forth in SEQ ID NO: 3; an amino acid sequence at least 85% identical to the amino acid sequence set forth in SEQ ID NO: 4; an amino acid sequence at least 80% identical to the amino acid sequence set forth in SEQ ID NO: 5; or an amino acid sequence comprising at least 70 contiguous amino acids identical to the amino acid sequence set forth in any one of SEQ ID NOs: 3-5.

In a particular embodiment, an isolated Wnt7a polypeptide comprises: an amino acid sequence at least 95% identical to the amino acid sequence set forth in SEQ ID NO: 2, and further comprising an N-terminal deletion of at least 220 amino acids of the amino acid sequence set forth in SEQ ID NO: 2; an amino acid sequence at least 95% identical to the amino acid sequence set forth in SEQ ID NO: 3; an amino acid sequence at least 95% identical to the amino acid sequence set forth in SEQ ID NO: 4; an amino acid sequence at least 95% identical to the amino acid sequence set forth in SEQ ID NO: 5; or an amino acid sequence comprising at least 70 contiguous amino acids identical to the amino acid sequence set forth in any one of SEQ ID NOs: 3-5.

In a certain embodiment, an isolated Wnt7a polypeptide comprises: an amino acid sequence that can be optimally aligned with the sequence of SEQ ID NO: 3 to generate a similarity score of at least 220, using the BLOSUM62 matrix, a gap existence penalty of 11, and a gap extension penalty of 1; an amino acid sequence that can be optimally aligned with the sequence of SEQ ID NO: 3 to generate an e-value score of at least e-74, using the BLOSUM62 matrix, a gap existence penalty of 11, and a gap extension penalty of 1; an amino acid sequence that can be optimally aligned with the sequence of SEQ ID NO: 4 to generate a similarity score of at least 210, using the BLOSUM62 matrix, a gap existence penalty of 11, and a gap extension penalty of 1; an amino acid sequence that can be optimally aligned with the sequence of SEQ ID NO: 4 to generate an e-value score of at least e-66, using the BLOSUM62 matrix, a gap existence penalty of 11, and a gap extension penalty of 1; an amino acid sequence that can be optimally aligned with the sequence of SEQ ID NO: 5 to generate a similarity score of at least 170, using the BLOSUM62 matrix, a gap existence penalty of 11, and a gap extension penalty of 1; or an amino acid sequence that can be optimally aligned with the sequence of SEQ ID NO: 5 to generate an e-value score of at least e-52, using the BLOSUM62 matrix, a gap existence penalty of 11, and a gap extension penalty of 1.

In particular embodiments, the isolated Wnt7a polypeptide further comprises a C-terminal deletion of one or more C-terminal amino acids.

In certain embodiments, the isolated Wnt7a polypeptide further comprises a C-terminal deletion of at least 10 C-terminal amino acids.

In additional embodiments, the isolated Wnt7a polypeptide further comprises a C-terminal deletion of at least 20 C-terminal amino acids.

In further embodiments, the isolated Wnt7a polypeptide comprises a biologically active Wnt7a polypeptide or retains Wnt7a biological activity.

In one embodiment, an isolated Wnt7a polypeptide according to any one of the embodiments disclosed herein, retains non-canonical Wnt7a signaling activity.

In a particular embodiment, an isolated Wnt7a polypeptide according to any one of the embodiments disclosed herein, has improved production yield compared to a naturally occurring Wnt7a polypeptide.

In a certain embodiment, an isolated Wnt7a polypeptide according to any one of the embodiments disclosed herein, has improved secretory properties compared to a naturally occurring Wnt7a polypeptide.

In a further embodiment, an isolated Wnt7a polypeptide according to any one of the embodiments disclosed herein, has improved stability or half-life compared to a naturally occurring Wnt7a polypeptide.

In one embodiment, the isolated Wnt7a polypeptide comprises the amino acid sequence set forth in any one of SEQ ID NOs: 3-5.

In a particular embodiment, the isolated Wnt7a polypeptide comprises at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, or 129 contiguous amino acids of the amino acid sequence set forth in SEQ ID NO: 3.

In a certain embodiment, the isolated Wnt7a polypeptide has increased solubility in an aqueous solution compared to a Wnt polypeptide having the amino acid sequence set forth in any one of SEQ ID NOs: 2 and 18-23.

In a certain particular embodiment, the isolated Wnt7a polypeptide binds a Frizzled receptor on the surface of a cell.

In a further particular embodiment, the cell is a skeletal muscle satellite stem cell.

In an additional embodiment, the binding of the isolated Wnt7a polypeptide to the Frizzled receptor increases satellite stem cell expansion compared to the satellite stem cell expansion in the absence of the isolated Wnt7a polypeptide.

In a further embodiment, a Wnt7a fusion polypeptide comprises the isolated Wnt7a polypeptide according to any one of the embodiments disclosed herein.

In one embodiment, a Wnt7a fusion polypeptide according to any one of the embodiments disclosed herein, comprises an Fc-domain.

In another embodiment, a Wnt7a fusion polypeptide does not have ADCC or CDC activity.

In a certain embodiment, a Wnt7a fusion polypeptide has improved production yield compared to a naturally occurring Wnt7a polypeptide.

In a particular embodiment, a Wnt7a fusion polypeptide has improved secretory properties compared to a naturally occurring Wnt7a polypeptide.

In an additional embodiment, a Wnt7a fusion polypeptide has improved stability or half-life compared to a naturally occurring Wnt7a polypeptide.

In some embodiments, the Wnt7a fusion polypeptide comprises a native signal peptide, a heterologous signal peptide, or a hybrid of a native and a heterologous signal peptide.

In one embodiment, the Wnt7a fusion polypeptide comprises a heterologous signal peptide selected from the group consisting of: a CD33 signal peptide, an immunoglobulin signal peptide, a growth hormone signal peptide, an erythropoietin signal peptide, an albumin signal peptide, a secreted alkaline phosphatase signal peptide, and a viral signal peptide.

In a particular embodiment, the heterologous signal peptide is a CD33 signal peptide, an IgGI(signal peptide, or an IgGµ signal peptide.

In an additional embodiment, the Wnt7a fusion polypeptide comprises a heterologous protease cleavage site.

In an additional particular embodiment, the Wnt7a fusion polypeptide comprises a heterologous protease cleavage site selected from the group consisting of: a tobacco etch virus (TEV) protease cleavage site, a heparin cleavage site, a thrombin cleavage site, an enterokinase cleavage site and a Factor Xa cleavage site.

In an additional certain embodiment, the Wnt7a fusion polypeptide comprises an epitope tag selected from the group consisting of: a HIS6 epitope, a MYC epitope, a FLAG epitope, a V5 epitope, a VSV-G epitope, and an HA epitope.

In a further embodiment, the present invention provides a polynucleotide encoding a Wnt7a polypeptide or a Wnt7a fusion polypeptide according to any one of the embodiments disclosed herein.

In a certain embodiment, the present invention provides a vector comprising the polynucleotide encoding a Wnt7a polypeptide or a Wnt7a fusion polypeptide according to any one of the embodiments disclosed herein.

In a certain particular embodiment, the present invention provides host cell comprising a vector that comprises the polynucleotide encoding a Wnt7a polypeptide or a Wnt7a fusion polypeptide according to any one of the embodiments disclosed herein.

In a further embodiment, the host cell is a mammalian cell, an insect cell, or a bacterial cell.

In another embodiment, a Wnt7a polypeptide or Wnt7a fusion polypeptide according to any one of the embodiments disclosed herein is produced by the host cell.

In one embodiment, the present invention contemplates, in part, a composition comprising a Wnt7a polypeptide according to any one of the embodiments disclosed herein or a Wnt7a fusion polypeptide according to any one of the embodiments disclosed herein; a polynucleotide encoding a Wnt7a polypeptide according to any one of the embodiments disclosed herein or a Wnt7a fusion polypeptide according to any one of the embodiments disclosed herein; or a vector comprising a polynucleotide encoding a Wnt7a polypeptide according to any one of the embodiments disclosed herein or a Wnt7a fusion polypeptide according to any one of the embodiments disclosed herein.

In a particular embodiment, the composition comprises a pharmaceutically-acceptable salt, carrier, or excipient.

In a certain embodiment, the composition is soluble in an aqueous solution.

In a further embodiment, the composition is formulated for injection.

In an additional embodiment, the composition is formulated for one or more of intravenous injection, intracardiac injection, subcutaneous injection, intraperitoneal injection, or direct injection into a muscle.

In various embodiments, the composition promotes tissue formation, regeneration, maintenance or repair.

In particular embodiments, the tissue is muscle.

In related embodiments, the muscle is skeletal, cardiac, or smooth muscle.

In a particular embodiment, the composition promotes stem cell expansion.

In an additional embodiment, the stem cell is an adult stem cell.

In a certain embodiment, the adult stem cell is a satellite stem cell.

In a certain additional embodiment, the composition promotes muscle hypertrophy or prevents muscle atrophy.

In one embodiment, the present invention contemplates, in part, a method for treating or preventing muscle loss comprising administering to a subject: a truncated Wnt polypeptide according to any one of the embodiments disclosed herein, a vector comprising a polynucleotide that encodes a truncated Wnt polypeptide according to any one of the embodiments disclosed herein, or a composition according to any one of the embodiments disclosed herein.

In one embodiment, the excipient increases the half-life of the Wnt7a polypeptide or Wnt7a fusion polypeptide of the composition.

In another embodiment, the excipient increases the stability of the Wnt7a polypeptide or Wnt7a fusion polypeptide of the composition. In a particular embodiment, the composition is soluble in an aqueous solution.

In a further embodiment, the composition is formulated for injection.

In one embodiment, the composition is formulated for one or more of intravenous injection, intracardiac injection, subcutaneous injection, intraperitoneal injection, or direct injection into muscle.

In an additional embodiment, the subject has or is at risk of having a disease or condition affecting muscle.

In a particular embodiment, the disease is a degenerative disease.

In another particular embodiment, the degenerative disease is muscular dystrophy.

In a certain particular embodiment, the muscular dystrophy is selected from Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

In a further particular embodiment, the disease or condition affecting muscle is a wasting disease, muscular attenuation, muscle atrophy, ICU-induced weakness, prolonged disuse, surgery-induced weakness, or a muscle degenerative disease.

In an additional particular embodiment, the condition is muscle atrophy associated with muscle disuse, immobilization, surgery-induced weakness, or injury.

In a further embodiment, administering the composition prevents muscle atrophy.

In a certain embodiment, administering the composition promotes muscle hypertrophy.

In a particular embodiment, the muscle is skeletal muscle or cardiac muscle.

In one embodiment, administering the composition promotes satellite stem cell expansion.

BRIEF DESCRIPTION OF THE SEVERAL VIEWS OF THE DRAWINGS

Figure 1:
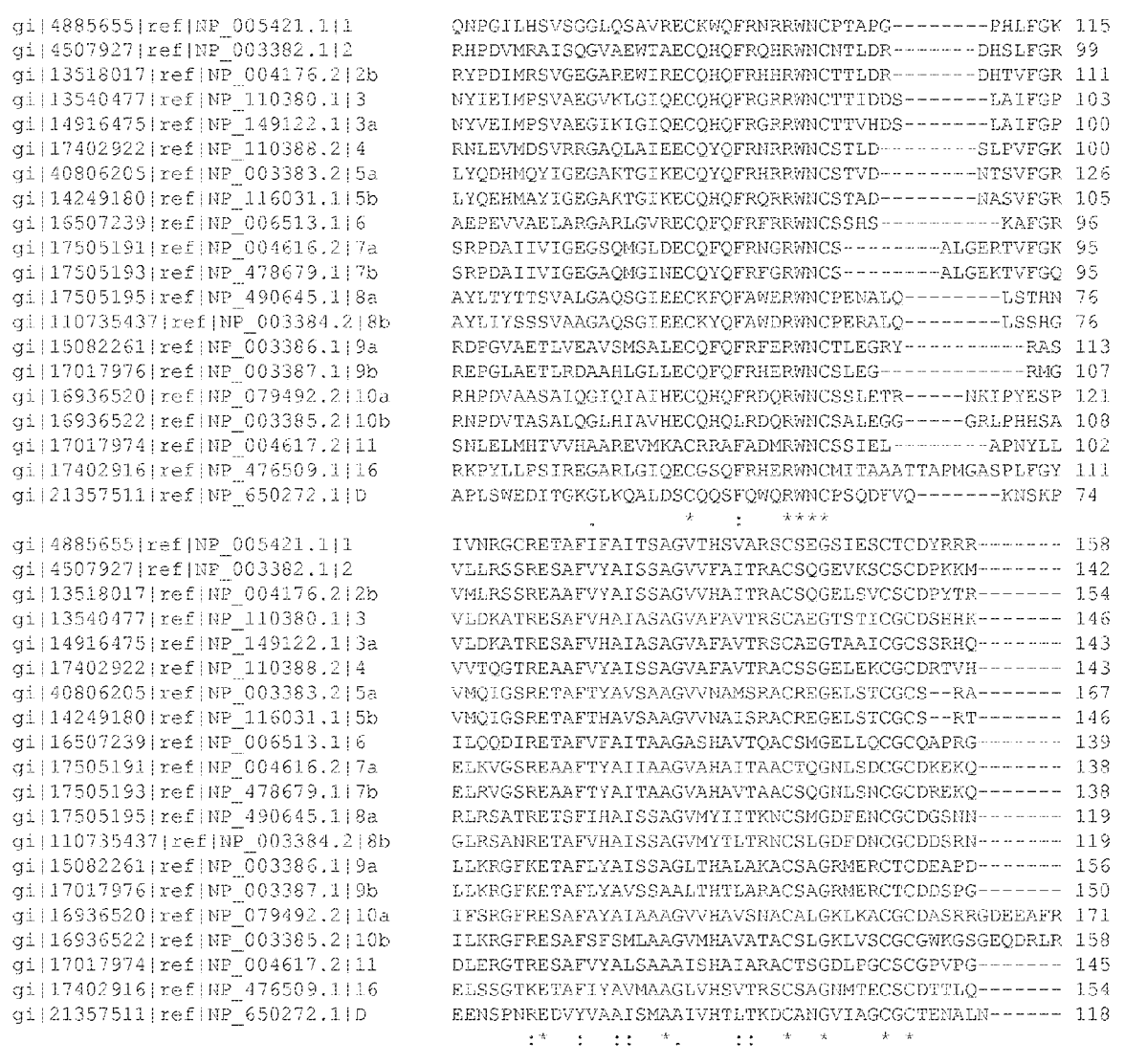
Figure 1:
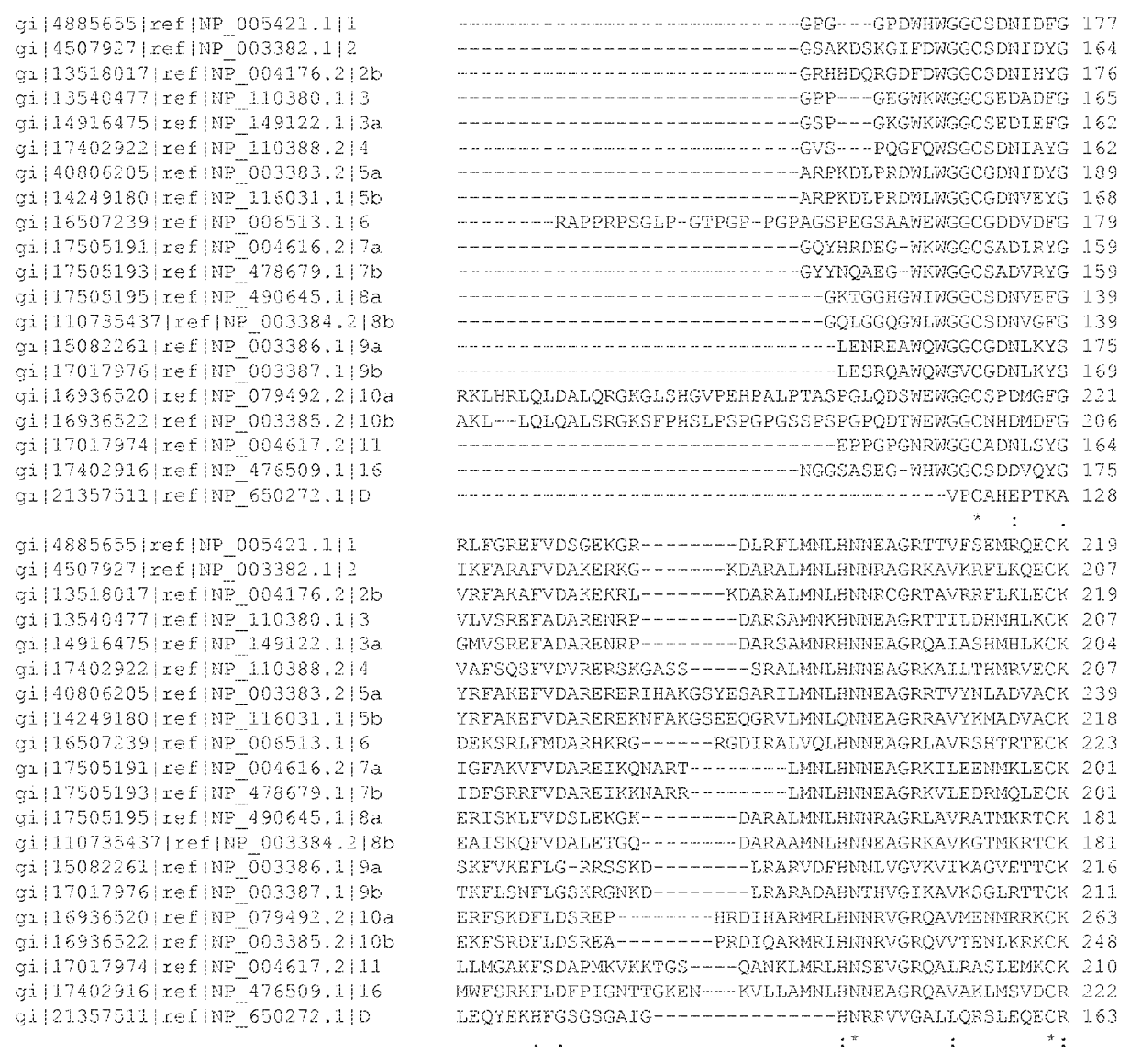
Figure 1:
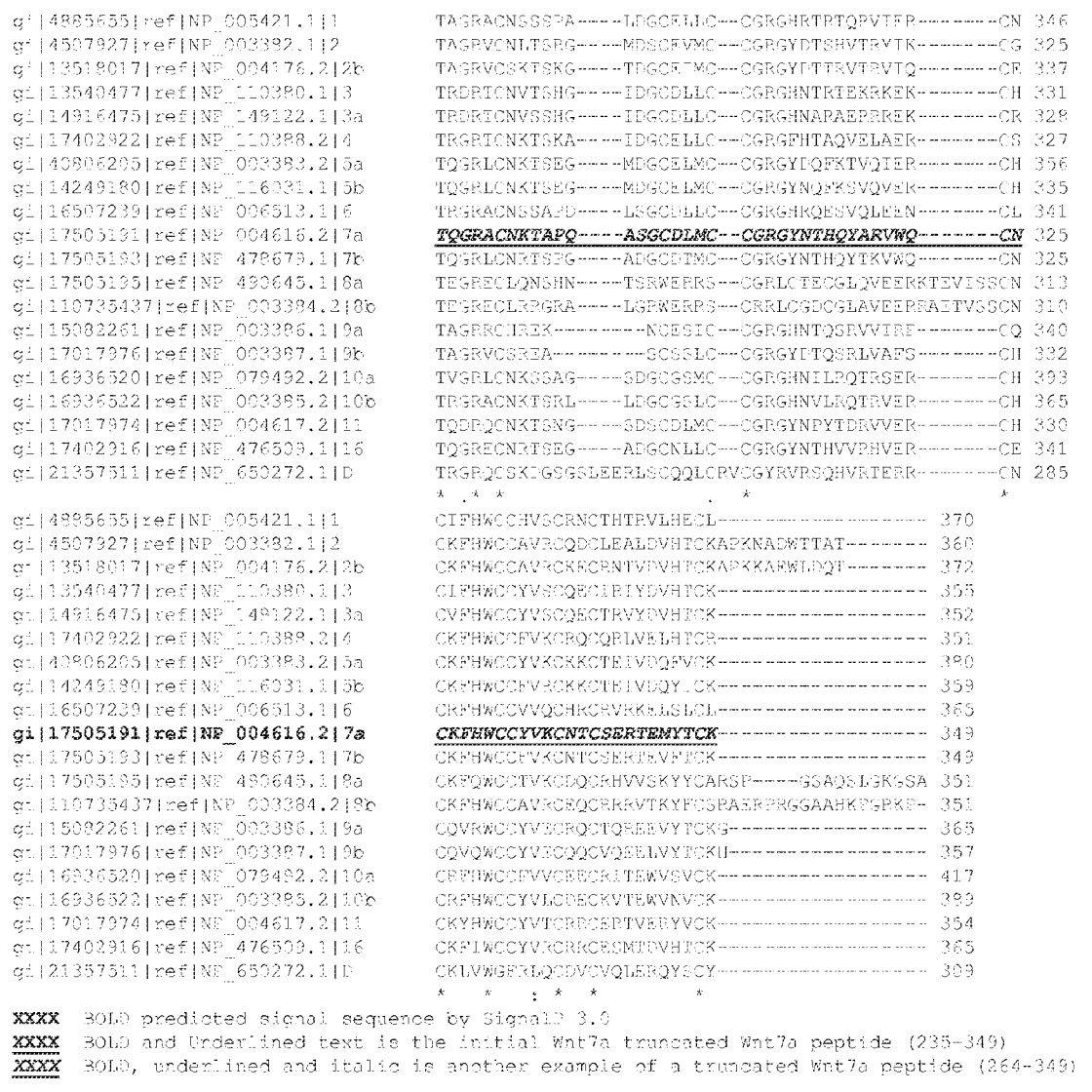

FIG. 1 shows a multiple alignment of human Wnt polypeptides and the *Drosophila* polypeptide WntD.

FIG. 2 shows the secondary structure predictions for Wnt7a and Wnt3a. A) Amino acid sequence of wild-type human Wnt7a is displayed with numbering (10X). ProteinPredict secondary structure prediction software results are shown (Prof sec) with H=Alpha Helix, E=Sheet and L=Loop or blank where no definitive structure could be determined. Relative confidence score for each prediction is displayed (Rel Sec) and regions with above 85% confidence are listed (SUB sec). B) Amino acid sequence of wild-type human Wnt3a is displayed with numbering (10×). ProteinPredict secondary structure prediction software results are shown (Prof sec) with H=Alpha Helix, E=Sheet and L=Loop or blank where no definitive structure could be determined. Relative confidence score for each prediction is displayed (Rel Sec) and regions with above 85% confidence are listed (SUB sec).

FIG. 4 shows expression yields of various Wnt7a protein forms. Wnt7a protein forms were expressed as described in Example 4. The Wnt protein modification and the yield of Wnt protein per liter of mammalian cell culture media is shown.

FIG. 6 shows that Wnt7a induces myofiber hypertrophy in vitro. C2C 12 mouse myoblasts were differentiated into myofibers and treated with Wnt7a protein as described in Example 5. Formulation control (Phosphate buffered Saline supplemented with 1% CHAPS) was compared to wt Wnt7a.

BRIEF DESCRIPTION OF THE SEQUENCE IDENTIFIERS

Figure 3:
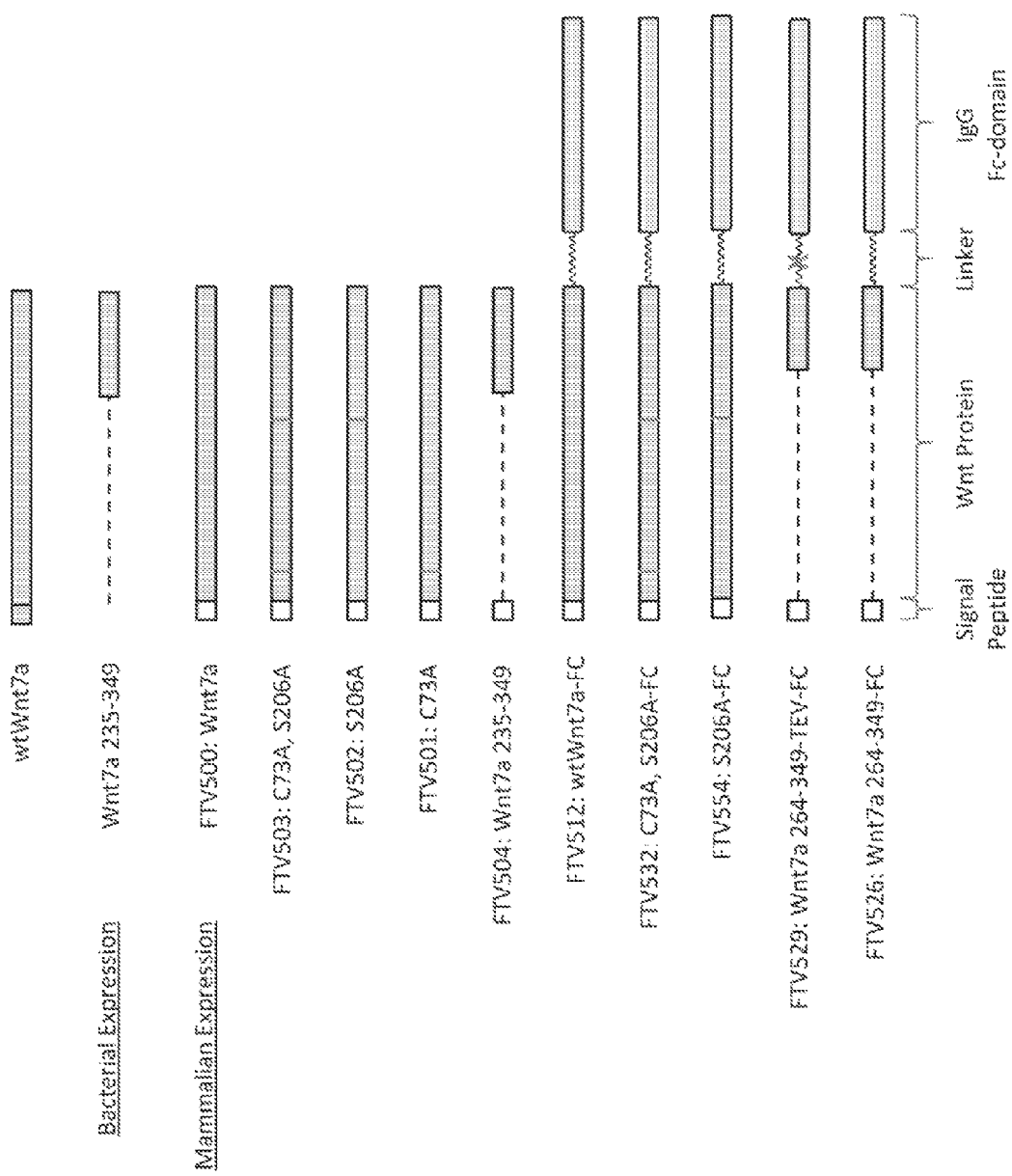
FIG. 3 shows the construction of Wnt proteins with preferred pharmaceutical properties. A schematic representation of Wnt7a proteins designed and constructed as described in Example 1. Signal peptides are highlighted as exogenous in all but the wild-type protein (wtWnt7a). Point mutations designed to result in delipidated protein forms are described in text and highlighted in the schematic. Truncations and FC-Fusions are as shown.

SEQ ID NO: 1 sets forth a cDNA sequence of human Wnt7a.

SEQ ID NO: 2 sets forth the amino acid sequence of the human Wnt7a polypeptide encoded by SEQ ID NO: 1.

SEQ ID NO: 3 sets forth amino acids 221-349 of SEQ ID NO: 2.

SEQ ID NO: 4 sets forth amino acids 235-349 of SEQ ID NO: 2.

SEQ ID NO: 5 sets forth amino acids 264-349 of SEQ ID NO: 2.

SEQ ID NOs: 6-9 set forth the amino acid sequences of fusion polypeptides comprising the amino acid sequence of SEQ ID NO: 3.

SEQ ID NOs: 10-13 set forth the amino acid sequences of fusion polypeptides comprising the amino acid sequence of SEQ ID NO: 4.

SEQ ID NOs: 14-17 set forth the amino acid sequences of fusion polypeptides comprising the amino acid sequence of SEQ ID NO: 5.

SEQ ID NO: 18 sets forth the amino acid sequence of a mouse Wnt7a polypeptide.

SEQ ID NO: 19 sets forth the amino acid sequence of a rat Wnt7a polypeptide.

SEQ ID NO: 20 sets forth the amino acid sequence of a chicken Wnt7a polypeptide.

SEQ ID NO: 21 sets forth the amino acid sequence of a zebrafish Wnt7a polypeptide.

SEQ ID NO: 22 sets forth the amino acid sequence of a porcine Wnt7a polypeptide.

SEQ ID NO: 23 sets forth the amino acid sequence of a bovine Wnt7a polypeptide.

SEQ ID NOs: 24-26 set forth polynucleotide sequences used to construct Wnt expression vectors.

SEQ ID NO: 27 sets forth the polynucleotide sequence that encodes a CD33 signal peptide.

SEQ ID NO: 28 sets forth the amino acid sequence encoded by the polynucleotide sequence of SEQ ID NO: 27.

SEQ ID NO: 29 sets forth the polynucleotide sequence that encodes a IgGI(signal peptide.

SEQ ID NO: 30 sets forth the amino acid sequence encoded by the polynucleotide sequence of SEQ ID NO: 29.

SEQ ID NOs: 31-32 set forth the amino acid sequences of fusion polypeptides comprising the amino acid sequence of SEQ ID NO: 3.

SEQ ID NOs: 33-34 set forth the amino acid sequences of fusion polypeptides comprising the amino acid sequence of SEQ ID NO: 4.

SEQ ID NOs: 35-36 set forth the amino acid sequences of fusion polypeptides comprising the amino acid sequence of SEQ ID NO: 5.

SEQ ID NOs: 37-38 set forth the amino acid sequences of fusion polypeptides comprising the amino acid sequence of SEQ ID NO: 4.

SEQ ID NOs: 39-40 set forth the amino acid sequences of fusion polypeptides comprising the amino acid sequence of SEQ ID NO: 5.

SEQ ID NOs: 41-42 set forth the amino acid sequences of fusion polypeptides comprising the amino acid sequence of SEQ ID NO: 4.

SEQ ID NOs: 43-44 set forth the amino acid sequences of fusion polypeptides comprising the amino acid sequence of SEQ ID NO: 5.

DETAILED DESCRIPTION

A. Overview

While post-translational lipidation of Wnts is believed to be required for biological activity and protein secretion, the invention provides, in part, novel truncated Wnt polypeptides having Wnt biological activity including truncated forms of Wnt lacking one or more lipidation sites. The polypeptides of the invention retain Wnt biological activity, and the invention thus provides modified Wnt polypeptides and compositions comprising the same that have improved biologic drug-like properties such as enhanced solubility, production, formulation, systemic delivery, and tissue uptake, and therapeutic uses for such Wnt polypeptides. The invention further provides a novel solution to the problem posed by the insolubility of Wnt polypeptides and further, provides inventive Wnt polypeptides that are suitable for clinical scale production and therapeutic use. Therapeutic uses for the Wnt polypeptides of the invention include, for example, promoting stem cell expansion, tissue formation, and cell and/or tissue regeneration, repair or maintenance.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent.

As used herein, the term "adult stem cell" or "somatic stem cell" refers to a stem cell found in a developed or developing organism; often in a specific tissue of an organism. Adult stem cells can divide by cell division, are either multipotent or unipotent and subsequently differentiate to increase, replace or regenerate lost cells and/or tissues. Adult stem cells include, but are not limited to, ectodermal stem cells, endodermal stem cells, mesodermal stem cells, neural stem cells, hematopoietic stem cells, muscle stem cells, satellite stem cells, and the like. A muscle stem cell is an example of stem cell that is traditionally thought to be unipotent, giving rise to muscle cells only.

As used herein, the term "satellite stem cell" refers to a type of adult stem cell that gives rise to cells of the myogenic lineage, e.g., myoblasts and myocytes. In one embodiment, the satellite stem cell is a $Pax7^+/Myf5^-$ muscle stem cell. In a particular embodiment, the satellite stem cell is a skeletal muscle stem cell.

As used herein, the term "progenitor cell" refers to a cell that has the capacity to self-renew and to differentiate into more mature cells, but is committed to a lineage (e.g., hematopoietic progenitors are committed to the blood lineage), whereas stem cells are not necessarily so limited. A myoblast is an example of a progenitor cell, which is capable of differentiation to only one type of cell, but is itself not fully mature or fully differentiated. A myoblast may differentiate into a myocyte.

As used herein, the term "myocyte" or "myofiber" refers to a differentiated type of cell found in muscles. Each myocyte contains myofibrils, which are long chains of sarcomeres, the contractile units of the muscle cell. There are various specialized forms of myocytes: cardiac, skeletal, and smooth muscle cells, with various properties known in the art.

As used herein, the term "self-renewal" refers to a cell with a unique capacity to produce unaltered daughter cells and to generate specialized cell types (potency). Self-renewal can be achieved in at least two ways. Asymmetric cell division produces one daughter cell that is identical to the parental cell and one daughter cell that is different from the parental cell and is a progenitor or differentiated cell.

Asymmetric cell division thus does not increase the number of daughter cells identical to the parental cell, but maintains the number of cells of the parental cell type. Symmetric cell division, in contrast, produces two daughter cells that are each identical to the parental cell. Symmetric cell division thus increases the number of cells identical to the parental cell, expanding the population of parental cells. In particular embodiments, symmetric cell division is used interchangeably with cell expansion, e.g., expansion of the stem cell population As used herein, the term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. States of undifferentiation or differentiation may be assessed, for example, by assessing or monitoring the presence or absence of biomarkers using immunohistochemistry or other procedures known to a person skilled in the art.

As used herein, the term "lineage commitment" refers to the process by which a stem cell becomes committed to forming a particular limited range of differentiated cell types. Lineage commitment arises, for example, when a stem cell gives rise to a progenitor cell during asymmetric cell division. Committed progenitor cells are often capable of self-renewal or cell division.

As used herein, the term "terminal differentiation" refers to the final differentiation of a cell into a mature, fully differentiated cell. Usually, terminal differentiation is associated with withdrawal from the cell cycle and cessation of proliferation.

As used herein, the term "muscle hypertrophy" refers to an increase in muscle size, and may include an increase in individual fiber volume and/or an increase in the cross-sectional area of myofibers, and may also include an increase in the number of nuclei per muscle fiber. Muscle hypertrophy may also include an increase in the volume and mass of whole muscles; however, muscle hypertrophy can be differentiated from muscle hyperplasia, which is the formation of new muscle cells. In one embodiment, muscular hypertrophy refers to an increase in the number of actin and myosin contractile proteins.

As used herein, the terms "promoting," "enhancing," "stimulating," or "increasing" generally refer to the ability of a Wnt polypeptide or composition of the invention to produce or cause a greater physiological response (i.e., measurable downstream effect), as compared to the response caused by either vehicle or a control molecule/composition. One such measurable physiological response includes, without limitation, an increase in symmetrical stem cell division compared to asymmetrical cell division, e.g., increase in satellite stem cells, and/or an increase muscle hypertrophy compared to normal, untreated, or control-treated muscle cells. Wnt polypeptides and compositions of the invention can also have "improved," "increased," "enhanced," or "greater" physical and pharmacokinetic properties compared to Wnt polypeptides found in nature. For example, the physiological response, physical properties, or pharmacokinetic properties of the inventive Wnt polypeptides may be increased by at least 5%, 10%, 20%, 30%, 40%, 50%, 60%, 70%, 80%, 90%, 100%, 125%, 150%, 175%, 200%, or greater. In another non-limiting example, the physiological response, physical properties, or pharmacokinetic properties of the inventive Wnt polypeptides of a Wnt composition of the invention may be increased by at least 5%, 10%, 20%, 30%, 40%, 50%, 60%, 70%, 80%, 90%, 100%, 125%, 150%, 175%, 200%, or greater, compared to that of natural Wnts. An "increased" or "enhanced" response or property is typically "statistically significant" , and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) that produced by vehicle (the absence of an agent) or a control Wnt composition.

As used herein, the terms "retaining" or "maintaining," generally refer to the ability of a Wnt composition of the invention to produce or cause a physiological response (i.e., measurable downstream effect) that is of a similar nature to the response caused by a Wnt composition of the naturally occurring Wnt amino acid or nucleic acid sequence. For example, the Wnt compositions of the invention exhibit Wnt biological activity, and thus retain Wnt activity. The compositions of the invention also produce a physiological response, such as muscle hypertrophy, that is of a similar nature to the response caused by a naturally occurring Wnt polypeptide. A Wnt composition of the invention that elicits a similar physiological response may elicit a physiological response that is at least 5%, at least 10% , at least 15%, at least 20%, at least 25%, at least 30%, at least 40%, at least 50%, at least 60%, at least 70%, at least 75%, at least 80%, at least 85%, at least 90%, at least 95% or about 100% of the level of physiological response elicited by a composition comprising a naturally occurring Wnt amino acid or nucleic acid sequence.

As used herein, the terms "decrease" or "lower," or "lessen," or "reduce," or "abate" refers generally to the ability of a Wnt composition of the invention to produce or cause a lesser physiological response (i.e., downstream effects), as compared to the response caused by either vehicle or a control molecule/composition, e.g., decreased apoptosis. In one embodiment, the decrease can be a decrease in gene expression or a decrease in cell signaling that normally is associated with a reduction of cell viability. A "decrease" or "reduced" response is typically a "statistically significant" response, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

C. Wnt Signaling Pathways

The Wnt signaling pathway is an ancient and evolutionarily conserved pathway that regulates crucial aspects of cell fate determination, cell migration, cell polarity, neural patterning and organogenesis during development and throughout adult life. Wnt signaling pathways downstream of the Fzd receptor have been identified, including canonical or Wnt/13-catenin dependent pathways and non-canonical or β-catenin-independent pathways, which can be further divided into Planar Cell Polarity, Wnt/$Ca^{2+}$ pathways, and others.

Wnt proteins bind to the N-terminal extra-cellular cysteine-rich domain of the Frizzled (Fzd) receptor family. There are ten Fzd receptors in humans. The Fzd protein is a seven-transmembrane protein with topological homology to G-protein coupled receptors. In addition, to the interaction between Wnt and Fzd, co-receptors are also required for mediating Wnt signaling. For example the low-density-lipoprotein-related protein 5/6 (LRP5/6) is required to mediate the canonical Wnt signal whereas receptor tyrosine kinase RYK may be required for non-canonical functions.

Another level of regulation of Wnt signaling occurs in the extra-cellular milieu with the presence of a diverse number of secreted Wnt antagonists. After Wnt binds to a receptor complex, the signal is transduced to cytoplasmic phosphoprotein Dishevelled (Dsh/Dvl). Dsh can directly interact with Fzd. At the level of Dsh, the Wnt signal branches into at least three major cascades, canonical (β-catenin), Planar Cell Polarity and Wnt/Ca$^{2+}$. Further, G protein coupled receptor signaling may also stimulate growth and survival pathways such as PI3K.

1. The Canonical Wnt Signaling Pathway

The canonical Wnt signaling pathway was first identified and delineated from genetic screens in *Drosophila* and intensive studies in the fly, worm, frog, fish and mouse have led to the identification of a basic molecular signaling framework. The hallmark of the canonical Wnt pathway is the accumulation and translocation of the adherens junction associated-protein β-catenin into the nucleus. In the absence of Wnt signaling, cytoplasmic β-catenin is degraded by aβ-catenin destruction complex, which includes Axin, adenomatosis polyposis coli (APC), protein phosphatase 2A (PP2A), glycogen synthase kinase 3 β (GSK3β) and casein kinase 1α (CK1α). Phosphorylation of β-catenin within this complex by CKla and GSK3β targets it for ubiquitination and subsequent proteolytic destruction by the proteosomal machinery. Binding of Wnt to its receptor complex composed of the Fzd and the LRP5/6 induces the dual phosphorylation of LRP6 by CK1 and GSK3-β and this allows for the translocation of a protein complex containing Axin from the cytosol to the plasma membrane. Dsh is also recruited to the membrane and binds to Fzd and Axin binds to phosphorylated LRP5/6. This complex formed at the membrane at Fzd/LRP5/6 induces the stabilization of β-cat via either sequestration and/or degradation of Axin. β-catenin translocates into the nucleus where it complexes with Lef/Tcf family members to mediate transcriptional induction of target genes.

Canonical Wnt signaling affects formation of anterior head structure and neuroectodermal pattering, posterior patterning and tail formation, as well as for formation of various organ systems including the heart, lungs, kidney, skin and bone.

2. The Non-Canonical Wnt Signaling Pathway

The non-canonical pathway is often referred to as the β-catenin-independent pathway and, while not as well-defined as the canonical pathway, this pathway can be further divided into at least two distinct branches, the Planar Cell Polarity pathway (or PCP pathway) and the Wnt/Ca2+ pathway, of which only the PCP is discussed in further detail herein. The PCP pathway emerged from genetic studies in *Drosophila* in which mutations in Wnt signaling components including Frizzled and Dishevelled were found to randomize the orientation of epithelial structures including cuticle hairs and sensory bristles. Cells in the epithelia are known to possess a defined apical-basolateral polarity but, in addition, they are also polarized along the plane of the epithelial layer. This rigid organization governs the orientation of structures including orientation of hair follicles, sensory bristles and hexagonal array of the ommatidia in the eye. In vertebrates, this organization has been shown to underlie the organization and orientation of muscle cells, stereo-cilia in the sensory epithelium of the inner ear, the organization of hair follicles, and the morphology and migratory behavior of dorsal mesodermal cells undergoing gastrulation.

Wnt signaling is transduced through Fzd independent of LRP5/6 leading to the activation of Dsh. Dsh through Daaml mediates activation of Rho which in turn activates Rho kinase (ROCK). Daaml also mediates actin polymerization through the actin binding protein Profilin. Dsh also mediates activation of Rac, which in turn activates JNK. The signaling from Rock, JNK and Profilin are integrated for cytoskeletal changes for cell polarization and motility during gastrulation.

3. Wnt Signaling in Muscle Cell Development

Satellite stem cells are adult stem cells that give rise to muscle cells. Satellite cells in adult skeletal muscle are located in small depressions between the sarcolemma of their host myofibers and the basal lamina. Upon damage, such as physical trauma, repeated exercise, or in disease, satellite cells become activated, proliferate and give rise to a population of myogenic precursor cells (myoblasts) expressing the myogenic regulatory factors (MRF) MyoD and Myf5. In the course of the regeneration process, myoblasts undergo multiple rounds of division before committing to terminal differentiation, fusing with the host fibers or generating new myofibers to reconstruct damaged tissue (Charge and Rudnicki, 2004). During skeletal muscle regeneration, the satellite stem cell population is expanded or maintained by a stem cell subpopulation, thus allowing tissue homeostasis and multiple rounds of regeneration during the lifespan of an individual (Kuang et al., 2008). Satellite stem cells (Pax7$^+$/Myf5$^-$) represent about 10% of the adult satellite cell pool, and give rise to daughter satellite myogenic cells (Pax7$^+$/Myf5$^+$) through asymmetric apical-basal cell divisions.

Wnt signaling plays a key role in regulating developmental programs through embryonic development, and in regulating stem cell function in adult tissues (Clevers, 2006). Wnts are necessary for embryonic myogenic induction in the paraxial mesoderm (Borello et al., 2006; Chen et al., 2005; Tajbakhsh et al., 1998), as well in the control of differentiation during muscle fiber development (Anakwe et al., 2003). Recently, the Wnt planar cell polarity (PCP) pathway has been implicated in regulating the orientation of myocyte growth in the developing myotome (Gros et al., 2009). In the adult, Wnt signaling is thought to be necessary for the myogenic commitment of adult stem cells in muscle tissue following acute damage (Polesskaya et al., 2003; Torrente et al., 2004). Other studies suggest that Wnt/β-catenin signaling regulates myogenic differentiation through activation and recruitment of reserve myoblasts (Rochat et al., 2004). In addition, the Wnt/β-catenin signaling in satellite cells within adult muscle appears to control myogenic lineage progression by limiting Notch signaling and thus promoting differentiation (Brack et al., 2008).

Recently, it was determined that the Wnt receptor Fzd7 was markedly upregulated in quiescent satellite stem cells. In addition, further studies revealed that Wnt7a is expressed during muscle regeneration and acts through its receptor Fzd7 and Vang12, a component of the planar cell polarity (PCP) pathway, to induce symmetric satellite stem cell expansion and dramatically enhance muscle regeneration.

Inhibition of receptor or effector molecules in the PCP pathway, e.g., Fzd7 or Vang12, is believed to abrogate the effects of Wnt7a on satellite stem cells (Le Grand et al., 2009). It has further been demonstrated that administration of lipidated Wnt7a polypeptide, or a polynucleotide encoding a Wnt7a polypeptide that is subsequently post-translationally modified by lipidation, significantly increased satellite stem cell numbers in vitro and in vivo, and promoted tissue formation in vivo, leading to enhanced repair and regeneration in injured and diseased muscle tissue (Le Grand et al., 2009).

Without wishing to be bound to any particular theory, it is contemplated that the mechanism of action of Wnt7a that leads to enhanced repair and regeneration in injured and diseased muscle tissue has two paths: Wnt7a may stimulate the symmetrical expansion of muscle satellite (stem) cells through a PCP pathway, resulting in a larger pool of cells that can subsequently differentiate into myoblasts; and secondly, Wnt7a via the G protein coupled receptor (Frizzled) may stimulate phosphatidylinositol 3-kinase/Akt (protein kinase B)/mammalian target of rapamycin (PI3K/Akt/mTOR) pathway signaling in myoblasts and myofibers, which has been shown to stimulate hypertrophy (Bodine et al., *Nature Cell Biology*. 2001; vol. 3; pp. 1014-1017; Glass et al., *Nature Cell Biology*. 2003; vol. 5; pp. 87-90; Ciciliot and Schiaffino, *Current Pharmaceutical Design*. 2010; 16(8); pp. 906-914). Wnt7a can signal via the G-protein coupled receptor Frizzled 7 and this Wnt/Frz interaction may contribute to both biological effects.

In various embodiments, compositions comprise a modified Wnt, particularly Wnt fusion polypeptide (e.g., Fc-fusion) or truncated Wnt polypeptides lacking N-terminal and/or C-terminal amino acids. The truncated Wnt polypeptides of the invention lack one or more lipidation sites but still unexpectedly retain Wnt biological activity, receptor binding specificity, and have improved solubility, production, systemic delivery, and tissue uptake compared to lipidated Wnts. In particular embodiments, the inventive compositions comprise a modified Wnt7a, particularly Wnt7a fusion polypeptide or truncated Wnt7a polypeptides lacking N-terminal and/or C-terminal amino acids e.g., a Wnt7a polypeptide lacking at least the N-terminal 220 amino acids. The truncated Wnt7a polypeptides lack one or more lipidation sites but still unexpectedly retain Wnt7a biological activity, receptor binding specificity, and have improved solubility, production, systemic delivery, and tissue uptake compared to lipidated Wnts.

Although the importance of the PI3K/Akt/mTOR pathway for muscle cell hypertrophy has been described, the therapeutic challenge to specifically stimulate this pathway in muscle cells poses significant obstacles to enhancing repair and regeneration in injured and diseased muscle tissue. Early studies with potent PI3-kinase activators such as IGF-1 produced hypertrophy in vitro but the possibility exists for "off-target" metabolic effects (i.e., IGF-1 and PI3K are key regulators of housekeeping metabolic, survival and metabolic processes). Thus, the potential for a muscle-specific Wnt7a-Fzd7 stimulation of PI3K/Akt/mTOR pathway would represent an important and unique therapeutic breakthrough.

As described in further detail below, the present invention contemplates, in part, inventive Wnt polypeptides that provide an unexpected solution to this technological hurdle as well as other obstacles to the therapeutic use of Wnt polypeptides to enhance repair and regeneration in injured and diseased muscle tissue.

D. Polypeptides

Wnt signaling pathways are key components of cell signaling networks. The human Wnt gene family consists of 19 members, encoding evolutionarily conserved glycoproteins with 22 or 24 Cys residues and several conserved Asn and Ser residues. Exemplary human Wnt proteins include Wnt1, Wnt2, Wnt2b/13, Wnt3, Wnt3a, Wnt4, Wnt5a, Wnt5b, Wnt6, Wnt7a, Wnt7b, Wnt8, Wnt8a, Wnt8b, Wnt9a, Wnt9b, Wnt10a, Wnt10b, Wnt11, and Wnt16.

The Wnts are secreted glycoproteins that are heavily modified prior to transport and release into the extra-cellular milieu. After signal sequence cleavage and translocation into the endoplasmic reticulum (ER), Wnts are transported through the endomembrane system to the cell surface and undergo several modifications. Wnts undergo N-linked glycosylation (Burrus and McMahon 1995; Kadowaki et al., 1996; Komekado et al., 2007; Kurayoshi et al., 2007; Mason et al., 1992; Smolich et al., 1993; Tanaka et al. 2002). Many Wnts also are palmitoylated at the first conserved cysteine, e.g., C93 in Wnt1, C77 in Wnt3a, and C104 in Wnt5a (Galli et al., 2007; Kadowaki et al., 1996; Komekado et al., 2007; Willert et al. 2003). In addition, Wnt3a is modified with palmitoleic acid at a conserved serine, S209, which is also conserved in Wnt1 (S224) Wnt5a (Takada et al., 2006). Furthermore, these conserved cysteine and serine residues are present in the N-terminus of many Wnts, e.g., Wnt1, Wnt3a, Wnt4, Wnt5a, Wnt6, Wnt7a, Wnt9a, Wnt10a, and Wnt 11, among others (Takada et al., 2006).

Wnt acylation is widely accepted to cause the notoriously hydrophobic nature of secreted Wnts (Willert et al., 2003). In addition, post-translational lipidation of mammalian Wnts is believed to be important for function. Mutating a conserved N-terminal cysteine of Wnt1, Wnt3a, or Wnt5a prevented palmitoylation in cell culture. These mutant Wnts were secreted but were shown to have little or no signaling activity (Galli et al., 2007; Komekado et al., 2007; Kurayoshi et al., 2007; Willert et al., 2003), and unpalmitoylated Wnts are believed to be unable to bind Fzd receptors (Komekado et al., 2007; Kurayoshi et al. 2007). Mutating the conserved serine in the central portion of Wnt3a prevented palmitoleic acid addition and blocked secretion and thus, activity (Takada et al., 2006). Research on Drosophila Wg confirmed the importance of acylation (Franch-Marro et al., 2008a; Nusse 2003; van den Heuvel et al., 1993).

Further, these data are supported by the porcupine (porc) phenotype in *Drosophila*, which shows a strong loss of Wg signaling (van den Heuvel et al., 1993). Porc is an ER-localized integral membrane O-acyl transferase (Kadowaki et al., 1996) required for Wg palmitoylation (Zhai et al., 2004), and for Wg ER exit (Tanaka et al., 2002). Vertebrate Porc also promotes Wnt lipidation and is required for Wnt signaling and Wnt biological activity (Galli et al., 2007).

These studies establish a model in which palmitoleic acid-modification is required for secretion, and palmitate for Fzd binding. Thus, Wnt polypeptides that lack the N-terminal amino acid sequence for either or both of these reported lipid modifications would be expected to lack biological activity.

In various embodiments, the invention contemplates, in part, Wnt polypeptides, e.g., truncated Wnts, Wnt fusion polypeptides, that retain Wnt biological activity but that have been engineered to remove post-translational modification sites in the N-terminus of Wnts that adversely affect solubility, production, systemic delivery, and tissue uptake. In particular embodiments, the inventive Wnt polypeptides promote stem and progenitor cell expansion and muscle hypertrophy, and promote cell and/or tissue formation, regeneration, maintenance and repair. As used herein, the term "canonical" refers to an amino acid or group of amino acids present in the naturally occurring polypeptide. In some contexts, "canonical" is used interchangeably with "native" when referring to amino acids present in the naturally occurring polypeptide.

In certain embodiments, a Wnt polypeptide is truncated, e.g., lacks N-terminal and/or C-terminal amino acids of the native Wnt polypeptide. In certain particular embodiments, the Wnt polypeptide comprises an N-terminal and/or C-terminal truncation but retains or has increased canonical and/or non-canonical Wnt signaling activity.

As used herein, the terms "polypeptide," "peptide," and "protein" are used interchangeably, unless specified to the contrary, and according to conventional meaning, i.e., as a sequence of amino acids linked by peptide bonds or modified peptide bonds. Polypeptides of the invention include, but are not limited to, truncated polypeptides, biologically active polypeptide fragments, and fusion polypeptides, as described elsewhere herein. Polypeptides are not limited to a specific length, e.g., they may comprise a full length protein polypeptide or a fragment of a full length polypeptide, and may include post-translational modifications of the polypeptide, for example, glycosylations, acetylations, phosphorylations and the like, as well as other modifications known in the art, both naturally occurring and non-naturally occurring. Polypeptides of the invention may be prepared using any of a variety of well known recombinant and/or synthetic techniques, illustrative examples of which are further discussed below. In one embodiment, the Wnt polypeptide is a truncated Wnt1, Wnt2, Wnt2b/13, Wnt3, Wnt3a, Wnt4, Wnt5a, Wnt5b, Wnt6, Wnt7a, Wnt7b, Wnt8, Wnt8a, Wnt8b, Wnt9a, Wnt9b, Wnt10a, Wnt10b, Wnt11, or Wnt16 polypeptide.

In another embodiment, the Wnt polypeptide is an Fc-fusion polypeptide comprising all, or a biologically active fragment of, a Wnt1, Wnt2, Wnt2b/13, Wnt3, Wnt3a, Wnt4, Wnt5a, Wnt5b, Wnt6, Wnt7a, Wnt7b, Wnt8, Wnt8a, Wnt8b, Wnt9a, Wnt9b, Wnt10a, Wnt10b, Wnt11, or Wnt16 polypeptide.

In a preferred embodiment, the Wnt polypeptide is a Wnt7a polypeptide, truncated Wnt7a polypeptide, or Wnt7a Fc-fusion polypeptide, or a combination thereof.

As used herein, the term "Wnt7a polypeptide," refers to a Wnt7a protein having a polypeptide sequence corresponding to a wild type Wnt7a sequence. In some embodiments, the term "Wnt7a polypeptide," refers to a Wnt7a polypeptide, truncated Wnt7a polypeptide, biologically active Wnt7a polypeptide fragment, or Wnt7a fusion polypeptide having a Wnt7a amino acid sequence that is at least about 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%, identical to a reference Wnt7a sequence. Identity may be assessed over at least about 10, 25, 50, 75, 100, 125, 150, 175, 200, 300, or more contiguous amino acids, or may be assessed over the full length of the sequence. Methods for determining % identity or % homology are known in the art and any suitable method may be employed for this purpose. Illustrative examples of Wnt7a polypeptides are set forth in SEQ ID NOs: 2-23.

However, in particular embodiments, Wnt polypeptides of the invention have been engineered such that they comprise N-terminal and/or C-terminal deletions or truncations, and in particular embodiments the Wnt polypeptides comprise N-terminal and/or C-terminal deletions or truncations and retain non-canonical Wnt signaling activity. In some embodiments, the Wnt polypeptides comprise N-terminal and/or C-terminal deletions or truncations, lack one or more lipidation sites, and retain non-canonical Wnt signaling activity. In particular embodiments, the Wnt polypeptide is a Wnt7a polypeptide comprising an N-terminal and/or C-terminal deletion or truncation, and retaining non-canonical Wnt signaling activity. In some embodiments, the Wnt7a polypeptide comprises N-terminal and/or C-terminal deletions or truncations, lacks one or more lipidation sites, and retains non-canonical Wnt signaling activity.

As used herein, the terms "truncated Wnt polypeptide," or "Wnt polypeptide comprising an N-terminal and/or C-terminal truncation or deletion," are used interchangeably and refer to Wnt polypeptides lacking N-terminal or C-terminal amino acid residues or biologically active fragments of a Wnt polypeptide or variants thereof, or homolog, paralog, or ortholog thereof that comprises one or more amino acid deletions. In particular embodiments of the invention, truncated Wnt polypeptides comprise one or more amino acid deletions but result in a polypeptide that retains Wnt biological activity. In particular embodiments, truncated Wnt polypeptides retain at least 100%, at least 90%, at least 80%, at least 70%, at least 60%, at least 50%, at least 40%, at least 30%, at least 20%, at least 10%, or at least 5% of the naturally occurring Wnt polypeptide activity.

As used herein, the terms "N-terminal deletion" and "N-terminal truncation" are often used interchangeably and refer to a deletion of N-terminal amino acids from a polypeptide. For example: a polypeptide comprising 349 amino acids and having an N-terminal deletion of 220 amino acids results in a polypeptide comprising 129 C-terminal amino acids of the polypeptide; a polypeptide comprising 349 amino acids and having an N-terminal deletion of 234 amino acids results in a polypeptide comprising 115 C-terminal amino acids of the polypeptide; and a polypeptide comprising 349 amino acids and having an N-terminal deletion of 263 amino acids results in a polypeptide comprising 86 C-terminal amino acids of the polypeptide. In particular embodiments, a Wnt polypeptide according to the invention, e.g., Wnt7a, comprises an N-terminal deletion or truncation of at least 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, or 284 N-terminal amino acids. In particular embodiments, a Wnt polypeptide comprising an N-terminal truncation will also comprise one or more C-terminal amino acid truncations or deletions.

In particular embodiments, a Wnt polypeptide according to the invention, comprises an N-terminal deletion or truncation sufficient to eliminate one or more Wnt lipidation sites. In a certain embodiment, a Wnt polypeptide comprises an N-terminal deletion of at least 50, 60, 70, 80, 90, 100, 110, 120, 130, 140, 150, 160, 170, 180, 190, 200, 210, 220, 230, 240, 250, 260, 270, 280, 290 or 300 N-terminal amino acids.

As used herein, the terms "C-terminal deletion" and "C-terminal truncation" are often used interchangeably and refer to a deletion of one or more C-terminal amino acids from a polypeptide. For example: a polypeptide comprising 349 amino acids and having an C-terminal deletion of 10 amino acids results in a polypeptide comprising 339 N-terminal amino acids of the polypeptide; and a polypeptide comprising 349 amino acids and having an C-terminal deletion of 20 amino acids results in a polypeptide comprising 329 N-terminal amino acids of the polypeptide. In particular embodiments, a Wnt polypeptide according to the invention comprises a C-terminal deletion or truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 C-terminal amino acids. In particular embodiments, a Wnt polypeptide comprising a C-terminal truncation will also comprise one or more N-terminal amino acid truncations or deletions.

In particular embodiments, truncated Wnt polypeptides according to the invention comprise one or more N-terminal amino acid truncations and one or more C-terminal amino acid truncations as described elsewhere herein. In certain embodiments, truncated Wnt polypeptides comprise an N-terminal deletion or truncation of about 10 to about 300 N-terminal amino acids and a C-terminal deletion or truncation of about 1 to about 50 C-terminal amino acids.

In certain embodiments, truncated Wnt polypeptides comprise an N-terminal deletion or truncation of about 220 to about 284 N-terminal amino acids and a C-terminal deletion or truncation of about 1 to about 50 C-terminal amino acids.

In one embodiment, the present invention contemplates a Wnt polypeptide comprising a minimal biologically active fragment of a Wnt polypeptide comprising one or more N-terminal amino acid truncations and one or more C-terminal amino acid truncations as described elsewhere herein. As used herein, the term "minimal active fragment" or "minimal biologically active fragment" refers to a Wnt polypeptide fragment that retains at least 100%, at least 90%, at least 80%, at least 70%, at least 60%, at least 50%, at least 40%, at least 30%, at least 20%, at least 10%, or at least 5% of the naturally occurring Wnt polypeptide activity. In particular embodiments, the present invention contemplates, minimal biologically active Wnt fragments comprising 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, or 129 contiguous amino acids of aWnt polypeptide.

In particular embodiments, the naturally occurring Wnt polypeptide activity, or Wnt biological activity, is non-canonical Wnt signaling activity. In particular embodiments, the Wnt7a biological activity is non-canonical Wnt7a signaling activity.

In another embodiment, a minimal biologically active Wnt fragment comprising 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, or 129 contiguous amino acids of the amino acid sequence set forth in SEQ ID NO: 3 is provided.

In particular embodiments, a biologically active fragment of a Wnt polypeptide can be a polypeptide fragment which is, for example, 30, 35, 40, 45, 50, 55, 60, 0, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 contiguous or non-contiguous amino acids, including all integers (e.g., 101, 102, 103) and ranges (e.g., 50-75, 75-100, 125-150) in between, of the Wnt polypeptide amino acid sequences known in the art or referenced or otherwise disclose herein. In certain embodiments, a biologically active Wnt polypeptide fragment comprises a canonical activity-related sequence, domain, or motif of a naturally occurring Wnt polypeptide. In certain embodiments, a Wnt polypeptide according to the present invention comprises one or more N-terminal amino acid truncations and one or more C-terminal amino acid truncations as described elsewhere herein.

In particular embodiments, a biologically active fragment of a Wnt7a polypeptide can be a polypeptide fragment which is, for example, 30, 35, 40, 45, 50, 55, 60, 0, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, or 129 contiguous or non-contiguous amino acids, including all integers (e.g., 101, 102, 103) and ranges (e.g., 50-75, 75-100, 100-129) in between, of the amino acid sequences set forth in any one of the Wnt7a polypeptides described herein. In certain embodiments, a biologically active Wnt7a polypeptide fragment comprises a canonical activity-related sequence, domain, or motif of a naturally occurring Wnt7a polypeptide. In certain embodiments, a Wnt7a polypeptide according to the present invention comprises one or more N-terminal amino acid truncations and one or more C-terminal amino acid truncations as described elsewhere herein.

In certain embodiments, truncated Wnt polypeptides comprise an N-terminal deletion or truncation of about 220 to about 284 N-terminal amino acids, including all integers and ranges in between (e.g., 221, 222, 223, 224, 225) and a C-terminal deletion or truncation of about 1 to about 50 C-terminal amino acids, including all integers and ranges in between (e.g., 1, 2, 3, 4, 5), so long as the truncated Wnt7a polypeptide retains the activity of the naturally occurring Wnt7a polypeptide. Typically, the biologically active fragment has no less than about 1%, 5%, 10%, 20%, 30, 40%, 50%, 60%, 70%, 80%, 90%, or 100% of an activity of the naturally occurring Wnt7a polypeptide from which it is derived, such as non-canonical Wnt signaling activity.

In some embodiments, truncated Wnt polypeptides, e.g., biologically active Wnt polypeptide fragments, bind to one or more cellular binding partners, e.g., Frizzled receptors, with an affinity of at least about 1%, 5%, 10%, 20%, 30, 40%, 50%, 60%, 70%, 80%, 90%, or 100% of the affinity of the naturally occurring Wnt polypeptide binding affinity to the same cellular binding partner(s). In some embodiments, the binding affinity of a truncated Wnt polypeptide for a selected cellular binding partner, particularly a binding partner that participates in a canonical activity, can be stronger than that of the naturally occurring Wnt polypeptide's corresponding binding affinity, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

The invention further contemplates Wnt polypeptides, truncated Wnt polypeptides, biologically active Wnt polypeptide fragments, and Wnt fusion polypeptides comprising one or more amino acid mutations, additions, or substitutions. In particular embodiments, Wnt polypeptides of the invention comprising one or more amino acid mutations, additions, and/or substitutions but that retain or have increased Wnt biological activity. Preferably, Wnt polypeptides comprising one or more amino acid mutations, additions, and/or substitutions retain at least 100%, at least 90%, at least 80%, at least 70%, at least 60%, at least 50%, at least 40%, at least 30%, at least 20%, at least 10%, or at least 5% of the naturally occurring Wnt activity.

The invention further contemplates Wnt7a polypeptides, truncated Wnt7a polypeptides, biologically active Wnt7a polypeptide fragments, and Wnt7a fusion polypeptides comprising one or more amino acid mutations, additions, or substitutions. In particular embodiments, Wnt7a polypeptides of the invention comprising one or more amino acid mutations, additions, and/or substitutions but that retain or have increased Wnt7a biological activity. Preferably, Wnt7a polypeptides comprising one or more amino acid mutations, additions, and/or substitutions retain at least 100%, at least 90%, at least 80%, at least 70%, at least 60%, at least 50%, at least 40%, at least 30%, at least 20%, at least 10%, or at least 5% of the naturally occurring Wnt7a activity.

As used herein, the term "naturally occurring", refers to a polypeptide or polynucleotide sequence that can be found in nature. For example, a naturally occurring polypeptide or polynucleotide sequence would be one that is present in an organism, and can be isolated from the organism, and which has not been intentionally modified by man in the laboratory. The term "wild-type" is often used interchangeably with the term "naturally occurring."

As used herein, Wnt polypeptides, e.g., Wnt7a, truncations, biologically active fragments thereof, and Wnt fusion polypeptides that retains the "naturally occurring Wnt activity," "naturally occurring Wnt7a activity," "normal Wnt activity," or "unmodified Wnt activity," refers to a modified Wnt polypeptide, e.g., Wnt7a, that generate a physiological response or that have physical or pharmacokinetic properties that are at least 100%, at least 90%, at least 80%, at least 70%, at least 60%, at least 50%, at least 40%, at least 30%, at least 20%, at least 10%, or at least 5% of the physiological response or physical or pharmacokinetic properties of the corresponding naturally occurring Wnt polypeptide, e.g., Wnt7a. In some embodiments, the Wnt7a polypeptide of the invention retains non-canonical Wnt signaling activity.

In the context of the invention, a truncated polypeptide, biologically active fragment or variant, or homolog, paralog, or ortholog thereof, or a fusion polypeptide is considered to have at least substantially the same activity as the wild-type protein when it exhibits about 10%, 20%, 30%, 40% or 50% of the activity of the wild-type protein, preferably at least 50%, at least 55%, at least 60%, at least 65%, at least 70%, at least 75%, or at least 80% of the activity of the wild type protein. In particular embodiments, the truncated polypeptide, biologically active fragment or variant, or homolog, paralog, or ortholog thereof, or a fusion polypeptide exhibits at least 70%, at least 80%, at least 90%, at least 95% or about 100% of the activity of the wild-type protein. In certain embodiments, an activity greater than wild type activity may be achieved.

Activity of a truncated Wnt polypeptide, a biologically active Wnt polypeptide fragment or variant, or homolog, paralog, or ortholog thereof, or a Wnt fusion polypeptide for example, can be determined by measuring its ability to mimic wild-type Wnt biological activity by, for example, stimulating the Wnt signaling pathway, such as by promoting symmetrical stem cell expansion or cell growth, and comparing the ability to the activity of a wild type protein. Methods of measuring and characterizing stem cell division, e.g., satellite stem cell division, and cell growth, e.g., muscle hypertrophy are known in the art.

Truncated polypeptides of the invention may include polypeptide variants. The term "variant" as used herein, refers to polypeptides that are distinguished from a reference polypeptide by the modification, addition, deletion, or substitution of at least one amino acid residue, as discussed elsewhere herein and as understood in the art. In certain embodiments, a polypeptide variant is distinguished from a reference polypeptide by one or more amino acid substitutions (e.g., 1, 2, 3, 4, 5 or more substitutions), which may be conservative or non-conservative. For example, in various embodiments, one or more conservative or non-conservative substitutions can be made in any amino acid residue found in the naturally occurring Wnt polypeptide.

In other particular embodiments, Wnt polypeptide variants comprise one or more amino acid additions, deletions, or substitutions in order to increase Wnt pathway signaling activity, and/or to increase stability, solubility, systemic delivery, and/or tissue uptake of the Wnt polypeptides of the invention compared to a naturally occurring Wnt polypeptide.

To generate such variants, one skilled in the art, for example, can change one or more of the codons of the encoding DNA sequence, e.g., according to Table 1.

TABLE 1

Amino Acid Codons

| Amino Acids | Codons | | | | |
|---|---|---|---|---|---|
| Alanine | GCA | GCC | GCG | GCU | |
| Cysteine | UGC | UGU | | | |
| Aspartic acid | GAC | GAU | | | |
| Glutamic acid | GAA | GAG | | | |
| Phenylalanine | UUC | UUU | | | |
| Glycine | GGA | GGC | GGG | GGU | |
| Histidine | CAC | CAU | | | |
| Isoleucine | AUA | AUC | AUU | | |
| Lysine | AAA | AAG | | | |
| Leucine | UUA | UUG | CUA | CUC | CUG | CUU |
| Methionine | AUG | | | | |
| Asparagine | AAC | AAU | | | |
| Proline | CCA | CCC | CCG | CCU | |
| Glutamine | CAA | CAG | | | |
| Arginine | AGA | AGG | CGA | CGC | CGG | CGU |
| Serine | AGC | AGU | UCA | UCC | UCG | UCU |
| Threonine | ACA | ACC | ACG | ACU | |
| Valine | GUA | GUC | GUG | GUU | |
| Tryptophan | UGG | | | | |
| Tyrosine | UAC | UAU | | | |

Guidance in determining which amino acid residues can be substituted, inserted, or deleted without abolishing biological or immunological activity can be found using computer programs well known in the art, such as DNASTAR™ software. If desired, amino acid substitutions can be made to change and/or remove functional groups from a polypeptide. Alternatively, amino acid changes in the protein variants disclosed herein can be conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. See Table 2.

TABLE 2

Conservative Amino Acid Substitutions

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |

TABLE 2-continued

Conservative Amino Acid Substitutions

| Original residue | Conservative substitution |
| --- | --- |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative (or non-conservative) substitutions.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

Polypeptide variants of the invention include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. In certain embodiments, truncations or deletions of regions which do not affect functional activity of the proteins are also variants.

Amino acids in polypeptides of the present invention that are essential for function can be identified by methods known in the art, such as site-directed mutagenesis or alanine-scanning mutagenesis (Cunningham and Wells, *Science* 244:1081-1085, 1989). Sites that are critical for ligand-receptor binding can also be determined by structural analysis such as crystallization, nuclear magnetic resonance or photoaffinity labeling (Smith et al., *J. Mol. Biol.* 224:899-904, 1992 and de Vos et al. *Science* 255:306-312, 1992).

Certain changes do not significantly affect the folding or activity of the protein. The number of amino acid substitutions a skilled artisan would make depends on many factors, including those described above. Generally speaking, the number of substitutions for any given polypeptide will not be more than 50, 40, 30, 25, 20, 15, 10, 5 or 3.

In addition, pegylation of polypeptides and/or muteins is expected to provide improved properties, such as increased half-life, solubility, and protease resistance. Pegylation is well known in the art.

Sequence identity may be used to compare the primary structure of two polynucleotides or polypeptide sequences, describe the primary structure of a first sequence relative to a second sequence, and/or describe sequence relationships such as variants and homologues. Sequence identity measures the residues in the two sequences that are the same when aligned for maximum correspondence. When comparing polypeptide sequences, two sequences are said to be "identical" if the sequence of amino acids in the two sequences is the same when aligned for maximum correspondence, as described below. Sequence relationships can be analyzed using computer-implemented algorithms. The sequence relationship between two or more polynucleotides or two or more polypeptides can be determined by computing the best alignment of the sequences and scoring the matches and the gaps in the alignment, which yields the percent sequence identity and the percent sequence similarity. Polynucleotide relationships can also be described based on a comparison of the polypeptides each encodes. Many programs and algorithms for comparison and analysis of sequences are known.

Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) *A model of evolutionary change in proteins.*" In "*Atlas of Protein Sequence and Structure*, Vol. 5, Suppl. 3 (ed. M. O. Dayhoff), pp. 345-352. Natl. Biomed. Res. Found., Washington, D.C. and Henikoff et al. (1992) *Proc. Natl. Acad. Sci. USA* 89:10915-10919. The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al., (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al., (1997) *Nucleic Acids Res.* 25:3389-3402.

In addition, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. In one embodiment, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1992) *Proc Natl Acad Sci USA* 89:10915-10919). GAP uses the algorithm of Needleman and Wunsch (1970) *J Mol Biol* 48:443-453, to find the alignment of two complete sequences that maximizes the number of matches and minimizes the number of gaps.

In one particular embodiment, the truncated Wnt polypeptides comprise an amino acid sequence that can be optimally aligned with a polypeptide sequence of any one of SEQ ID NOs: 3-5 to generate a BLAST bit scores or sequence similarity scores of at least 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 256, 247, 248, 249, 250, 251, 252, 253, 254, 255, 256, 257, 258, 259, 260, 261, 262, 263, 264, 265, 266, 267, 268, 269, 270, 271, 272, 273, 274, or 275, wherein the BLAST alignment used the BLOSUM62 matrix, a gap existence penalty of 11, and a gap extension penalty of 1.

In one particular embodiment, the truncated Wnt polypeptides comprise an amino acid sequence that can be optimally aligned with a polypeptide sequence of any one of SEQ ID NOs: 3-5 to generate a BLAST e-value score of at least e-52, e-53, e-54, e-55, e-56, e-57, e-58, e-59, e-60, e-61, e-62, e-63, e-64, e-65, e-66, e-67, e-68, e-69, e-70, e-71, e-72, e-73, e-74, e-75, e-76, e-77, e-78, e-79, or e-80, wherein the BLAST alignment used the BLOSUM62 matrix, a gap existence penalty of 11, and a gap extension penalty of 1.

In particular embodiments, truncated Wnt polypeptides comprise an amino acid sequence that can be optimally aligned with a polypeptide sequence of SEQ ID NO: 3 to generate a similarity score of 220 to 275, wherein the BLAST alignment used the BLOSUM62 matrix, a gap existence penalty of 11, and a gap extension penalty of 1. In particular embodiments, truncated Wnt polypeptides comprise an amino acid sequence that can be optimally aligned with a polypeptide sequence of SEQ ID NO: 3 to generate an e-value score of e-74 to 2e-78, wherein the BLAST alignment used the BLOSUM62 matrix, a gap existence penalty of 11, and a gap extension penalty of 1.

In particular embodiments, truncated Wnt polypeptides comprise an amino acid sequence that can be optimally aligned with a polypeptide sequence of SEQ ID NO: 4 to generate a similarity score of 210 to 242, wherein the BLAST alignment used the BLOSUM62 matrix, a gap existence penalty of 11, and a gap extension penalty of 1. In particular embodiments, truncated Wnt polypeptides comprise an amino acid sequence that can be optimally aligned with a polypeptide sequence of SEQ ID NO: 3 to generate an e-value score of e-66 to e-69, wherein the BLAST alignment used the BLOSUM62 matrix, a gap existence penalty of 11, and a gap extension penalty of 1.

In particular embodiments, truncated Wnt polypeptides comprise an amino acid sequence that can be optimally aligned with a polypeptide sequence of SEQ ID NO: 5 to generate a similarity score of 171 to 184, wherein the BLAST alignment used the BLOSUM62 matrix, a gap existence penalty of 11, and a gap extension penalty of 1. In particular embodiments, truncated Wnt polypeptides comprise an amino acid sequence that can be optimally aligned with a polypeptide sequence of SEQ ID NO: 3 to generate an e-value score of e-52 to 3e-52, wherein the BLAST alignment used the BLOSUM62 matrix, a gap existence penalty of 11, and a gap extension penalty of 1.

In certain embodiments, truncated Wnt polypeptides comprise an amino acid sequence that can be optimally aligned with a polypeptide sequence of SEQ ID NO: 3 to generate a similarity score of at least 220, wherein the BLAST alignment used the BLOSUM62 matrix, a gap existence penalty of 11, and a gap extension penalty of 1. In particular embodiments, truncated Wnt polypeptides comprise an amino acid sequence that can be optimally aligned with a polypeptide sequence of SEQ ID NO: 3 to generate an e-value score of at least e-74, wherein the BLAST alignment used the BLOSUM62 matrix, a gap existence penalty of 11, and a gap extension penalty of 1.

In certain embodiments, truncated Wnt polypeptides comprise an amino acid sequence that can be optimally aligned with a polypeptide sequence of SEQ ID NO: 4 to generate a similarity score of at least 210, wherein the BLAST alignment used the BLOSUM62 matrix, a gap existence penalty of 11, and a gap extension penalty of 1. In particular embodiments, truncated Wnt polypeptides comprise an amino acid sequence that can be optimally aligned with a polypeptide sequence of SEQ ID NO: 3 to generate an e-value score of at least e-66, wherein the BLAST alignment used the BLOSUM62 matrix, a gap existence penalty of 11, and a gap extension penalty of 1.

In certain embodiments, truncated Wnt polypeptides comprise an amino acid sequence that can be optimally aligned with a polypeptide sequence of SEQ ID NO: 5 to generate a similarity score of at least 171, wherein the BLAST alignment used the BLOSUM62 matrix, a gap existence penalty of 11, and a gap extension penalty of 1. In particular embodiments, truncated Wnt polypeptides comprise an amino acid sequence that can be optimally aligned with a polypeptide sequence of SEQ ID NO: 3 to generate an e-value score of at least e-52, wherein the BLAST alignment used the BLOSUM62 matrix, a gap existence penalty of 11, and a gap extension penalty of 1.

In another illustrative approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

E. Fusion Polypeptides

In various embodiments, the present invention contemplates, in part, fusion polypeptides, and polynucleotides encoding fusion polypeptides. In one embodiment, the fusion polypeptide comprises a truncated Wnt polypeptide, a biologically active Wnt polypeptide fragment, and/or such peptides further comprising one or more amino acid mutations, substitutions, and/or additions, as described elsewhere herein. In a preferred embodiment, the Wnt polypeptide is Wnt7a. In a particular embodiment, the Wnt polypeptide is a Wnt7a fusion polypeptide comprising N-terminal and/or C-terminal deletions or truncations, and retaining non-canonical Wnt signaling activity. In some embodiments, the Wnt7a polypeptide is a Wnt7a fusion polypeptide that comprises N-terminal and/or C-terminal deletions or truncations, lacks one or more lipidation sites, and retains non-canonical Wnt signaling activity. In preferred embodiments, the fusion polypeptide retains non-canonical Wnt signaling activity.

In particular embodiments, the inventive Wnt fusion polypeptides promote stem cell expansion and promote cell and/or tissue formation, regeneration, maintenance and repair. The inventive Wnt fusion polypeptides are for use in methods of enhancing repair and regeneration in injured and diseased muscle tissue in humans.

Fusion polypeptides may comprise a signal peptide at the N-terminal end of the protein, which co-translationally or post-translationally directs transfer of the protein, truncated Wnt polypeptides or biologically active Wnt polypeptide fragments. Fusion polypeptides may also comprise linkers or spacers, Fc domains, one or more protease cleavage sites, or one or more epitope tags or other sequence for ease of synthesis, purification or production of the polypeptide.

Fusion polypeptide and fusion proteins refer to a polypeptide of the invention that has been covalently linked, either directly or via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the desired activity of the polypeptide. For example, in one embodiment, fusion partners may be selected so as to increase the solubility of the protein, to facilitate production and/or purification of a Wnt polypeptide, and/or to facilitate systemic delivery and/or tissue uptake of Wnts. Fusion polypeptides may be produced by chemical synthetic methods or by chemical linkage between the two moieties or may generally be prepared using other standard techniques. In one embodiment, a Wnt, e.g., Wnt7a, fusion polypeptide comprises a signal peptide and a truncated Wnt polypeptide or a biologically active Wnt polypeptide fragment.

In a particular embodiment, a Wnt, e.g., Wnt7a, fusion polypeptide comprises a signal peptide, a truncated Wnt polypeptide or a biologically active Wnt polypeptide fragment as described elsewhere herein, a protease cleavage site and an epitope tag.

As used herein, the term "signal peptide" refers to a leader sequence ensuring entry into the secretory pathway. For industrial production of a secreted protein, the protein to be produced needs to be secreted efficiently from the host cell or the host organism. The signal peptide may be, e.g., the native signal peptide of the protein to be produced, a heterologous signal peptide, or a hybrid of native and heterologous signal peptide. Numerous signal peptides are used for production of secreted proteins.

Illustrative examples of signal peptides for use in fusion polypeptides of the invention include, but are not limited to: a CD33 signal peptide; an immunoglobulin signal peptide, e.g., an IgGK signal peptide or an IgGµ signal peptide; a growth hormone signal peptide; an erythropoietin signal peptide; an albumin signal peptide; a secreted alkaline phosphatase signal peptide, and a viral signal peptide, e.g., rotovirus VP7 glycoprotein signal peptide.

In particular embodiments, the inventive fusion polypeptides comprise protease cleavage sites and epitope tags to facilitate purification and production of truncated Wnt polypeptides, e.g., Wnt7a. The position of the protease cleavage site is typically between the C-terminus of the Wnt polypeptide and the epitope tag to facilitate removal of heterologous sequences prior to delivery of the Wnt to a cell or tissue.

Illustrative examples of heterologous protease cleavage sites that can be used in fusion proteins of the invention include, but are not limited to: a tobacco etch virus (TEV) protease cleavage site, a heparin cleavage site, a thrombin cleavage site, an enterokinase cleavage site and a Factor Xa cleavage site.

Illustrative examples of epitope tags that can be used in fusion proteins of the invention include, but are not limited to: a HIS6 epitope, a MYC epitope, a FLAG epitope, a V5 epitope, a VSV-G epitope, and an HA epitope.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may also be employed to separate the fusion polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference. The two coding sequences can be fused directly without any linker or by using a flexible polylinker composed of the pentamer Gly-Gly-Gly-Gly-Ser repeated 1 to 3 times. Such linker has been used in constructing single chain antibodies (scFv) by being inserted between VH and VL (Bird et al., 1988, *Science* 242:423-426; Huston et al., 1988, *Proc. Natl. Acad. Sci. U.S.A.* 85:5979-5883). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (Chaudhary et al., 1990, *Proc. Natl. Acad. Sci. U.S.A.* 87:1066-1070) and Lys-Glu-Ser-Gly-Ser-Val-Ser-Ser-Glu-Gln-Leu-Ala-Gln-Phe-Arg-Ser-Leu-Asp (Bird et al., 1988, *Science* 242:423-426).

In general, polypeptides, fusion polypeptides (as well as their encoding polynucleotides), and cells are isolated. An "isolated" polypeptide or polynucleotide is one that is removed from its original environment. For example, an "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated polynucleotide," as used herein, refers to a polynucleotide that has been purified from the sequences which flank it in a naturally-occurring state, e.g., a DNA fragment that has been removed from the sequences that are normally adjacent to the fragment. A polynucleotide is considered to be isolated if, for example, it is cloned into a vector that is not a part of the natural environment. An "isolated cell" refers to a cell that has been obtained from an in vivo tissue or organ and is substantially free of extracellular matrix. Preferably, a polypeptide, polynucleotide, or cell is isolated if it is at least about 60% pure, at least about 70% pure, at least about 80% pure, at least about 90% pure, more preferably at least about 95% pure and most preferably at least about 99% pure.

In particular embodiments, polypeptides may be expressed as a fusion protein in a cell or synthetically and then purified.

In other embodiment, one or more polypeptides may be fused after they after been produced in a cell or synthetically. Generally, according to techniques known in the art and described herein, polypeptides fused after the individual polypeptides in the fusion have been produced may be covalently attached or conjugated, optionally through a wide variety of biocompatible polymers or unrelated chemical moieties. Covalent variants can be prepared by linking functionalities to groups which are found in the amino acid chain or at the N- or C-terminal residue, as is known in the art. In addition, non-peptide polymers (e.g., at least 2 covalently linked non-peptide moieties) include, for example, polyethylene glycol (PEG), polypropylene glycol, copolymers of ethylene glycol and propylene glycol, polyoxyethylated polyols, polyvinyl alcohol, oligosaccharides, dextran, polyvinyl ethyl ether, biodegradable polymers, lipid polymers, chitins, hyaluronic acid and combinations thereof can act as a spacer or linker to fuse two or more polypeptide sequences. Examples of suitable non-peptide polymers include, but are not limited to, PEG, N-(2-hydroxypropyl) methacrylamide (HPMA), polyvinylpyrrolidone (PVP), and poly-ethyleneimine (PEI).

As used herein, the term "obtained from" means that a sample such as, for example, a polynucleotide or polypeptide is isolated from, or derived from, a particular source, such as a recombinant host cell. In another embodiment, the term "obtained from" refers to a cell isolated from or derived from a source such as an in vivo tissue or organ.

In various embodiments, fusions polypeptides comprising a truncated Wnt protein and an Fc domain are provided. The Fc-domain can be fused to the N-terminus or C-terminus of another polypeptide, e.g., a linker polypeptide or a Wnt polypeptide. The Fc-fusion can act as a molecular chaperone: improving protein stability and solubility. The Fc-fusion can also have a major impact on in vivo pharmacokinetic properties: extending half life of the protein by both increasing molecular weight, preventing excretion through renal filtration and by cycling the protein via the neonate Fc receptors present on many cells of the body. Therapeutic antibodies and therapeutic Fc-fusion proteins can act by stimulating or inhibiting an immune response: interaction with the Fcγ receptor on effector cells results in immune function such as antibody-dependent cell-mediated cytotoxicity (ADCC) or complement-dependent cytotoxicity (CDC).

The four human IgG isotypes (1,2,3 and 4) bind the activating Fcγ receptors (FcγRI, FcγRIIa, FcγRIIIa), the inhibitory FcγRIIb receptor, and the first component of complement (Clq) with different affinities, yielding very different effector functions. For example, IgG1 induces a potent ADCC and CDC response whereas IgG2 and IgG4 isoforms have greatly reduced affinities for the positive regulating Fcγ-receptors. Thus, specific IgG-isoform Fc domains can be used when specific effector functions are required. When an immune response is not therapeutically desirable, the IgG4 subtype Fc can be used or other subtype Fc domains engineered to have reduced effector function. Specific CH2 and CH3 domain point mutations that effect immune response are known in the art (Chames 2009).

In particular embodiments, fusion polypeptides comprise a truncated Wnt polypeptide and an Fc-domain. In certain embodiments, the Wnt-Fc-domain fusion polypeptides retain Wnt biological activity but do not induce ADCC and CDC responses. The Fc domain can be obtained from any of the classes of immunoglobulin, IgG, IgA, IgM, IgD and IgE. In some embodiments, the Fc region is a wild-type Fc region. In some embodiments, the Fc region is a mutated Fc region. In some embodiments, the Fc region is truncated at the N-terminal end by 1, 2, 3, 4, 5, 6, 7, 8, 9, or 10 amino acids, (e.g., in the hinge domain).

In particular embodiments, Wnt fusion polypeptides of the invention comprise an N-terminal and/or C-terminal truncated Wnt polypeptide or a biologically active Wnt polypeptide fragment as described elsewhere herein and an Fc-domain. In certain embodiments, Wnt fusion polypeptides of the invention comprise a signal peptide, an N-terminal and/or C-terminal truncated Wnt polypeptide or a biologically active Wnt polypeptide fragment as described elsewhere herein, a protease, and an Fc-domain. In some embodiments, these Wnt fusion polypeptides comprise N-terminal and/or C-terminal deletions or truncations, lack one or more lipidation sites, and retain non-canonical Wnt signaling activity. In preferred embodiments, these Wnt-Fc-domain fusion proteins do not have detectable ADCC or CDC activity. In various related embodiments, these Wnt-Fc-domain fusion proteins retain Wnt biological activity and have improved production, secretion, and/or stability compared to natural Wnt polypeptides.

In additional embodiments, Wnt7a fusion polypeptides of the invention comprise an N-terminal and/or C-terminal truncated Wnt7a polypeptide or a biologically active Wnt7a polypeptide fragment as described elsewhere herein and an Fc-domain. In certain embodiments, Wnt7a fusion polypeptides of the invention comprise a signal peptide, an N-terminal and/or C-terminal truncated Wnt7a polypeptide or a biologically active Wnt7a polypeptide fragment as described elsewhere herein, a protease, and an Fc-domain. In some embodiments, these Wnt7a fusion polypeptides comprise N-terminal and/or C-terminal deletions or truncations, lack one or more lipidation sites, and retain non-canonical Wnt signaling activity. In preferred embodiments, these Wnt7a-Fc-domain fusion proteins do not have detectable ADCC or CDC activity. In various related embodiments, these Wnt7a -Fc-domain fusion proteins retain Wnt biological activity and have improved production, secretion, and/or stability compared to natural Wnt7a polypeptides.

F. Polynucleotides

The present invention also provides isolated polynucleotides that encode Wnt polypeptides of the invention. In various embodiments, the present invention contemplates, in part, Wnt polynucleotides that encode polypeptide truncations or biologically active fragments or Wnt fusion polypeptides that retain Wnt biological activity, and in some embodiments, have increased Wnt signaling activity. In particular embodiments, the inventive Wnt polynucleotides encode Wnt polypeptides that promote stem cell expansion and promote cell and/or tissue formation, regeneration, maintenance and repair.

The inventive Wnt polynucleotides are suitable for clinical scale production of Wnt polypeptides and for use in methods of enhancing repair and regeneration in injured and diseased muscle tissue in humans. In certain embodiments, a Wnt polynucleotide encodes a Wnt polypeptide that lacks one or more of the native amino acids for lipidation of the Wnt polypeptide. In certain particular embodiments, a Wnt polynucleotide encodes a truncated Wnt polypeptide that comprises one or more amino acid deletions or truncations of the N-terminus and/or C-terminus of a Wnt polypeptide or a Wnt fusion polypeptide. In preferred embodiments, the Wnt polynucleotide encodes a Wnt fusion polypeptide or a Wnt7a polypeptide that comprises one or more amino acid deletions or truncations of the N-terminus and/or C-terminus, but retains or has increased Wnt biological activity, such as canonical and non-canonical Wnt signaling activity.

Nucleic acids can be synthesized using protocols known in the art as described in Caruthers et al., 1992, *Methods in Enzymology* 211, 3-19; Thompson et al., International PCT Publication No. WO 99/54459; Wincott et al., 1995, *Nucleic Acids Res.* 23, 2677-2684; Wincott et al., 1997, *Methods Mol. Bio.*, 74, 59-68; Brennan et al., 1998, *Biotechnol Bioeng.*, 61, 33-45; and Brennan, U.S. Pat. No. 6,001,311).

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other (see for example, Usman and McSwiggen, supra; Eckstein et al., International PCT Publication No. WO 92/07065; Usman et al., International PCT Publication No. WO 93/15187; Uhlman & Peyman, supra). There are several examples of modified nucleic acid bases known in the art as summarized by Limbach et al., (1994, *Nucleic Acids Res.* 22, 2183-2196).

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides, and the like. Such segments may be naturally isolated, recombinant, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide of the invention or a portion thereof) or may comprise a variant, or a biological functional equivalent of such a sequence. Polynucleotide variants may contain one or more substitutions, additions, deletions and/or insertions, as described elsewhere herein, preferably such that the variant encodes a polypeptide that lacks canonical lipidation sites, but retains, and in some embodiments, has increased biological activity, such as pathway signaling activity.

Also included are polynucleotides that hybridize to polynucleotides that encode a polypeptide of the invention. To hybridize under "stringent conditions" describes hybridization protocols in which nucleotide sequences at least 60% identical to each other remain hybridized. High stringency hybridization conditions are conditions that enable a probe, primer or oligonucleotide to hybridize only to its target sequence. Stringent conditions are sequence-dependent and will differ. Moderately stringent conditions are conditions that use washing solutions and hybridization conditions that are less stringent (Sambrook, 1989) than those for high stringency, such that a polynucleotide will hybridize to the entire, fragments, derivatives or analogs of nucleic acids of the present invention. Moderate stringency conditions are described in (Ausubel et al., 1987; Kriegler, 1990). Low stringent conditions are conditions that use washing solutions and hybridization conditions that are less stringent than those for moderate stringency (Sambrook, 1989), such that a polynucleotide will hybridize to the entire, fragments, derivatives or analogs of nucleic acids of the present invention. Conditions of low stringency, such as those for cross-species hybridizations are described in (Ausubel et al., 1987; Kriegler, 1990; Shilo and Weinberg, 1981).

In additional embodiments, the invention provides isolated polynucleotides comprising various lengths of contiguous stretches of sequence identical to or complementary to a polynucleotide encoding a polypeptide or fusion polypeptide as described herein. For example, polynucleotides provided by this invention encode at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, or 129 contiguous amino acid residues of a polypeptide of the invention. It will be appreciated by those of ordinary skill in the art that, as a result of the degeneracy of the genetic code, there are many nucleotide sequences that encode a polypeptide as described herein, including polynucleotides that are optimized for human and/or primate codon selection. Further, alleles of the genes comprising the polynucleotide sequences provided herein may also be used.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or mammalian cell systems.

The "control elements" or "regulatory sequences" present in an expression vector are those non-translated regions of the vector—enhancers, promoters, 5' and 3' untranslated regions—which interact with host cellular proteins to carry out transcription and translation. The vector components generally include, but are not limited to, one or more of the following: a signal sequence, an origin of replication, one or more marker genes, an enhancer element, a promoter that is recognized by the host organism, and a transcription termination sequence. Specific initiation signals may also be used to achieve more efficient translation of sequences encoding a polypeptide of interest.

Host cell strains may be chosen for their ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Illustrative mammalian host cells such as CHO cells, COS cells, CV1 cells, mouse L cells, mouse LSL cells, HeLa cells, MDCK cells, HT1080 cells, BHK-21 cells, HEK293 cells, NIH-3T3 cells, LM cells, YI cells, NSO and SP2/0 mouse hybridoma cells and the like, Namalwa cells, RPMI-8226 cells, Vero cells, WI-38 cells, MRC-5cells or other immortalized and/or transformed cells, which have specific cellular machinery and characteristic mechanisms for such post-translational activities, may be chosen to ensure the high expression and correct modification and processing of the foreign protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

G. Compositions

In various embodiments, the invention contemplates, in part, novel compositions of Wnt polypeptides and polynucleotides encoding the same. As discussed elsewhere herein, one of the major limitations or obstacles to the therapeutic use of Wnts is their low solubility, which makes them impracticable to generate on a clinical scale. The inventors have engineered novel Wnt polypeptides that have increased solubility, stability, production, systemic delivery, and tissue uptake, and that retain or have increased Wnt biological activity compared to naturally occurring Wnts. In particular embodiments, the invention provides aqueous formulations of soluble Wnt polypeptides to promote stem cell expansion and muscle hypertrophy, and promote cell and/or tissue formation, regeneration, maintenance and repair.

The compositions of the invention may comprise one or more polypeptides, polynucleotides, vectors comprising same, etc., as described herein, and one or more pharmaceutically-acceptable salts, carriers, diluents, excipients, and/or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins, polypeptides, small molecules or various pharmaceutically-active agents. There is virtually no limit to other components that may also be included in the compositions, provided that the additional agents do not adversely affect the therapeutic potential of the Wnt composition, such as the ability of the composition to promote muscle hypertrophy and promote tissue formation, regeneration, maintenance and repair.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Other illustrative examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen- free water; (17) isotonic saline; (18) Ringer's solution; (19) ethyl alcohol; (20) pH buffered solutions; (21) polyesters, polycarbonates and/or polyanhydrides; (22) a pharmaceutically acceptable cell culture medium; and (23) other nontoxic compatible substances employed in pharmaceutical formulations.

Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," *Pharm Res.* 8(3): 285-91 (1991); Kendrick et al., "Physical stabilization of proteins in aqueous solution," in: RATIONAL DESIGN OF STABLE PROTEIN FORMULATIONS : THEORY AND PRACTICE, Carpenter and Manning, eds. *Pharmaceutical Biotechnology.* 13: 61-84 (2002), and Randolph et al., "Surfactant-protein interactions," *Pharm Biotechnol.* 13: 159-75 (2002), each of which is herein incorporated by reference in its entirety, particularly in parts pertinent to excipients and processes of the same for formulations in accordance with the current invention, especially as to protein pharmaceutical products and processes for veterinary and/or human medical uses.

In certain embodiments, a composition of the present invention comprises an excipient selected from the group consisting of cyclodextrins and derivatives, celluloses, liposomes, micelle forming agents, e.g., bile acids, and polymeric carriers, e.g., polyesters and polyanhydrides.

In particular embodiments, compositions, particularly pharmaceutical protein compositions, comprise a protein and a solvent, and further comprising one or more pharmaceutically acceptable surfactants, preferably one or more of polysorbate 20, polysorbate 80, other fatty acid esters of sorbitan, polyethoxylates, and poloxamer 188, particularly preferably polysorbate 20 or polysorbate 80, preferably approximately 0.001 to 0.1% polysorbate 20 or polysorbate 80, very preferably approximately 0.002 to 0.02% polysorbate 20 or polysorbate 80, especially 0.002 to 0.02% polysorbate 20 or polysorbate 80. Many other such surfactants may be employed in embodiments of the invention. Included among such others are the following: Tween 20, including but not limited to from about 0.0005% or about 0.01% Tween 20; sodium cholate, including but not limited to from about 0.001% to about 0.01% sodium cholate; sodium glycholate, including but not limited to from about 0.001% to about 0.01% sodium glycholate; sodium deoxycholate, including but not limited to from about 0.001% to 0.01% sodium deoxycholate; sodium glycodeoxycholate, including but not limited to from about 0.001% to about 0.01% sodium glycodeoxycholate; CHAPS, including but not limited to from about 0.001% to about 0.01% CHAPS; CHAPSO, including but not limited to from about 0.001% to about 0.01% CHAPSO; Emphigen BB, including but not limited to from about 0.001% to about 0.01% Emphigen BB; SDS, including but not limited to from about 0.001% to about 0.01% SDS; Mega-8, including but not limited to from about 0.001% to about 0.01% Mega-8; Genepol C-100, including but not limited to from about 0.001% to about 0.01% Genepol C-100; Brij 35, including but not limited to from about 0.001% to about 0.01% Brij 35; Pluronic F-68, including but not limited to from about 0.001% to about 0.01% Pluronic F-68; Pluronic F-127, including but not limited to from about 0.001% to about 0.01% Pluronic F-127; Zwittergent 3-12, including but not limited to from about 0.001% to about 0.01% Zwittergent 3-12; PEG-8000, including but not limited to from about 0.001% to about 0.01% PEG-8000; PEG-4000, including but not limited to from about 0.001% to about 0.01% PEG-4000; HPCD, including but not limited to from about 0.001% to about 0.1% HPCD; and Triton X-100, including but not limited to from about 0.001% to about 0.01% Triton X-100.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, gfiitaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

Additional methods of formulating compositions known to the skilled artisan, for example, as described in the *Physicians Desk Reference*, 62nd edition. Oradell, N.J.: Medical Economics Co., 2008; Goodman & Gilman's *The Pharmacological Basis of Therapeutics*, Eleventh Edition. McGraw-Hill, 2005; *Remington: The Science and Practice of Pharmacy*, 20th Edition. Baltimore, Md.: Lippincott Williams & Wilkins, 2000; and *The Merck Index*, Fourteenth Edition. Whitehouse Station, N.J.: Merck Research Laboratories, 2006; each of which is hereby incorporated by reference in relevant parts.

In certain circumstances it will be desirable to deliver the compositions disclosed herein parenterally. As used herein, the phrases "parenteral administration" and "administered parenterally" refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. See, for example, in U.S. Pat. Nos. 5,543,158; 5,641,515 and 5,399,363 (each specifically incorporated herein by reference in its entirety).

In certain embodiments, the compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212(each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

H. Methods of Delivery

In one embodiment, cells, e.g., stem cells such as satellite stem cells, are contacted with a composition comprising one or more inventive Wnt polypeptides and/or polynucleotides. It is contemplated that the cells of the invention may be contacted in vitro, ex vivo, or in vivo. In other embodiments, the Wnt compositions of the invention are administered to a subject.

The compositions of the invention can be administered (as proteins/polypeptides, or in the context of expression vectors for gene therapy) directly to the subject or delivered ex vivo, to cells derived from the subject (e.g., as in ex vivo gene therapy). Direct in vivo delivery of the compositions will generally be accomplished by parenteral injection, e.g., subcutaneously, intraperitoneally, intravenously myocardial, intratumoral, peritumoral, or to the interstitial space of a tissue. Other modes of administration include oral and pulmonary administration, suppositories, and transdermal applications, needles, and gene guns or hyposprays.

The compositions of the invention may also be administered by direct injection into a tissue, such as a muscle. In some embodiments of the invention, a composition of the invention is administered by directly injecting the composition into muscle tissue to prevent a loss of muscle in the injected muscle or to promote regeneration or repair of the injected muscle, for example by promoting expansion of the muscle cells or hypertrophy of the injected muscle.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, direct microinjection of the DNA into nuclei, and viral-mediated, such as adenovirus (and adeno-associated virus) or alphavirus, all well known in the art.

In certain embodiments, it will be preferred to deliver one or more modified Wnts using a viral vector or other in vivo polynucleotide delivery technique. In a preferred embodiment, the viral vector is a non-integrating vector or a transposon-based vector. This may be achieved using any of a variety of well-known approaches, such as vectors including adenovirus, retrovirus, lentivirus, adeno-associated virus vectors (AAV), or the use of other viral vectors as expression constructs (including without limitation vaccinia virus, polioviruses and herpes viruses).

Non-viral methods may also be employed for administering the polynucleotides of the invention. In one embodiment, a polynucleotide may be administered directly to a cell via microinjection or a tissue via injection, such as by using techniques described in Dubensky et al., (1984) or Benvenisty & Reshef (1986). It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). In another embodiment, polynucleotides are administered to cells via electroporation.

I. Methods of Treatment

The Wnt polypeptides, including, but not limited to, truncated Wnt7a polypeptides, biologically active Wnt7a polypeptides, Wnt7a fusion polypeptides, and compositions of the invention are useful for various therapeutic applications. For example, the compositions and methods described herein are useful for promoting tissue formation, regeneration, repair or maintenance in a subject in need thereof.

Some relevant therapeutic applications for the Wnt compositions of the invention include situations where there is a need to prevent muscle loss or regenerate lost or damaged muscle tissue by increasing muscle size, volume or strength. Such situations may include, for example, after chemotherapy or radiation therapy, after muscle injury, or in the treatment or management of diseases and conditions affecting muscle. In certain embodiments, the disease or condition affecting muscle may include urinary incontinence, a wasting disease (e.g., cachexia, which may be associated with an illness such as cancer or AIDS), muscular attenuation or atrophy, or a muscle degenerative disease. Muscular attenuation and atrophy may be associated with, for example, sarcopenia (including age-related sarcopenia), ICU-induced weakness, disuse of muscle (for example disuse of muscle due to coma paralysis, injury, or immobilization), surgery-induced weakness (e.g., following hip or knee replacement), or a muscle degenerative disease (e.g., muscular dystrophies). This list is not exhaustive.

In certain embodiments, the polypeptides and compositions of the invention may be used to stimulate symmetrical expansion of muscle satellite cells, thereby increasing the proportion of resident satellite cells, or committed precursor cells, in a muscle tissue. The polypeptides and compositions may also be used to promote muscle hypertrophy, such as by increasing the size of individual muscle fibers. The polypeptides and compositions of the invention may thus increase both the number of muscle cells and the size of muscle cells, and as a result may be useful for example, to replace damaged or defective tissue, or to prevent muscle atrophy or loss of muscle mass, in particular, in relation to diseases and disorders affecting muscle, such as muscular dystrophy, neuromuscular and neurodegenerative diseases, muscle wasting diseases and conditions, atrophy, cardiovascular disease, stroke, heart failure, myocardial infarction, cancer, HIV infection, AIDS, and the like.

In additional embodiments, the compositions and methods are useful for repairing or regenerating dysfunctional skeletal muscle, for instance, in subjects having muscle degenerative diseases. The subject can be suspected of having, or be at risk of at having skeletal muscle damage, degeneration or atrophy. The skeletal muscle damage may be disease related or non-disease related. The human subject may have or be at risk of having muscle degeneration or muscle wasting. The muscle degeneration or muscle wasting may be caused in whole or in part by a disease, for example aids, cancer, a muscular degenerative disease, or a combination thereof Illustrative examples of muscular dystrophies include, but are not limited to Duchenne muscular dystrophy (DMD), Becker muscular dystrophy (BMD), myotonic dystrophy (also known as Steinert's disease), limb-girdle muscular dystrophies, facioscapulohumeral muscular dystrophy (FSH), congenital muscular dystrophies, oculopharyngeal muscular dystrophy (OPMD), distal muscular dystrophies and Emery-Dreifuss muscular dystrophy. See, e.g., Hoffman et al., *N. Engl. J. Med.,* 318.1363-1368 (1988); Bonnemann, C. G. et al., *Curr. Opin. Ped.,* 8: 569-582 (1996); Worton, R., *Science,* 270: 755-756 (1995); Funakoshi, M. et al., *Neuromuscul. Discord.,* 9 (2): 108-114 (1999); Lim, L. E. and Campbell, K. P., *Cure. Opin. Neurol.,* 11 (5): 443-452 (1998); Voit, T., *Brain Dev.,* 20 (2): 65-74 (1998); Brown, R. H., *Annu. Rev. Med.,* 48: 457-466 (1997); Fisher, J. and Upadhyaya, M., *Neuromuscul. Disord.,* 7 (1): 55-62 (1997).

In certain embodiments, a use of a composition as described herein for the manufacture of a medicament for promoting muscle formation, maintenance, repair, or regeneration of muscle in a subject in need thereof is provided. In particular embodiments, a composition as described herein is provided for use in the manufacture of a medicament for promoting muscle formation, maintenance, repair, or regeneration of muscle in a subject in need thereof is provided. The Wnt polypeptides may be used for preventing or treating muscle atrophy, such as by increasing the size or number of myofibers.

The composition may be administered in an effective amount, such as a therapeutically effective amount. For in vivo treatment of human and non-human subjects, the subject is usually administered a composition comprising an effective amount of one or more modified Wnt polypeptides of the present invention. An "effective amount" refers to an amount effective, at dosages and for periods of time necessary, to achieve the desired therapeutic or prophylactic result.

A "therapeutically effective amount" of a Wnt polypeptide of the invention, or a composition comprising the same, may vary according to factors such as the disease state, age, sex, and weight of the individual, and the ability of a Wnt polypeptide to elicit a desired response in the individual. A therapeutically effective amount is also one in which any toxic or detrimental effects of a Wnt polypeptide are outweighed by the therapeutically beneficial effects. The term "therapeutically effective amount" refers to an amount of a Wnt polypeptide or composition comprising the same that is effective to "treat" a disease or disorder in a mammal (e.g., a patient).

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

In various embodiments, the invention provides for methods of increasing the division symmetry of adult stem cells, such as satellite stem cells compared to untreated stem cell populations. The methods disclosed herein are further capable of promoting symmetrical stem cell division without altering the rate of stem cell division and can promote the survival of a population of stem cells. The methods may be performed in vitro, ex vivo, or in vivo.

In particular embodiments, compositions comprising one or more modified Wnt polypeptides and/or polynucleotides are administered in vivo to a subject in need thereof. As used herein, the term "subject" includes, but is not limited to, a mammal, including, e.g., a human, non-human primate (e.g., baboon, orangutan, monkey), mouse, pig, cow, goat, dog, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate. In preferred embodiments, the subject is human. Subjects in need of treatment for a disease or condition include subjects exhibiting symptoms of such disease or condition, such as those having a disease or condition, as well as those at risk of having a disease or condition.

In particular embodiments, a method for expanding a population of satellite stem cells in vivo, ex vivo, or in vitro comprising contacting the stem cells with an effective amount of a composition comprising a truncated Wnt7a polypeptide, a biologically active Wnt7a polypeptide, a Wnt7a fusion polypeptide, or ortholog, paralog, or homolog thereof, that binds to and activates Fzd7, or a polynucleotide encoding such a Wnt7a polypeptide.

Without being bound to any particular theory, it is believed that increasing the number of satellite cells in a tissue, provides enhanced regeneration potential of the tissue.

In particular embodiments, stem cells are isolated or maintained, and expanded ex vivo or in vitro and subsequently administered to a subject in need thereof. For example, stem cells can be cultured and expanded ex vivo or in vitro and contacted with an effective amount of a Wnt composition of the invention and then administered to a patient as a therapeutic stem cell composition according to methods known to skilled persons. In certain embodiments, the expanded stem cell population is administered to the patient in combination with a therapeutic Wnt composition.

The methods of promoting stem cell expansion can be used to stimulate the ex vivo or in vitro expansion of stem cells and thereby provide a population of cells suitable for transplantation or administration to a subject in need thereof.

In some forms of urinary continence, the dysfunctional muscle can be treated with a composition or method of the invention, for example, by direct protein injection into the muscle. Thus, in one embodiment, the method is useful for treating urinary incontinence.

In further embodiments, damaged or dysfunctional muscle tissue may be cardiac muscle. For instance, the damaged muscle tissue may be cardiac muscle damaged by a cardiovascular event such as myocardial infarct, or heart failure, where the target stem cell would be a cardiac stem cell. In accordance with another aspect of the present invention, there is provided a method of promoting cardiac stem cell expansion or cardiac muscle hypertrophy in a mammal comprising administering to the mammal an effective amount of a composition as described herein.

Further, in addition to using the stem cells in transplants, stem cells, or compositions comprising stem cells may be used as a research tool and/or as part of a diagnostic assay or kit. Without wishing to be limiting a kit may comprise muscle stem cells, one or more modified Wnt polypeptides, cell culture or growth medium, cell cryopreservation medium, one or more pharmaceutically acceptable delivery media, one or more modified Wnt polynucleotide sequences or genetic constructs, one or more devices for implantation or delivery of cells to a subject in need thereof, instructions for using, delivering, implanting, culturing, cryopreserving or any combination thereof the cells as described herein.

Indicators of cell expansion and/or muscle hypertrophy may be monitored qualitatively or quantitatively and include, for example, changes in gross morphology, total cell number, histology, histochemistry or immunohistochemistry, or the presence, absence or relative levels of specific cellular markers. The presence, absence or relative levels of cellular markers can be analyzed by, for example, histochemical techniques, immunological techniques, electrophoresis, Western blot analysis, FACS analysis, flow cytometry and the like. Alternatively the presence of mRNA expressed from the gene encoding the cellular marker protein can be detected, for example, using PCR techniques, Northern blot analysis, the use of suitable oligonucleotide probes and the like.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Design of Truncated Wnt Proteins

The Wnt family proteins are 300-400 amino acids in length and contain several post translational modifications including glycosylations and lipidations. The lipidation of Wnt proteins poses a challenge for large scale recombinant production, formulation and potential therapeutic use. It has generally been accepted that the lipidation of Wnts is required for their signaling activity, although most studies in this area have only been completed with a single isoform (Wnt3a) and by using a single Wnt signaling pathway (the canonical activation of β-catenin-dependent transcriptional activation) (Willert et at 2003) (Takada 2006). FIG. 1 shows the potential lipidation sites of a Cysteine (Cys 73 in Wnt7a) and a Serine (Ser 206 in Wnt7a) are conserved between Wnt family members. The signaling activity, particularly non-canonical signaling, of Wnt7a can be maintained even when the proposed sites of lipidation are removed by mutagenesis to alanine residues. The construction of single or double alanine replacement at positions C73A and/or S206A resulted in proteins that gave moderately improved production, when expressed in mammalian cell tissue culture, and formulation characteristics while retaining in vitro and in vivo activity. Wnt proteins were truncated to an active domain that retained activity. The truncated Wnts enabled higher levels of production and were delipidated—aiding formulation and stability in aqueous solution.

Figure 2A:
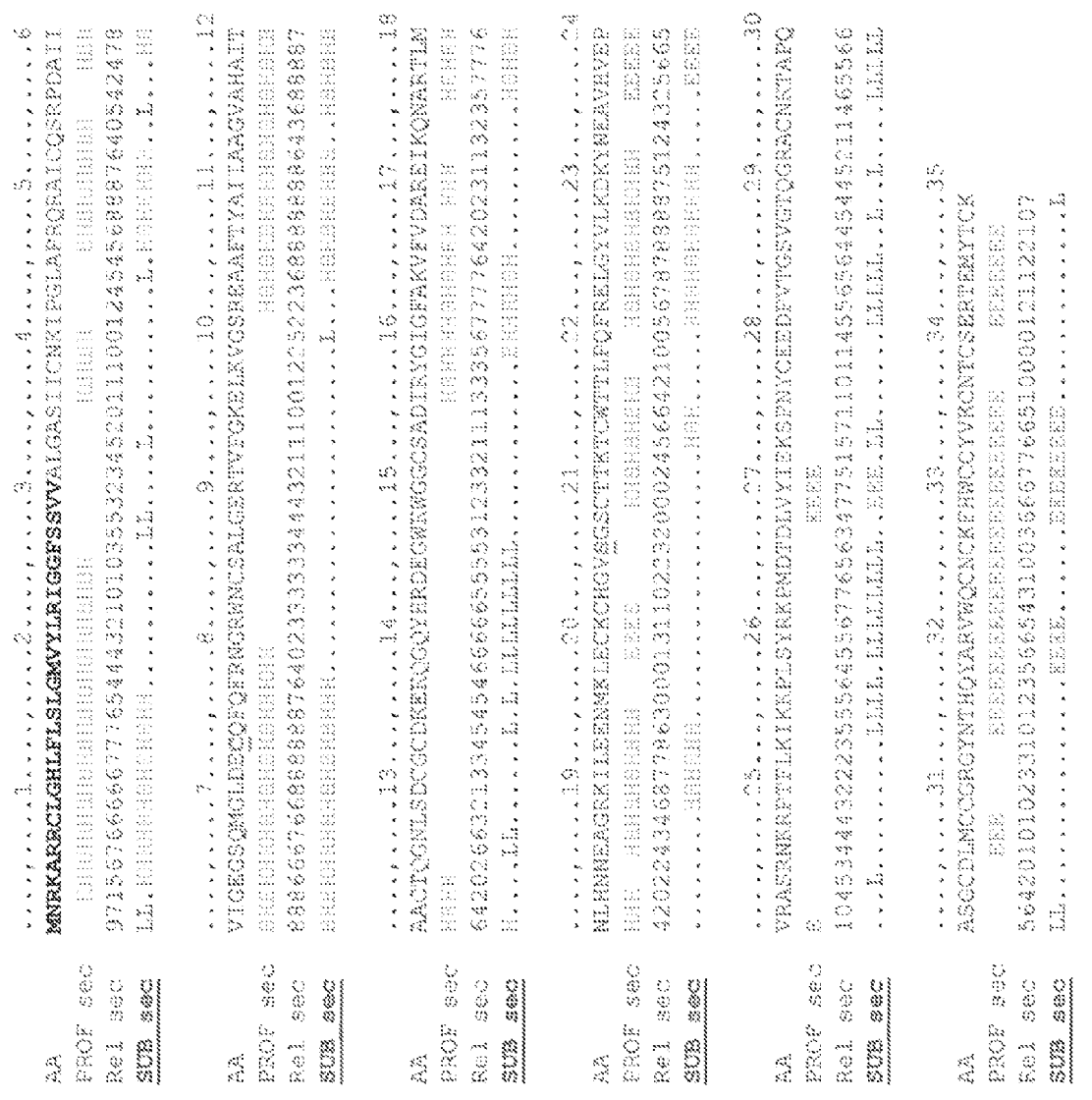

The Wnt7a amino acid sequence was analyzed using the ProteinPredict software program, which evaluates secondary structure prediction and potential solvent accessability, to build a predicted model of structural motifs. FIG. 2A shows the prediction for the human Wnt7a sequence and highlights two structural domains: an N-terminal domain comprising a majority of a-helix secondary structure and a C-terminal domain comprising a majority of protein sheet secondary structure. The transition from the N-terminal domain to the C-terminal domain occurs approximately between residues 235 and 265.

Figure 2B:
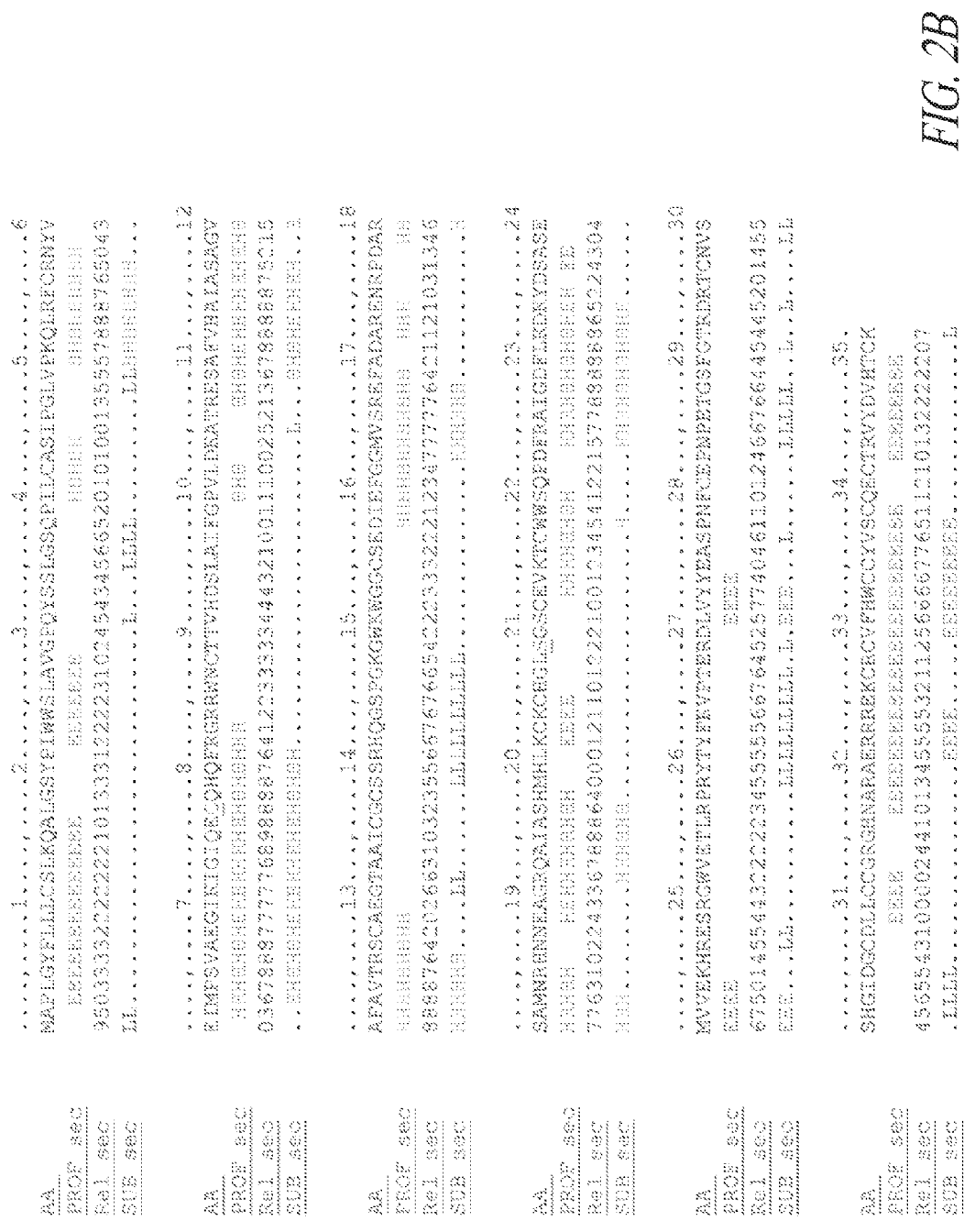

The ProteinPredict secondary structure prediction program was also used to characterize the canonical human Wnt3a protein. FIG. 2B shows the potential domain structure of Wnt3a, which is similar to that of Wnt7a, with an N-terminal α-helix structure and C-terminal protein sheet structure. In human Wnt3a, the transition between the two domains occurs at approximately residues 237-270. The predicted C-terminal domain does not contain the potential lipidation sites, as previously mapped. Expression cassettes of these domains were constructed to assess if Wnt signaling activity could be retained within a single region of the Wnt protein while minimizing the requirement for lipid post-translational modification. Such proteins may be advantageous for protein production, formulation, and ultimate therapeutic and industrial use.

Several expression constructs were designed to evaluate the potential for constructing an active Wnt signaling molecule while truncating the amino acid sequence to a discrete, un-lipidated domain. A schematic highlighting the various Wnt7a protein forms is shown in FIG. 3. The alanine substitutions of the potential lipidation sites are schematically displayed (Wnt7a C73A and/or 5206A). Several truncated Wnt constructs were placed in bacterial expression cassettes as described below. The majority of protein forms were constructed for production in mammalian expression systems. For these forms, the endogenous Wnt7a secretion signal peptide was replaced with an exogenous signal peptide such as the IgG-Kappa, CD33 or IL2 signal peptides. Signal peptides can potentially improve the effective secretion of recombinant proteins from mammalian expression systems.

Truncations resulting in two different C-terminal domain Wnts were expressed in mammalian tissue culture and tested: Wnt7a aa235-349 and Wnt7a aa264-349. Wnt7a aa264-349 contains a more defined structural domain, as assessed through the prediction, while keeping an even number of cysteine residues (12). The Wnt7a aa264-349 protein was expressed as a fusion protein to the human IgG1Fc domain with or without the inclusion of a Tobacco Etch Virus (TEV) protease recognition site in a linker region between the Wnt fragment and the Fc domain. This system allowed for efficient expression and secretion of the fusion protein followed by proteolytic cleavage of the Wnt7a aa264-349 protein at the specific TEV recognition site. Affinity chromatographic methods were used to clear the resulting digested protein of the Fc-domain, the protease, and any residual, undigested fusion protein—resulting in a purified preparation of the small molecular weight Wnt 264-349 amino acid protein fragment. Wnt7a aa264-349 has a calculated molecular weight of 11 kDa and an observed molecular weight of approximately 17 kDa, the difference most likely due to posttranslational glycosylation.

In the present example, the Wnt-Fc-fusion proteins contain the following point mutations specific to the Fc region: E233P/L234V/L235A/AG236+A327G/A330S/P331S. These mutations correspond to various positions in Wnt fusion proteins, depending on the construct. In addition, these mutations reduce the affinity of the IgG1 Fc-domain for the Fcγ-receptors and therefore limit the potential for any undesirable immune activation by the fusion protein. Sequence descriptions and corresponding sequence identification for all examples are shown in FIG. 3 and the accompanying sequence listing file.

Example 2

Construction of Truncated Wnts

Truncated Wnt polypeptides and vectors comprising the same were constructed according to the following methods.
Vector Construction for Bacterial Expression of Wnts A pET29a(+) expression vector comprising a Wnt7a C-terminal domain was constructed using the wild type human Wnt7a as a template for PCR. The forward primer 5'-GCATCATATGGCCGTTCACGTGGAGCCTG-3' (SEQ ID NO: 24) and reverse primer 5'-GCATGCGGCCGCT-CACTTGCACGTGTACATCTCC-3' (SEQ ID NO: 25) were used to amplify the polynucleotide sequence encoding amino acids 235-349 of Wnt7a. The PCR product was digested with NdeI and Not 1 restriction enzymes and ligated into a pET29a(+) vector between the NdeI and Not 1 sites. The truncated Wnt7a construct was prepared using the PfuUltraII® polymerase.

A pET28a(+) expression vector comprising a Wnt7a C-terminal domain was constructed using the wild type human Wnt7a as a template for PCR. The forward primer 5'-GCATCCATGGCCGTTCACGTGGAGCCTG-3' (SEQ ID NO: 26) and reverse primer 5'-GCATGCGGCCGCT-CACTTGCACGTGTACATCTCC-3' (SEQ ID NO: 25) were used to amplify the polynucleotide sequence encoding amino acids 235-349 of Wnt7a. The PCR product was digested with NcoI and Not 1 restriction enzymes and ligated into a pET28a(+) vector between the NcoI and Not 1 sites. The truncated Wnt7a construct was prepared using the PfuUltraII® polymerase.

Example 3

Construction of Wnt Fusion Polypeptides

Wnt fusion polypeptides and vectors comprising the same were constructed according to the following methods.
Vector Construction for Mammalian Expression of Wnts A pcDNA3.1(+) expression vector comprising a CD33 signal peptide fused to a human Wnt7a C-terminal domain fused to a TEV protease site and a 6HIS tag was constructed. The polynucleotide sequence for CD33 (5'-ATGCCCCT-GCTGCTGCTCCTCCCTCTGCTGTGGGCTG-GCGCTCTGGCCATGGAT-3' (SEQ ID NO: 27)) encodes the amino acid sequence MPLLLLLPLLWAGALAMD (SEQ ID NO: 28)) and was fused to the polynucleotide sequence encoding amino acids 235-349 of human Wnt7a. The resulting construct was cloned into a pcDNA3.1(+) expression vector comprising a TEV protease site and 6HIS epitope sequence. The amino acid sequence of the fusion polypeptide is set forth in SEQ ID NO: 10).

A pcDNA3.1(+) expression vector comprising an IgGκ signal peptide fused to a Wnt7a C-terminal domain fused to a TEV protease site and a FLAG tag was constructed. The polynucleotide sequence for IgGκ (5'-ATGGAGACAGA-CACACTCCTGCTATGGGTACTGCTGCTCTGGGTTC-CAGGTT CCACTGGTGAC -3' (SEQ ID NO: 29)) encodes the amino acid sequence METDTLLLWVLLLWVPG-STGD (SEQ ID NO: 30)) and was fused to the polynucleotide sequence encoding amino acids 235-349 of human Wnt7a. The resulting construct was cloned into a pcDNA3.1 (+) expression vector comprising a TEV protease site and FLAG epitope sequence. The amino acid sequence of the fusion polypeptide is set forth in SEQ ID NO: 13).

The following Wnt7a constructs were also made and cloned into mammalian cell expression vectors such as pcDNA3.1(+): Wnt7a aa31-349, Wnt7a aa 235-349 and/or Wnt7a aa 264-349 of human Wnt7a combined with either CD33 secretion signal peptide (5' ATGCCCCTGCTGCT-GCTCCTCCCTCTGCTGTGGGCTGGCG CTCTGGC-CATGGAT-3' (SEQ ID NO: 27)) encoding the amino acid sequence MPLLLLLPLLWAGALAMD (SEQ ID NO: 28)) or an IgG Kappa chain secretion signal peptide (5'-ATG-GAGACAGACACACTCCTGCTATGGGTACTG CTGCTCTGGGTTCCAGGTTCCACTGGTGAC -3' (SEQ ID NO: 29)) encoding the amino acid sequence MET-DTLLLWVLLLWVPGSTGD (SEQ ID NO: 30)). These fusion proteins were constructed in the absence of any other tag or fusion to create the polypeptide sequences outlined on SEQ ID NOs: 33, 34, 35, and 36. Further the same truncated Wnt/ signal peptide fusions were constructed with the addition of a C-terminal IgG-Fc domain. The particular FC-fusion domain used here was human IgG1 with the following mutations to reduce effector cell function E233P/L234V/L235A/AG236 +A327G/A330S/P331S. The truncated Wnt7a-Fc-fusion polypeptide sequences for these constructs are set forth in SEQ ID NOs: 37, 38, 39, and 40.

Additional truncated forms of Wnt7a were constructed using the CD33 and IgG Kappa chain exogenous secretion signal peptides in combination with Fc-fusions but including a protease recognition site between the Wnt and Fc domains.

These constructs capitalize on the improved expression and purification of Fc-fusion proteins and ultimately remove the Fc domain from the Wnt polypeptide. The truncated Wnt7a-Fc-fusion polypeptide sequences for these constructs are set forth in SEQ ID NOs: 41, 42, 43, and 44.

Example 4

WNT Protein Expression and Purification

The effective, scaled production of active Wnt protein has been hindered by the combination of relatively low Wnt protein expression and secretion in recombinant systems coupled with challenges of formulation for these lipidated proteins. Active Wnts have been effectively made at small scale in mammalian systems and purified in the presence of detergents and liposomes that effectively hold the lipidated Wnt in an active conformation (Willert 2008) (Morrel 2008). These studies have been completed for canonical Wnt proteins and to a lesser extent for non-canonical Wnt proteins. However, the use of liposome formulation is challenging for therapeutic manufacture and the use of detergents such as 3-[(3-cholamidopropyl) dimethylammonio]-1-propanesulfonate (CHAPS) are not necessarily applicable to therapeutic administration. Full length Wnt proteins comprising exogenous signal peptides were made, with the hope that the exogenous signal peptides would improve secretion efficiency. In addition, secreted and purified full-length Wnts with exogenous signal peptides and Fc-domain fusions were expressed. Expressed and purified Wnt truncations as described in Examples 1-3 were also made, again comparing exogenous signal peptides and the use of Fc-fusion proteins.

For the mammalian cell production, 293F suspension culture was prepared at a cell density of $10^6$ viable cells per ml in 293 Freestyle serum-free media. Cells were transiently transfected by liposomal transfection of 1 µg of WNT expression vector per ml of culture in Opti-MEM I media with 1 µl of Mims TransIT Pro reagent per µg of vector DNA. The DNA:liposomal complex was allowed to form for twenty-five minutes prior to addition to the 293F suspension culture. The transfected cells were incubated at 37° C., 8% $CO_2$ on an orbital shaker at 130 rpm for 72 hours. The conditioned media was harvested by two rounds of centrifugation, one at 300×g and one at 3000 x g, followed by sterile filtration. Wnt protein in conditioned media was quantified by western blot with specific antibodies to either WNT or the Fc domain of human IgG. Normal WNT yields in conditioned media ranged from 0.9 to 10 µg per milliliter depending upon the construct transfected. Harvested media was concentrated fivefold by tangential flow filtration using parallel Sartorius Vivaflow 200 devices run at a constant pressure of 2.5 bar. The final media was sterilized through a 0.2 micron Millipore Opticap XL 150 capsule and moved to protein purification procedures.

Wild-type Wnt7a and delipidated Wnt proteins in the absence of Fc-fusion were purified using cleared conditioned media loaded onto a HiTrap Blue HP column (5 mL). Columns were washed with 25 mL of 20 mM Tris-HCl pH 7.5, 1% (w/v) CHAPS followed by elution with 25 mL of 20 mM Tris-HCl pH 7.5, 1% (w/v) CHAPS, 1.5 M KCl. Wnt7a in elution fractions detected with anti-Wnt7a Western blotting was pooled and further purified on 2 mL Sepharose 4 Fast Flow coupled with anti-Wnt7a antibody. Loading was performed at 0.2 mL/min followed by washing with 20 mL PBS, 1% CHAPS. Bound Wnt7a was eluted with 0.1 M glycine-HCl pH 2.5, 150 mM NaCl, 1% CHAPS. Eluates were collected in 1-mL fractions which were pre-filled with 50 µL 1 M Tris-HCl pH 9.0. Purity of Wnt7a in elution fractions was analyzed with SDS-PAGE and detected with silver staining Wnt7a variants fused to human Fc were purified using cleared conditioned media loaded to a HiTrap rProtein A FF column (5 mL). Columns were washed with 40 mL PBS, 1% CHAPS. Bound fusion protein was eluted with 0.1 M glycine-HCl pH 2.5, 150 mM NaCl, 1% CHAPS. Eluates were collected in 5-mL fractions which were pre-filled with 0.25 mL 1 M Tris-HCl pH 9.0. Purity of Wnt7a in elution fractions was analyzed with SDS-PAGE and detected with Coomassie staining Fractions containing Wnt7a were pooled and concentrated using an Amicon Ultra-15 concentrator to 2 mL. Concentrated Wnt7a was finally buffer-exchanged using a PD-10 desalting column (GE Healthcare Life Sciences) equilibrated with PBS, 1% CHAPS. Protein concentration was determined using a Bradford assay with BSA as a standard.

Figure 5:
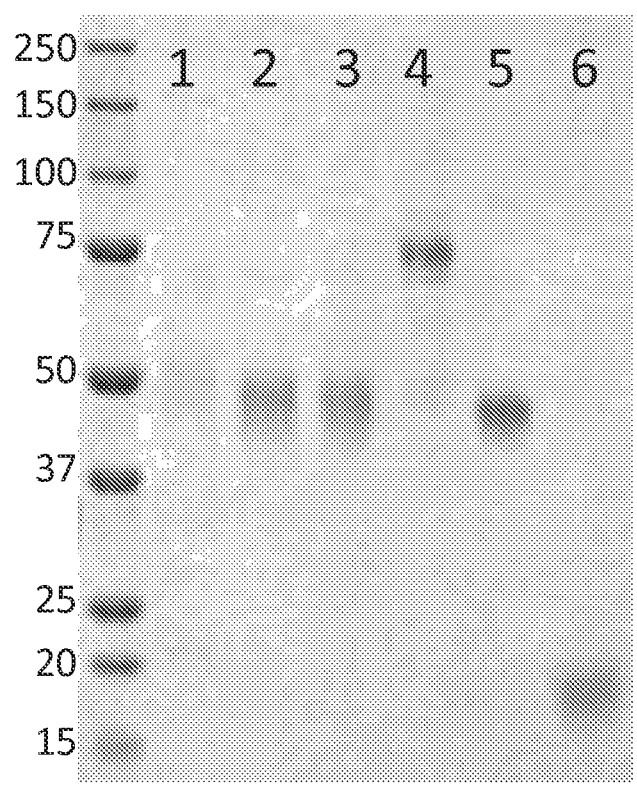
FIG. 5 shows a Coomassie-stained SDS-PAGE gel of various purified Wnt7a protein forms. Proteins were expressed and purified as described in Example 4. 500 ng of each Wnt7a protein was loaded in each lane: 1) commercially available Wnt7a from R&D systems; 2) full length Wnt7a expressed and secreted with endogenous signal sequence replaced with the IgG Kappa-chain signal sequence; 3) a mutated, delipidated Wnt7a with the IgG Kappa signal sequence used; 4) delipidated Wnt7a expressed and purified as an Fc-fusion protein; 5) Wnt7a amino acids 264-349 expressed and purified as a Fc-fusion protein; 6) Wnt7a amino acids 264-349 expressed and purified as an Fc-fusion protein with a TEV protease site between the Wnt and Fc domain, subsequently proteolytically digested and chromatographically cleaned to produce purified Wnt7a amino acids 264-249. Molecular weights are indicated with the marker in the far left lane.

Wnt FC-fusion proteins produced in this way clearly show markedly improved yield in both expression media and as a post-purification product (FIG. 4). In addition, the production of a minimal Wnt fragment—Wnt7a amino acids 264-349 was feasible and produced high yields as an FC-fusion protein. These Wnt proteins also displayed high levels of purity as shown by Coomassie SDS-PAGE (FIG. 5).

Example 5

Wnt Truncations Retain In Vitro Biological Activity

Figure 6:
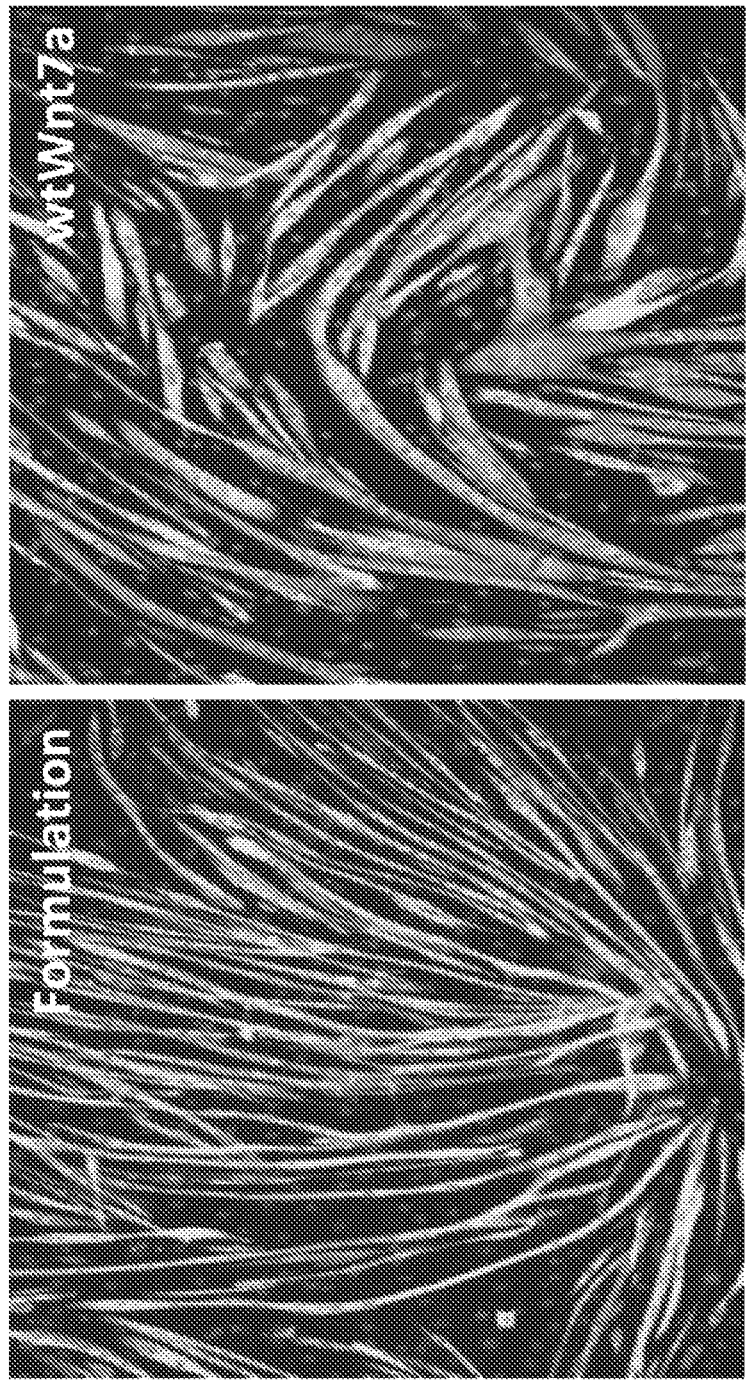

Wnt7a has previously been shown to induce muscle hypertrophic and stem cell expansion via a non-canonical pathway (i.e., not via β-catenin signaling), most likely through the receptor Frizzled 7 (Le Grand 2009) (Von Maltzahn 2012). Wild type Wnt7a induced hypertrophy of myofibers in culture (FIG. 6A). Wnt7a-induced myofiber hypertrophy was quantified and is displayed graphically in FIG. 7.

In vitro hypertrophy experiments were performed as follows: all cells were cultured at 37° C. with humidified air with 5% CO2. C2C12 cells were obtained from American Type Culture Collection (ATCC CRL-1772) and were maintained in Dulbecco's Modified Eagle's Media (DMEM) with 20% fetal bovine serum (FBS) on gelatin coated tissue culture plates. For in vitro hypertrophy assays C2C12 cells were plated on gelatin coated 96 well plates at 2,000 cells per well. Human skeletal muscle myoblasts (HSMMs) were obtained from Lonza and were maintained in F10, 15% FBS, 0.5% Chick Embryo Extract, 0.4 μg/ml dexamethasone and lng/mL basic Fibroblast Growth Factor on collagen coated tissue culture plates. For in vitro hypertrophy assays HSMMs were plated on collagen coated 96 well plates at 12,000 cells per well. For both C2C12 cells and HSMMs in vitro hypertrophy assays, media was changed to DMEM with 2% horse serum after 24 hours. Three day later Wnt proteins were added and allowed to incubate with the cells for an additional two days. Cells were fixed (4% paraformaldehyde PBS, 10 minutes), permeabilzied with 0.1% Triton X-100/PBS, blocked with 10% goat serum and 0.1% Triton X-100 in PBS, and stained with mouse anti-slow MyHC and mouse anti-fast MyHC. Cells were washed with PBS and then stained with goat anti-mouse Alexa 488. Nuclei were stained with DAPI. Image acquisition and fiber diameter measurements were done using Axiovision software. A minimum of 100 diameter counts per well and 2 wells per treatment condition were used to assess the in vitro activity of the different Wnt proteins.

Figure 7:
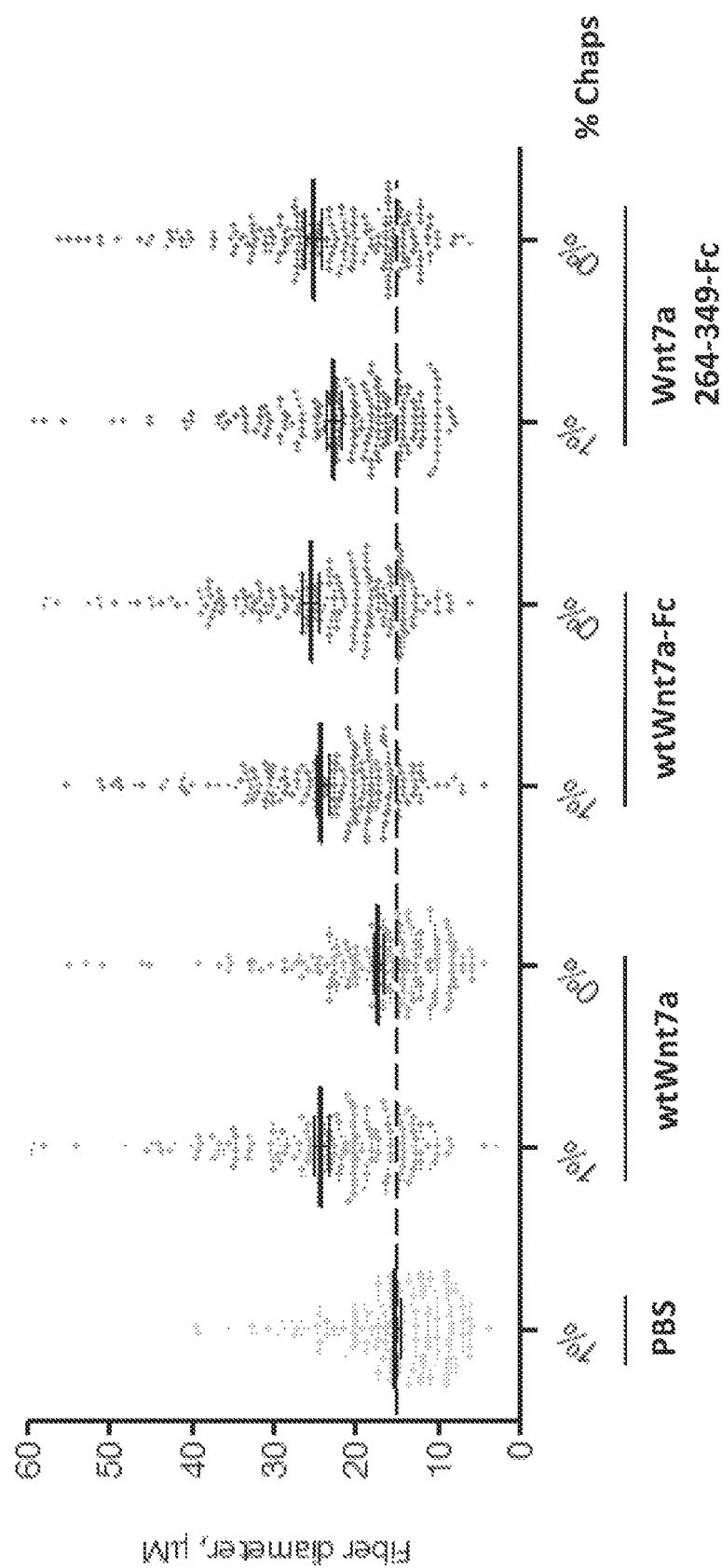
FIG. 7 shows in vitro myofiber hypertrophy data for Wnt7a protein forms. C2C12 mouse myoblasts were differentiated into myofibers and treated with Wnt7a protein as described in Example 5. Fiber diameter was quantified and displayed as mean fiber diameter from 200 measurements. Formulation control (Phosphate buffered Saline supplemented with 1% CHAPS) was compared to wt Wnt7a, wtWnt7a-Fc-fusion protein or the Wnt7a 264-349-Fc-fusion protein. All Wnt proteins were tested in the presence and absence of the CHAPS detergent.
Figure 8A:
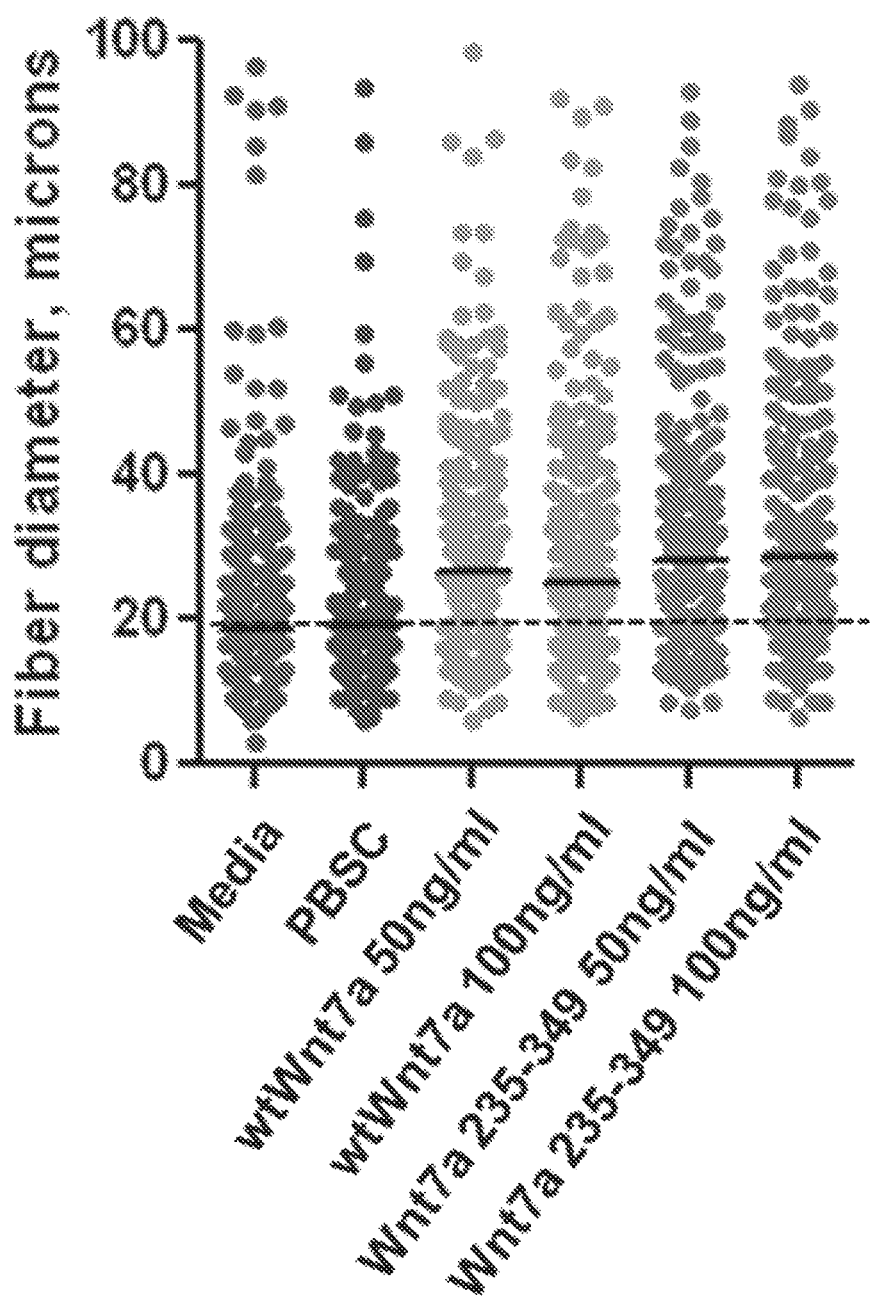
FIG. 8 shows in vitro myofiber hypertrophy data for Wnt7a protein forms. C2C12 mouse myoblasts or primary human dystrophinopathy myoblasts were differentiated into myofibers and treated with Wnt7a protein as described in Example 5. Fiber diameter was quantified and displayed as mean fiber diameter from 100 measurements. A) Formulation control, Phosphate Buffered Saline supplemented with 1% CHAPS (PBSC) was compared to wt Wnt7a, and truncated Wnt7a amino acids 235-349 in mouse C2C12 myofibers. B) Formulation control, Phosphate Buffered Saline supplemented with 1% CHAPS (PBSC) was compared to wt Wnt7a, and truncated Wnt7a amino acids 235-349 in human dystrophinopathy myofibers. C) Dose response of the truncated Wnt7a amino acids 264-349.
Figure 8B:
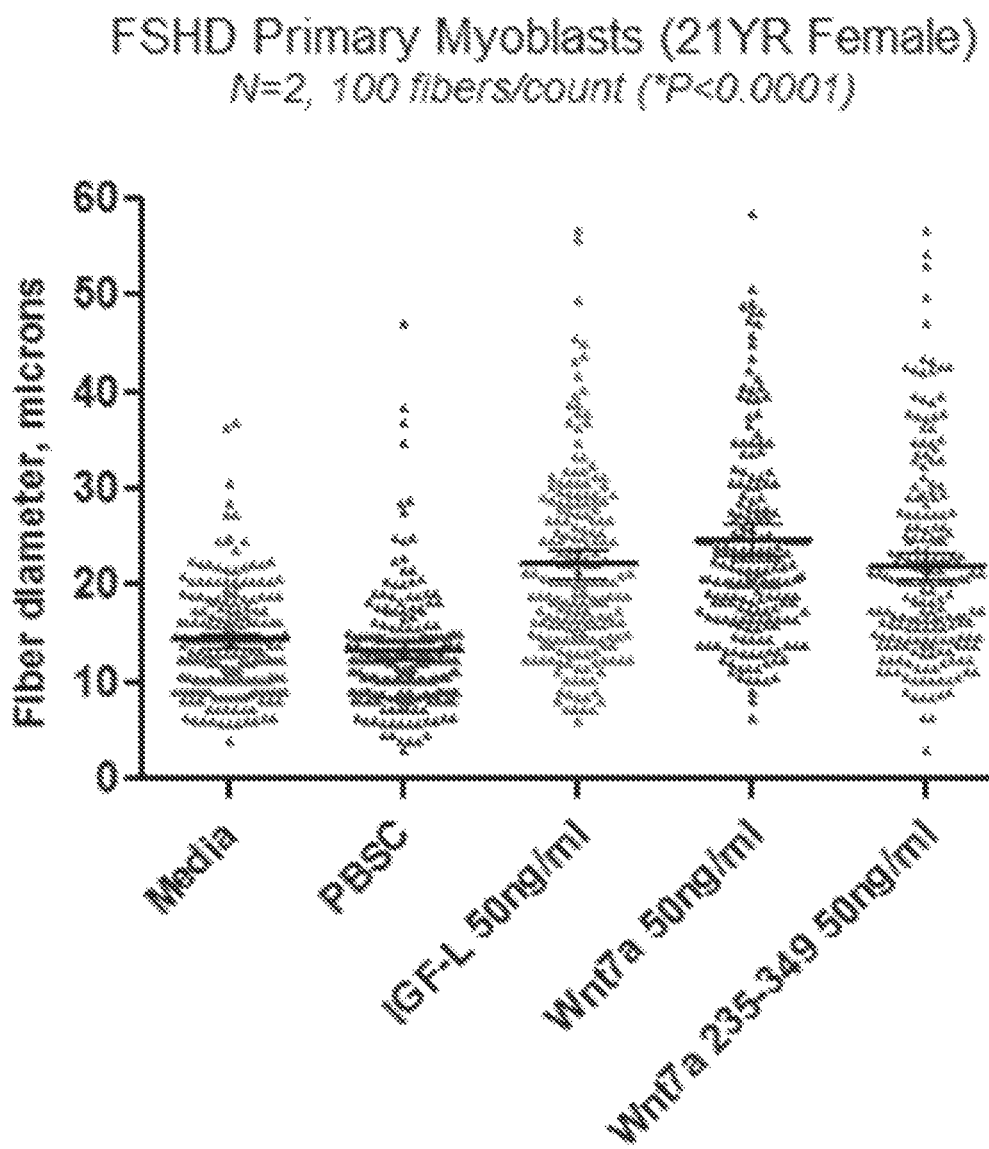
Figure 8C:
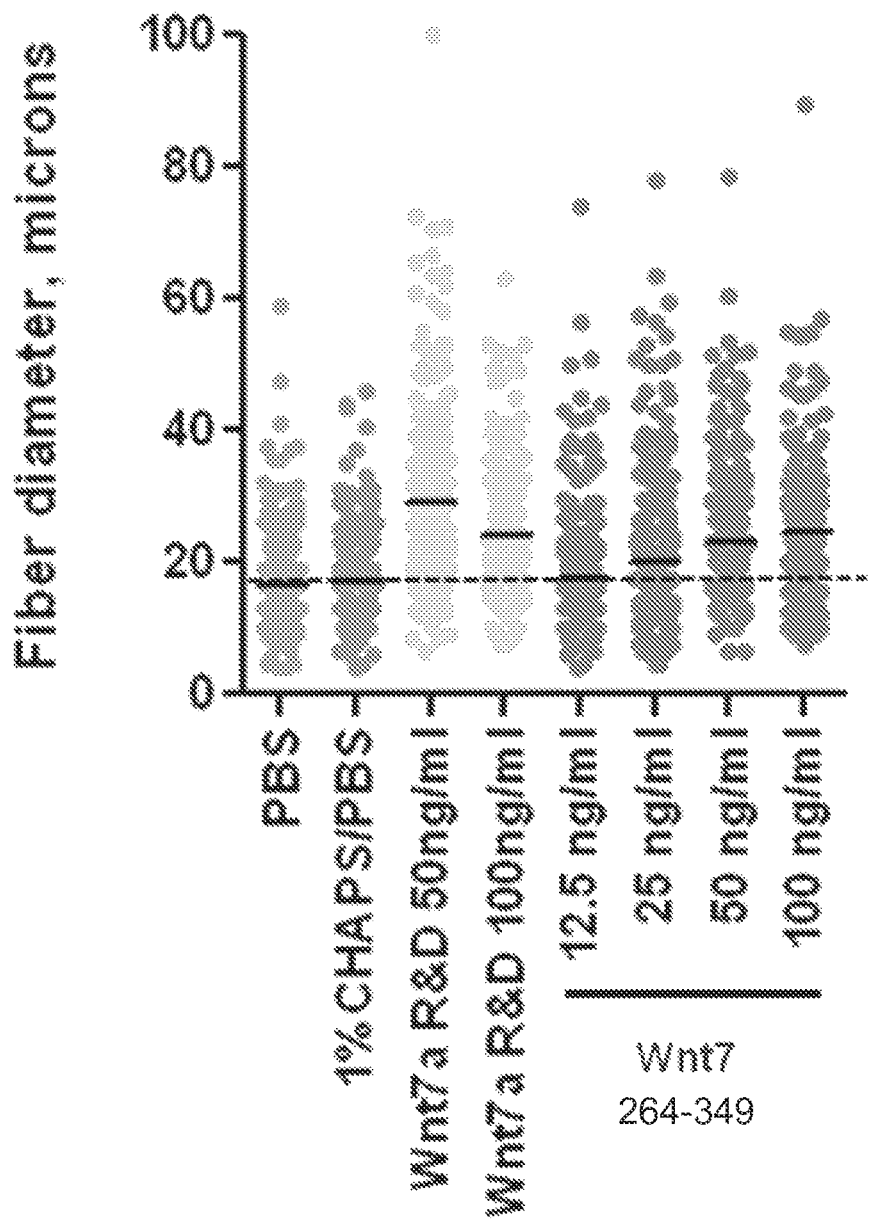

Both wild-type Wnt7a (wtWnt7a) and the Fc fusion (wtWnt7a-FC) induced hypertrophy (FIG. 7). Surprisingly, Wnt7a aa264-349 also induced significant hypertrophy when used either as an Fc-Fusion protein (FIG. 7) or after proteolytic cleavage from the Fc-domain (FIG. 8C). A longer C-terminal Wnt7a fragment—Wnt7a aa235-349 also induced significant hypertrophy in both mouse and human myoblasts, including human primary dystrophinopathy myoblasts (FIG. 8A and 8B). These results clearly indicate that Wnt activity was retained even after significant truncation of the protein, resulting in a fragment with no predicted lipidation sites. In addition, while all Wnt forms tested were active when formulated in the detergent CHAPS, wtWnt7a lost the majority of its biological activity when reformulated in Phosphate Buffered Saline in the absence of CHAPS. wtWnt7a-Fc and the Wnt7a truncations all retained activity when CHAPS was removed (FIG. 7). This result indicates a chaperoning activity on the part of the Fc-fusion and increased aqueous stability for the truncations that lack lipid moieties.

Example 6

Truncated Wnt Proteins and Wnt Fc-Fusion Proteins have Improved Stability and Can Be Formulated in Therapeutically Relevant Excipients All Wnt proteins designed, expressed and purified in Examples 1 and 4 display activity in muscle hypertrophy assays after −20° C. storage and several rounds of freeze-thaw cycles. The modified Wnt proteins are also active when purified and formulated in the detergent CHAPS. However, CHAPS is not currently a commonly used formulation component for therapeutic excipients. In order to assess long term stability and potential to reformulate the Wnt proteins in excipients that are more relevant to therapeutic use, an accelerated stability study coupled to a muscle myofiber hypertrophy activity assessment was performed.

Figure 9A:
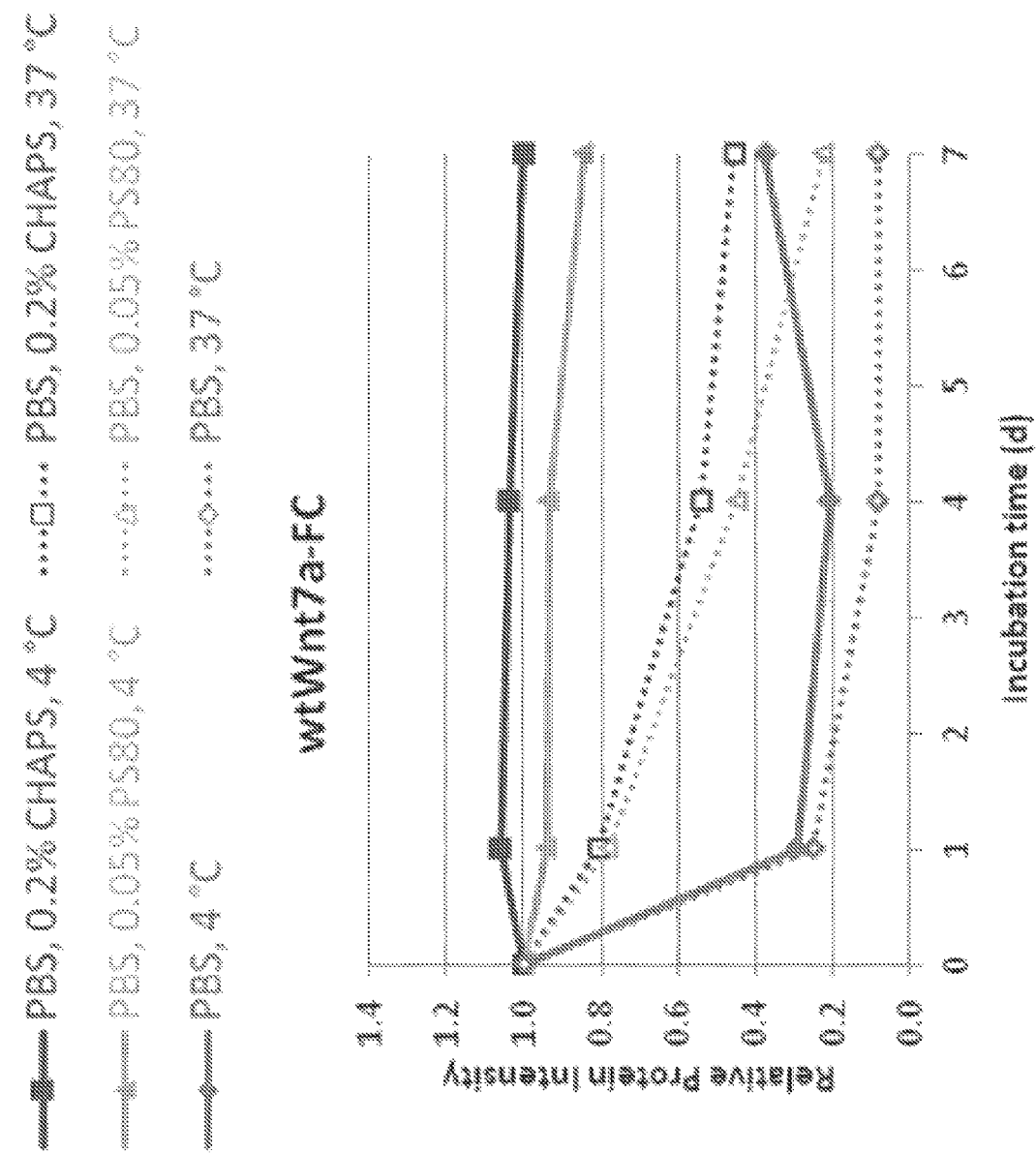
FIG. 9 shows the quantification of an accelerated protein stability assessment of various Wnt7a proteins. Various Wnt7a protein forms, (A) wtWnt7a-FC, (B) Wnt7a aa264-349-FC, and (C) Wnt7a 264-349 were incubated at equal protein concentration at either 4° C. or 37° C. for 0, 1, 4 or 7 days. Three different excipient formulations were assessed: 0.2% CHAPS/PBS, 0.05% Polysorbate 80 (PS80) or PBS alone. Residual protein was assessed using western blot analysis which was then converted using pixel densitometry to a value for fraction of protein remaining compared to starting amount (time 0).
Figure 9B:
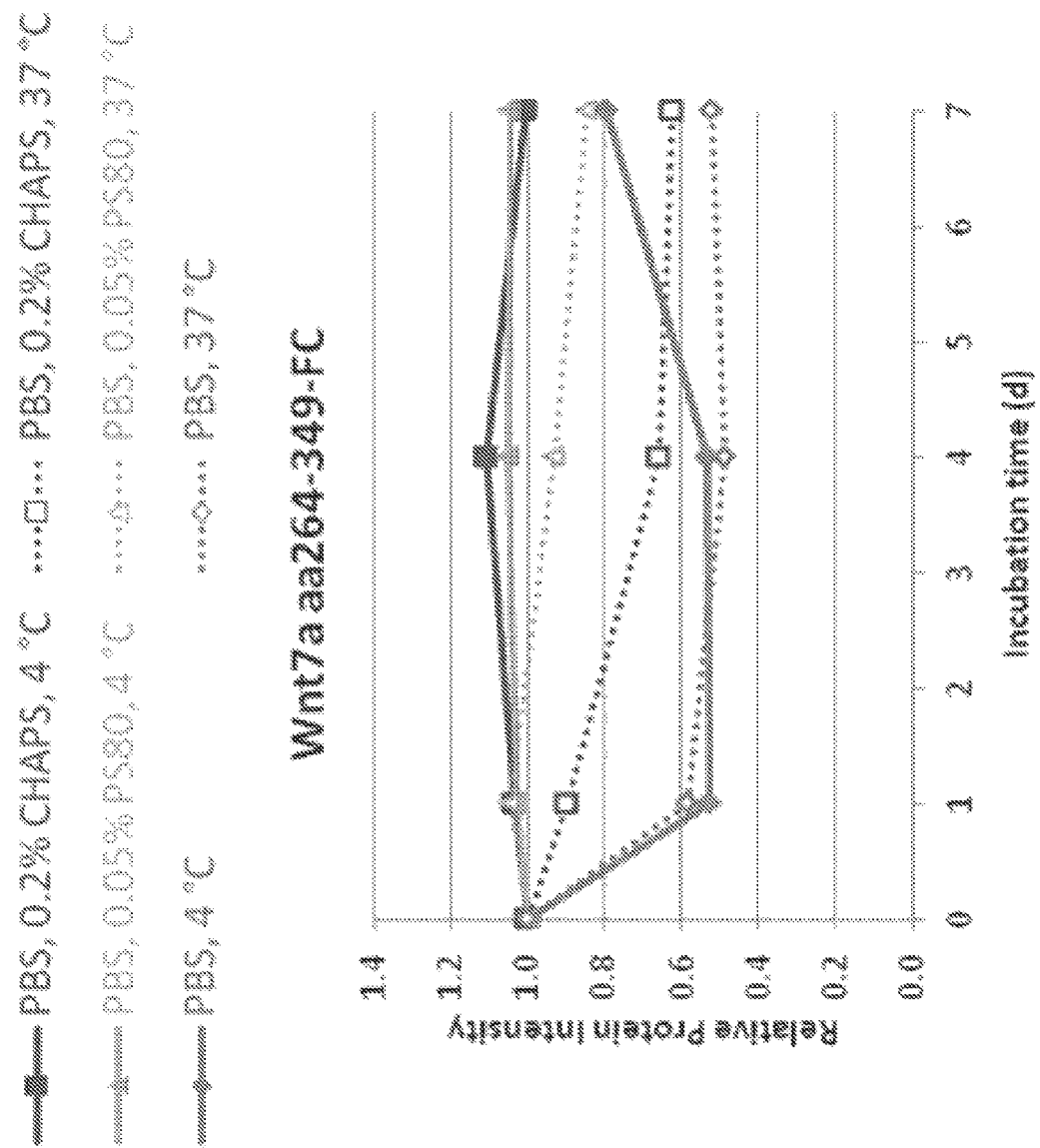
Figure 9C:
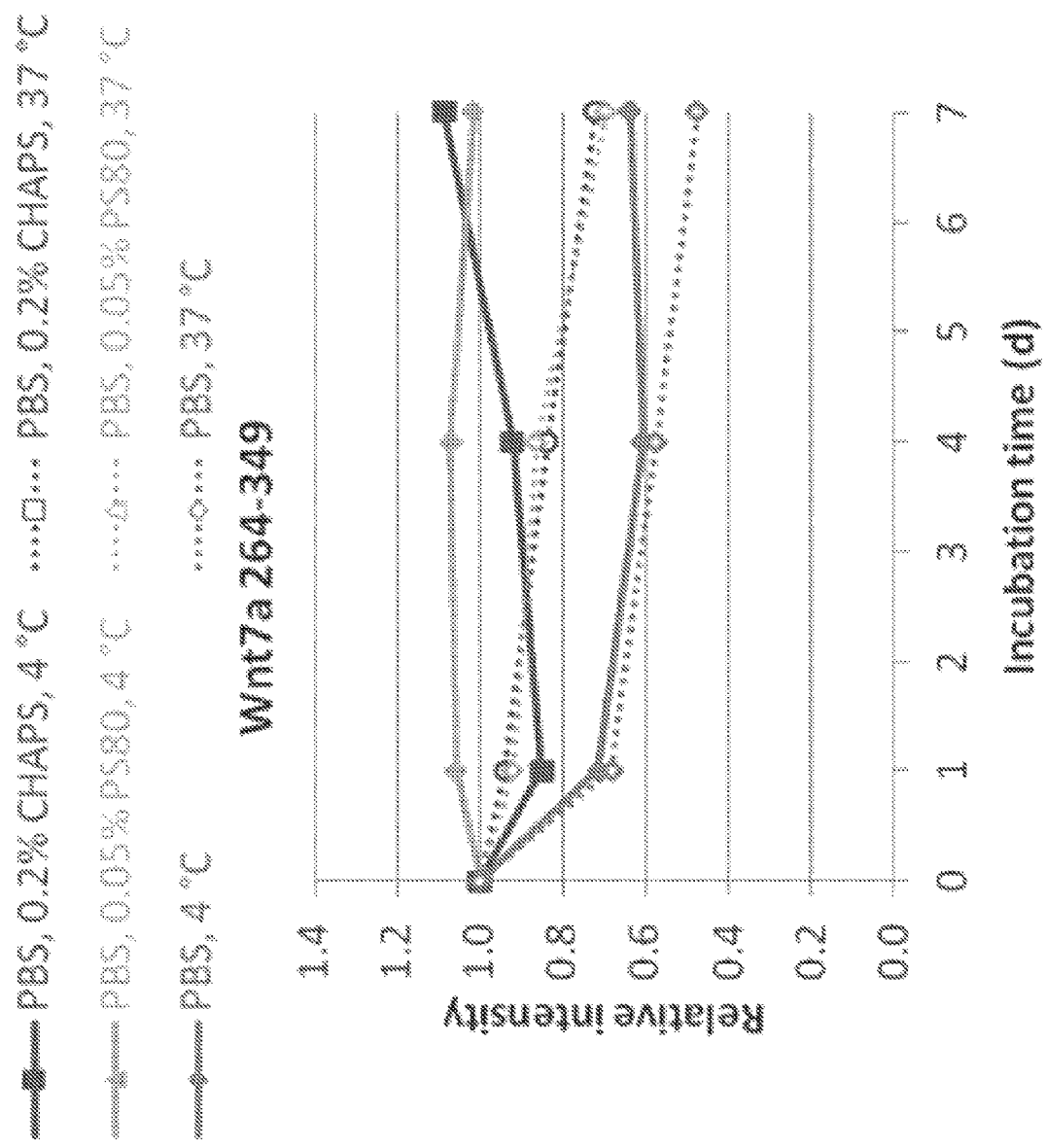

Protein stability of the various Wnt7a protein forms was assessed by incubating equal protein concentrations at either 4° C. or 37° C. for 0, 1, 4 or 7 days. Three different excipient formulations were assessed: 0.2% CHAPS/PBS, 0.05% Polysorbate 80 (PS80)/PBS or PBS alone. Residual protein was assessed using western blot analysis. The western blot signal was converted using pixel densitometry to a value that represented the fraction of protein remaining compared to the starting protein amount (time 0). All protein forms were stable when incubated at 4° C. in either the CHAPS or Polysorbate formulation (FIG. 9). However, significant protein was lost on extended incubation at 4° C. in PBS without the use of a detergent. In addition, both Wnt7a aa264-349 alone or as Fc-fusion was significantly more stable than the full-length Wnt7a-Fc fusion in PBS. This result indicated that Wnt truncation is advantageous under these conditions.

At 37° C., protein was lost from all three protein preparations formulated in PBS. However, the truncated forms of Wnt7a had higher stability than the full-length protein Fc-fusion. In the presence of detergent at 37° C., protein degradation occurred in all Wnt7a protein forms over time, but at a slower rate than the PBS-alone formulation. These data clearly indicate that Wnt7a proteins, including truncations, and fusions thereof, can be formulated in therapeutically relevant excipients such as polysorbate 80 and retain substantial protein stability.

Residual Wnt7a protein activity was assessed after accelerated stability testing. Various forms of Wnt7a protein were incubated at equal protein concentrations at either 4° C. or 37° C. for 0, 1, 4 or 7 days. Excipient formulations 0.2% CHAPS/PBS and 0.05% Polysorbate 80 were assessed. Residual protein was assessed for activity in an in vitro myofiber hypertrophy assay as described in Examples 5 and 6. Negative formulation controls and positive, commercially available Wnt7a protein controls were used. Wnt7a, Wnt7a-Fc-fusion proteins, truncated Wnt7a aa264-349 and truncated Wnt7a aa264-349-Fc-fusion proteins were all compared.

Figure 10A:
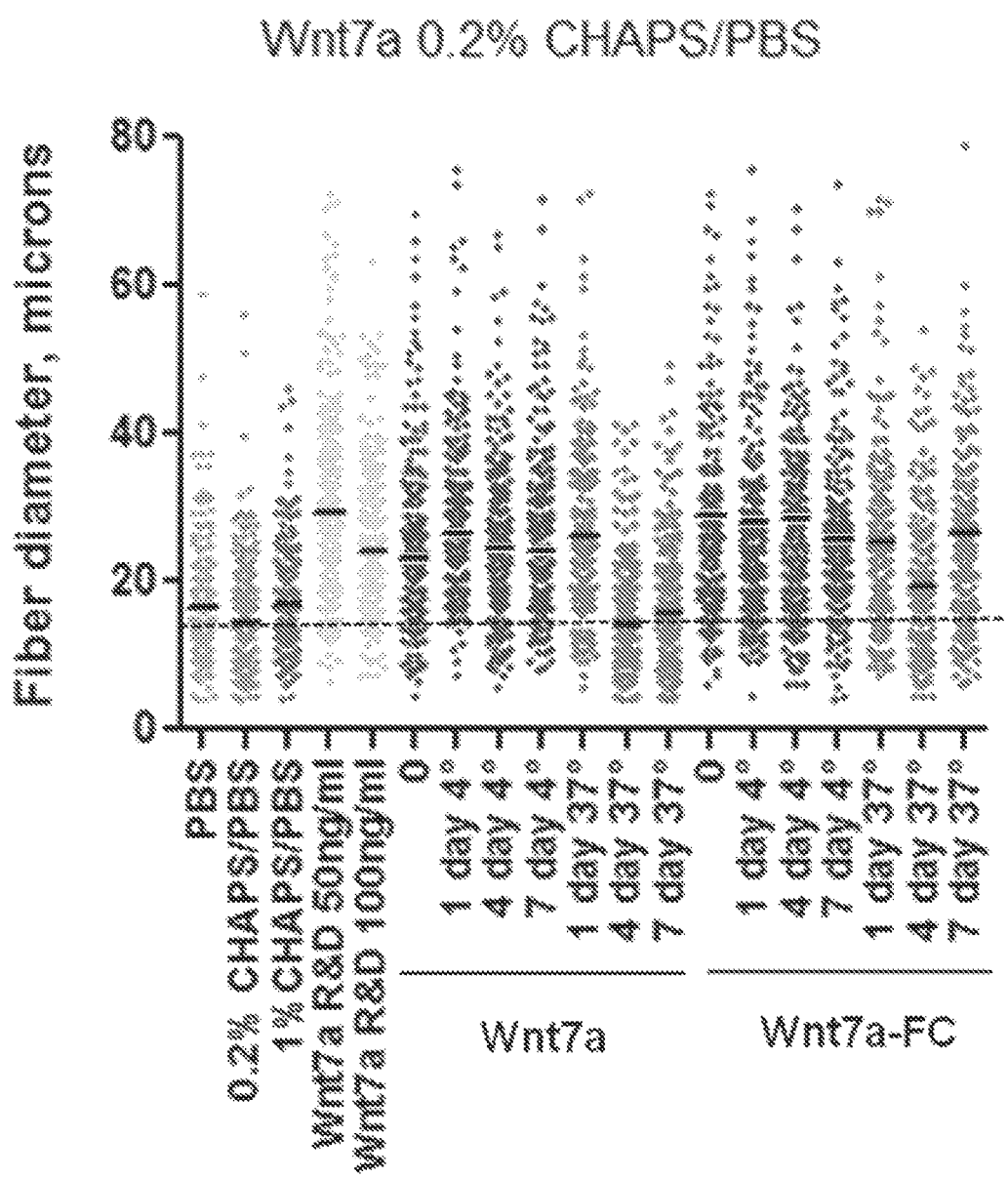
FIG. 10 shows a myofiber hypertrophy assessment of Wnt7a samples from an accelerated stability study. Various Wnt7a protein forms were incubated at equal protein concentration at either 4° C. or 37° C. for 0, 1, 4 or 7 days. Excipient formulation 0.2% CHAPS/PBS was assessed. Residual protein was assessed for activity in an in vitro myofiber hypertrophy assay as described in Examples 5 and 6. Negative formulation controls and positive, commercially available Wnt7a protein control were used. A) Wnt7a and Wnt7a-Fc-fusion and B) truncated Wnt7a 264-349 and truncated Wnt7a 264-349-Fc-fusion proteins were compared.
Figure 10B:
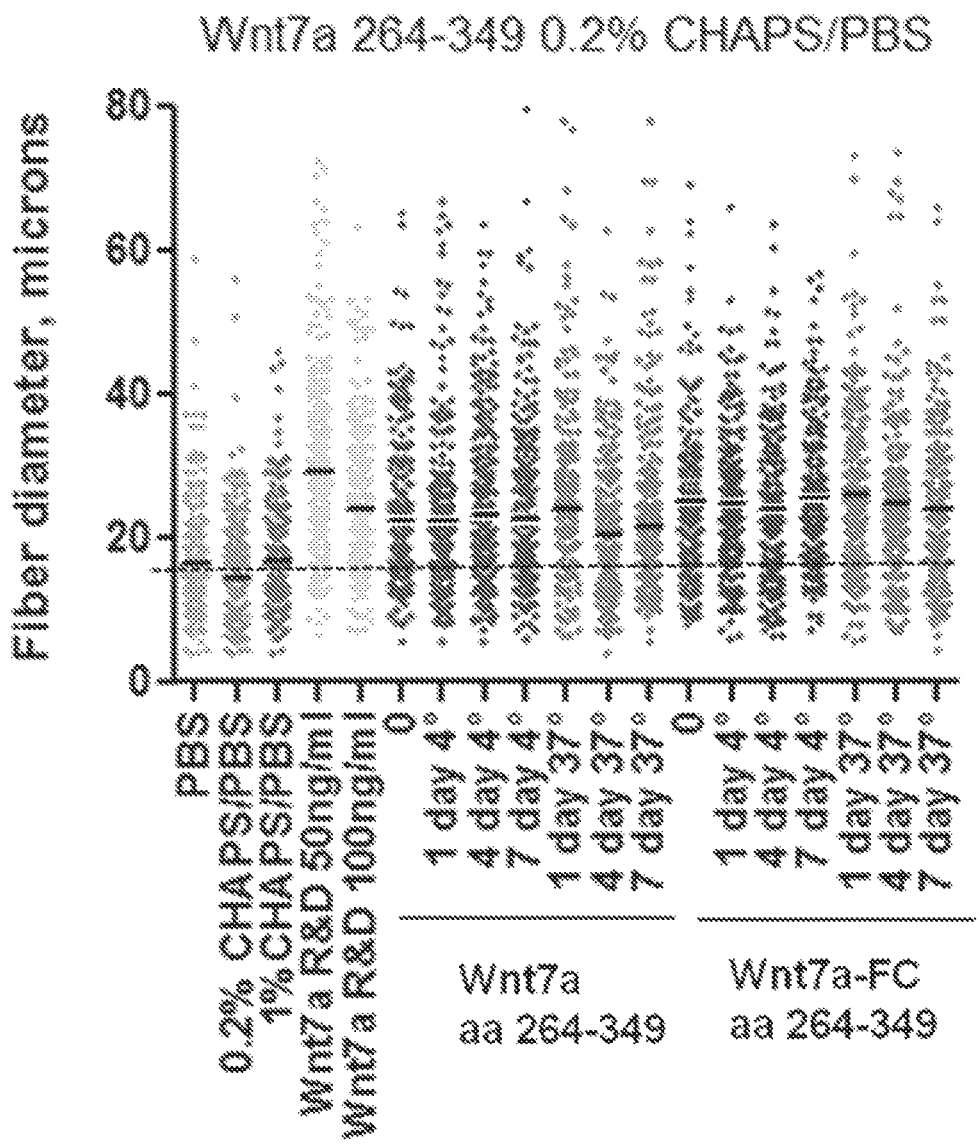
Figure 11A:
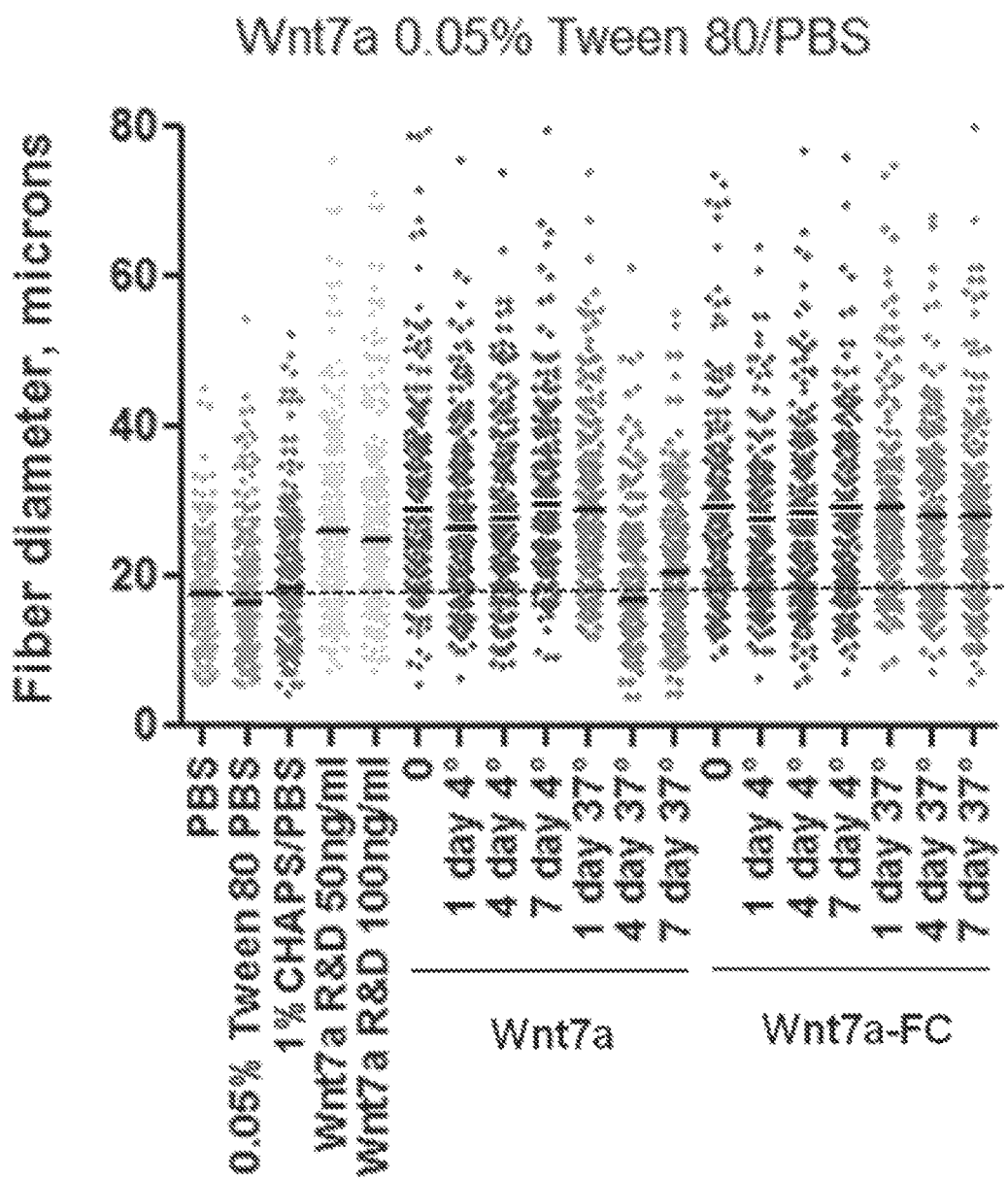
FIG. 11 shows a myofiber hypertrophy assessment of Wnt7a samples from an accelerated stability study. Various Wnt7a protein forms were incubated at equal protein concentration at either 4° C. or 37° C. for 0, 1, 4 or 7 days. Excipient formulation 0.05% Polysorbate 80 (Tween)/PBS was assessed. Residual protein was assessed for activity in an in vitro myofiber hypertrophy assay as described in Examples 5 and 6. Negative formulation controls and positive, commercially available Wnt7a protein control were used. A) Wnt7a and Wnt7a-Fc-fusion and B) truncated Wnt7a 264-349 and truncated Wnt7a 264-349-Fc-fusion proteins were compared.
Figure 11B:
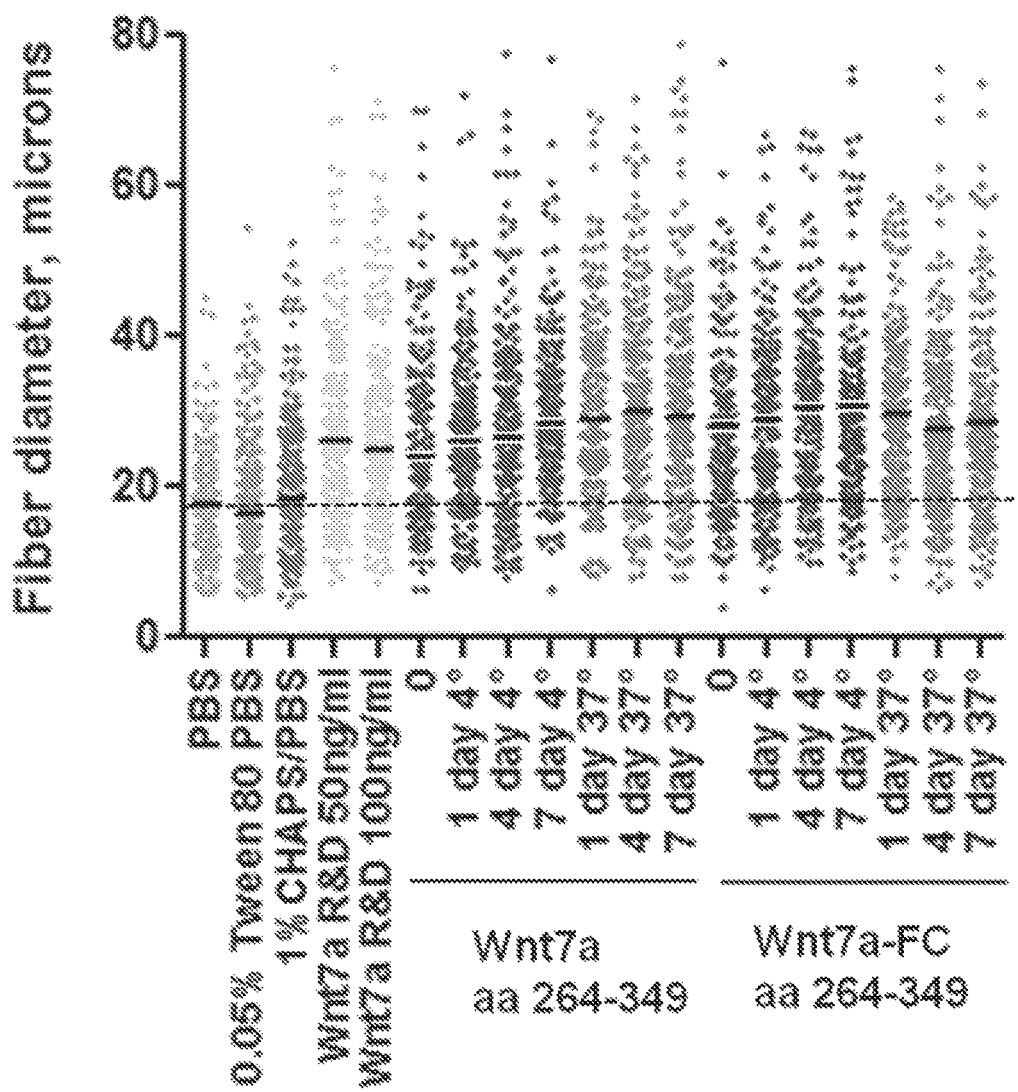
Figure 12A:
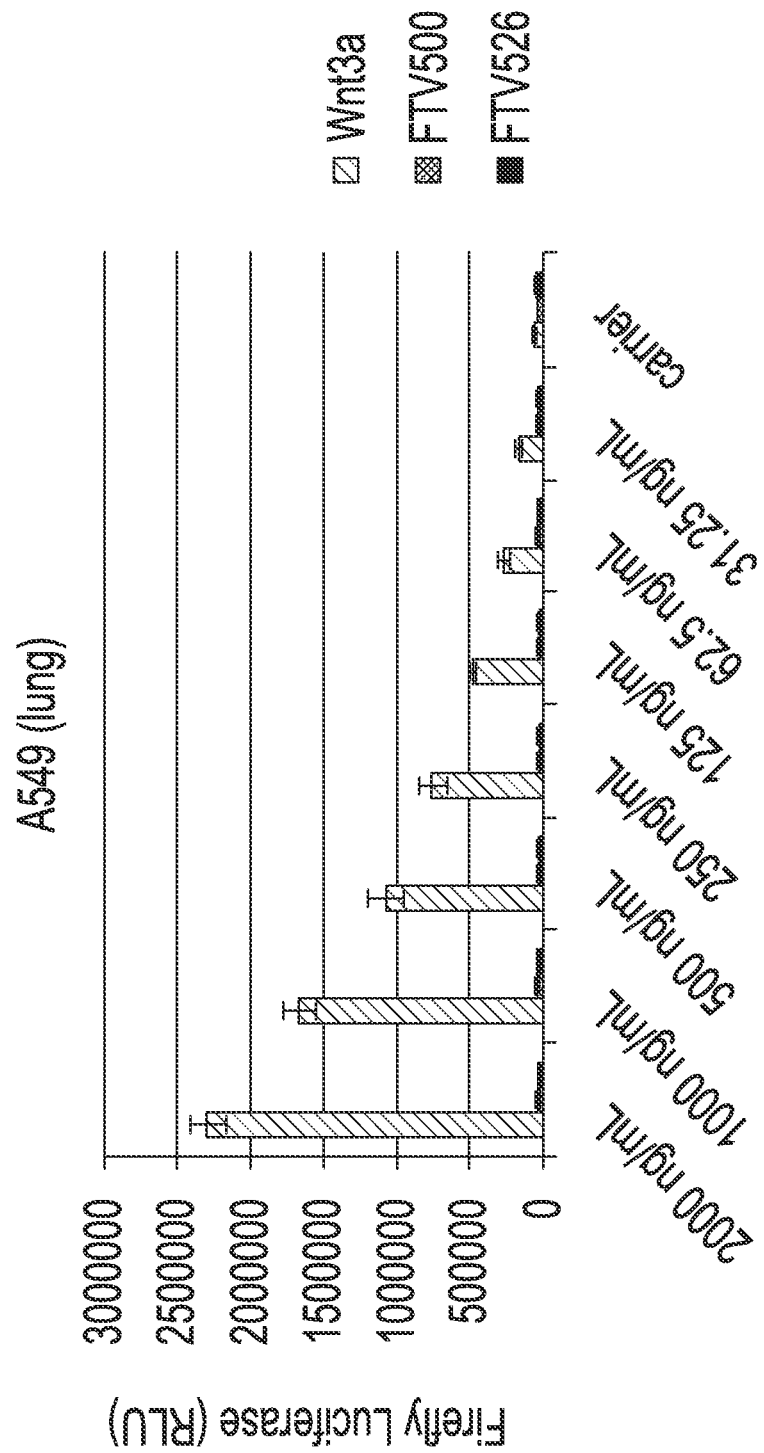
FIG. 12 shows that Wnt7a protein forms are not activators of the canonical Wnt signaling pathway. The pBAR canonical Wnt reporter system was introduced into four cell lines from different tissues. Each line, A) line A549, B) line KG-1a, C) line NALM-6, and D) line TF-1a was tested for response to Wnt signaling. Wnt3a produced a clear luciferase reporter response in all lines tested. Full length Wnt7a (FTV500) and the truncated Wnt7a aa264-349-Fc fusion (FTV526) did not induce the canonical Wnt reporter at any concentration tested.
Figure 12B:
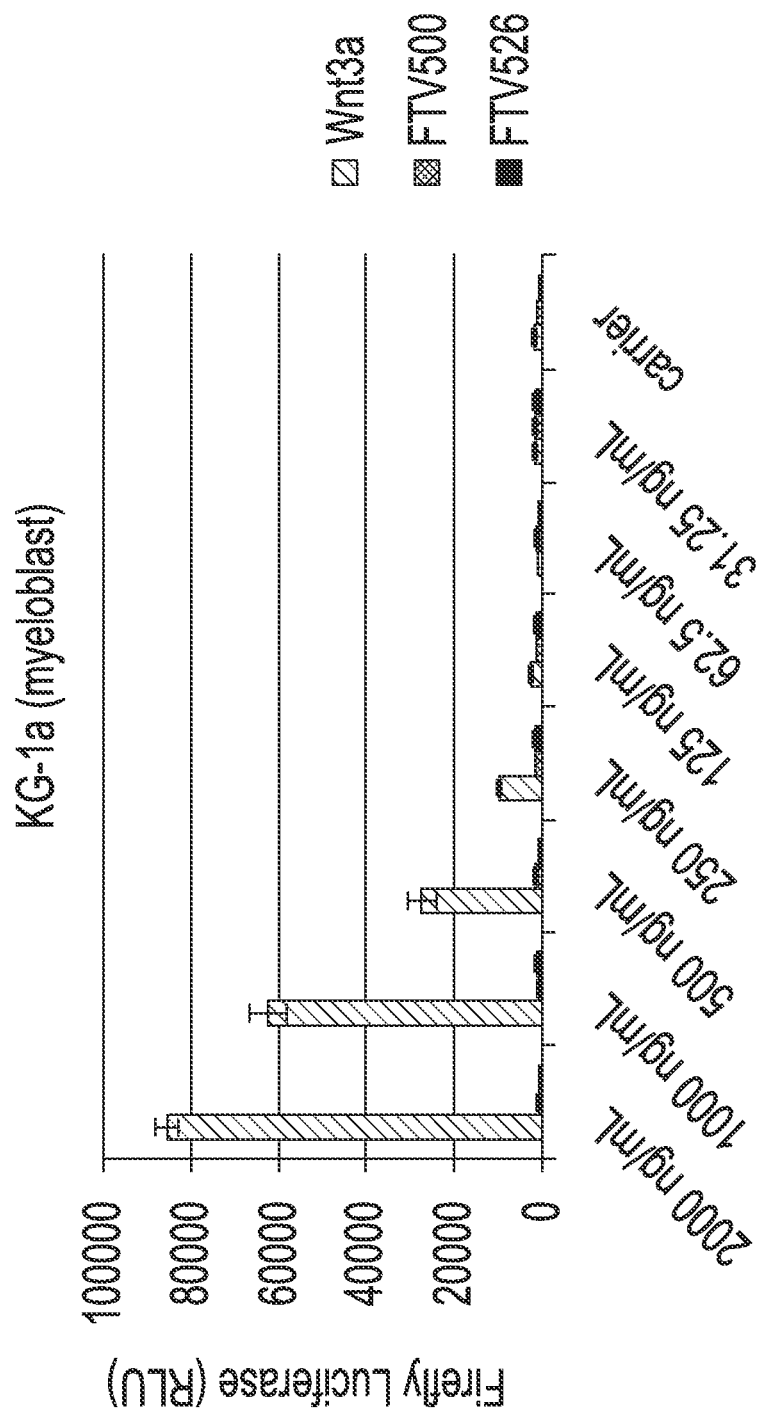
Figure 12C:
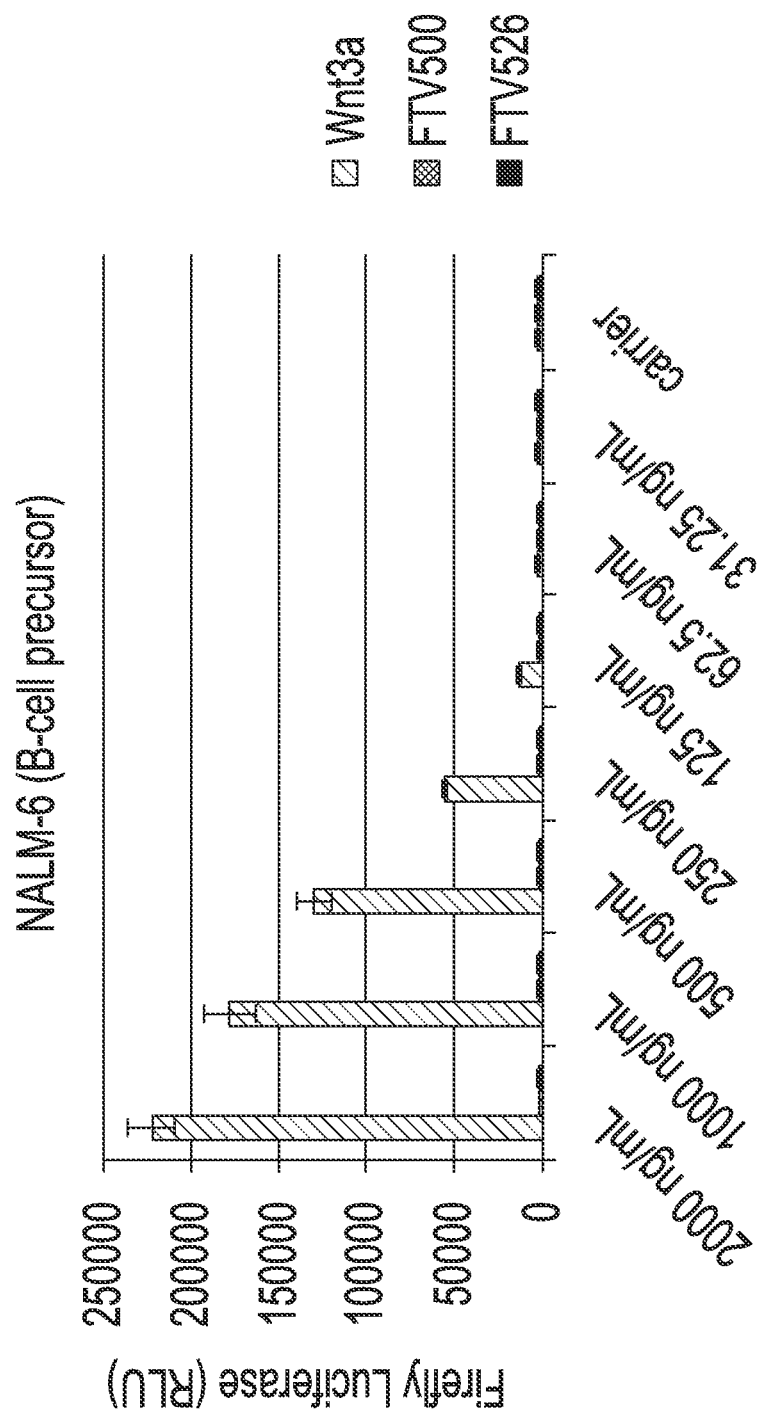
Figure 12D:
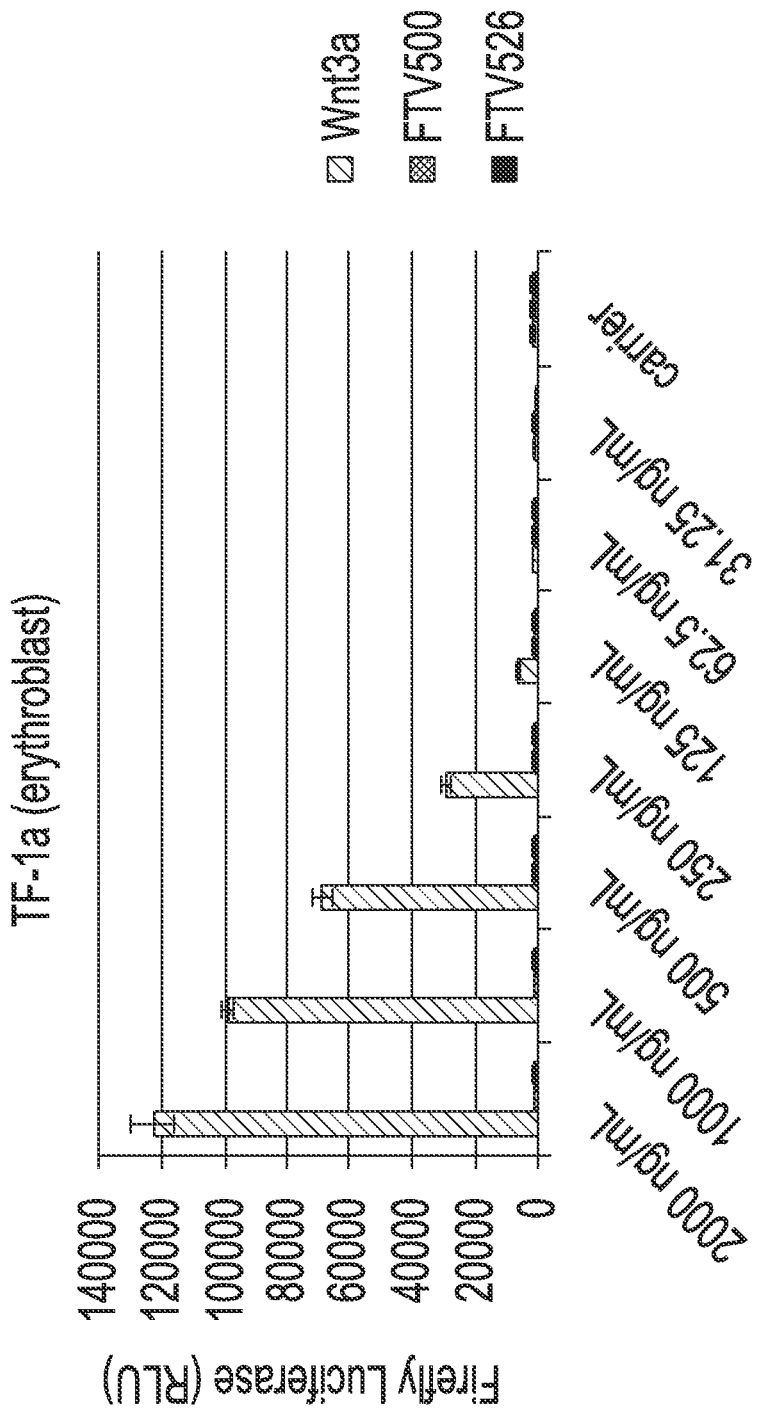

All protein forms tested retained the majority of their original protein activity when incubated in either excipient at 4° C. for up to 7 days (FIGS. 10 and 11).

However, when the incubation temperature was 37° C., full-length Wnt7a lost the majority of its activity over the time course. In addition, when tested as an Fc-fusion protein, the full-length Wnt7a retained more activity over time, indicating that the Fc-domain stabilized the protein structure and therefore activity, confirming the results shown in FIG. 7 and Example 5. The truncated Wnt7a fragment, Wnt7a aa264-349, retained muscle hypertrophy activity over the time course in both excipients, and confirmed the activity of the truncated, non-lipidated Wnt7a protein form and its enhanced properties for therapeutic development. Thus, therapeutically relevant excipients such as Polysorbate 80 can be used in the formulation of Wnt proteins, including truncated Wnt proteins.

Example 7

Wnt7A Protein Truncations and Fusions Proteins Retain Signaling Specificity

There are 19 human Wnt proteins and 10 Frizzled receptors, and various co-receptors such as LRP, ROR, RYK, etc. Wnt7a has been shown to signal via the Frizzled 7 receptor, driving the non-canonical planar cell polarity pathway and activating the PI3-Kinase pathway via a G-protein activation event (Von Maltzahn 2012). The most well characterized Wnt signaling pathway is the canonical Wnt signaling pathway in which Wnt interaction with Frizzled receptors and co-receptors results in β-catenin dependent transcriptional activation, driving survival, proliferation and in some cases differentiation of cells. Wnt proteins engineered for therapeutic development and delivery should be designed so as to retain their receptor and signaling pathway specificity. The engineered truncated and non-lipidated Wnt proteins disclosed in the foregoing Examples retained the desired muscle hypertrophy activity. Further experiments were conducted with the same Wnt7a protein forms to rule out "off-target" effects, such as activating the canonical pathway.

In order to assess this we used an extremely sensitive reporter system, the Wnt pBAR reporter. This reporter consists of a concatemer repeat of the TCF enhancer elements linked to a minimal promoter element driving firefly luciferase expression (Biechele 2008). When transfected into a mammalian cell line, this reporter can be used to measure canonical Wnt activity on cellular treatment. Using a panel of tissue-specific, established stable cell lines containing the pBAR reporter we tested canonical Wnt signaling when the cells were treated with a titration of either recombinant Wnt3a positive control or the Wnt7a variants. As can be seen in FIG. 12, four cell lines containing the pBAR reporter were used to test the canonical Wnt signaling activity of recombinant Wnt3a, full-length Wnt7a and the truncated Wnt7a aa 264-349-FC fusion. While Wnt3a induced a robust luciferase reporter response in all cell lines tested, neither of the Wnt7a protein treatments resulted in canonical activity. It is therefore clear that the truncation of Wnt7a, resulting in fragments that retain activity in the muscle hypertrophy, non-canonical pathways do not gain canonical signaling activity.

Example 8

Wnt7A Truncations and Fusion Proteins Retain In Vivo Therapeutic Activity

Wnt7a has been shown to induce significant skeletal muscle hypertrophy in rodent systems when introduced directly to the muscle by injection of either Wnt expression vectors for in vivo expression or purified preparations of protein. In vivo administration of Wnts for human use will require the ability to formulate the Wnts in relevant excipients and at high concentrations—to minimize injection volumes. Wnt7a Fc-fusions and Wnt truncations achieved high protein production levels, had greater stability, were formulated in therapeutically relevant excipients, and maintained in vitro activity. Formulated Wnt compositions also retained in vivo activity.

Figure 13B:
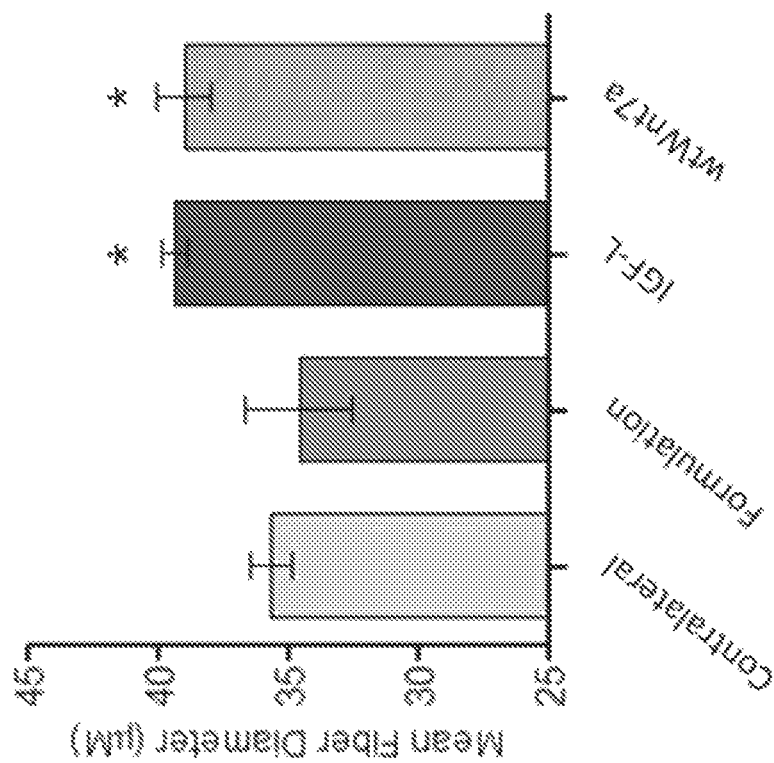
FIG. 13 shows that Wnt7a induces significant hypertrophy in vivo. Full-length Wnt7a was compared with formulation control or IGF-1 in its ability to induce hypertrophy after single injection in to C57B16 mouse tibialis anterior muscle. A) Immunohistochemistry staining of Laminin displaying the cross-sectional area of fibers in muscle treated with either formulation control or Wnt7a. B) Median fiber ferets were calculated from 1000 values/animal and inter-animal mean of median plotted for each treatment group: contralateral (untreated) control, formulation control, IGF-L or Wnt7a. C) All fiber ferets/treatment groups plotted as a population analysis with medians and interquartile values plotted. D) Inter-treatment group values for median, mean and statistical significance. (*p<0.05).
Figure 13A:
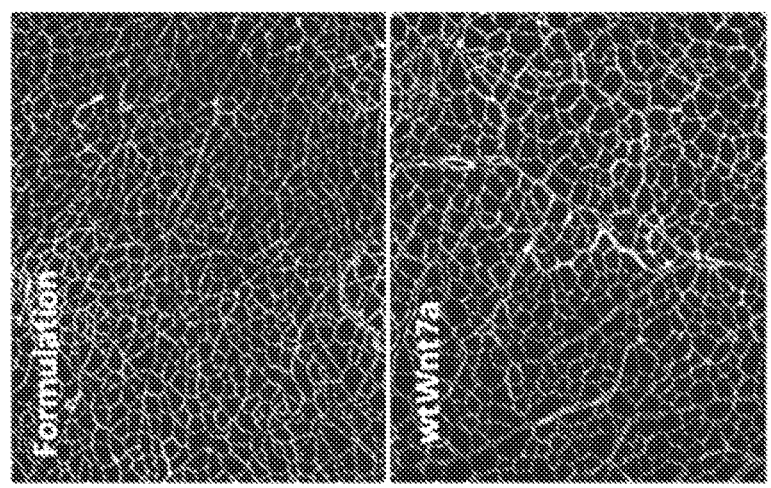
Figure 13C:
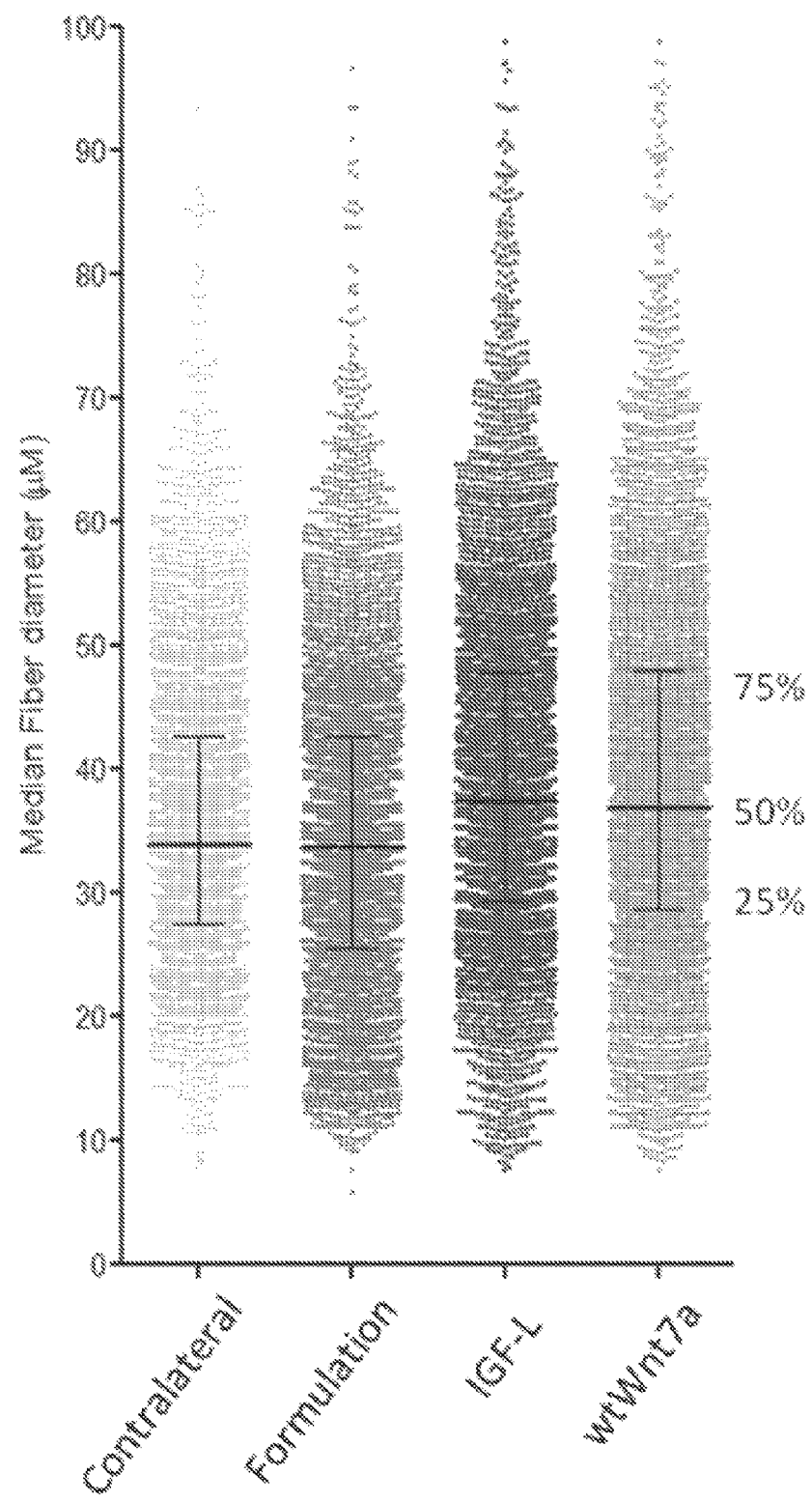

Under isoflurane anesthesia, Wnt7a protein was injected into the exposed tibialis anterior (TA) muscle of the left hindlimb of C57B16 mice which have normal muscle function and also on the C57B/scsn-Dmd$^{Mdx/J}$ mouse strain which is a genetic model of Dystrophinopathy. The incision site was closed with surgical adhesive and then animals were maintained for 3 weeks. At the end of 3 weeks, animals were sacrificed, and the TA muscle was excised, weighed and prepared for histological evaluation by embedding in optimum cutting temperature (OCT) embedding medium. Frozen TA muscles were sectioned at 14 µm and fixed in absolute ethanol for 5 minutes. Sections were permeabilized in 0.1% Triton-X 100/PBS for 20 minutes. Sections were blocked with 50:50 MOM blocking and 10% goat serum/PBS and then immunostained with anti-Pax7 antibody and/or anti-laminin antibody. Following washes with PBS, sections were incubated with a goat anti-mouse Alexa 555 antibody and goat anti-rabbit Alexa 488 antibody. Finally, sections were incubated with DAPI, washed with PBS, and mounted with fluoromount-G. Image acquisition was done using Axiovision software and image analysis for min Feret measurements (minimum fiber diameter measurement) was completed using Image J software. A minimum of 1000 fiber feret values were generated for each animal and medians calculated. Inter animal mean of medians for each treatment group were expressed as well as cumulative fiber population shift for each treatment group. A single injection of 2.5 µg of Wnt7a protein induced significant muscle hypertrophy in a C57B16 mouse TA muscle in comparison to formulation control injections and untreated contralateral muscles from the same animal (FIG. 13). The hypertrophic effect was comparable to an equivalent amount of IGF-L—a known hypertrophic factor. On analysis of the entire population of measured muscle fibers from each treatment group, it was evident that the effect was due to an increase in median fiber diameter i.e., the majority of the muscle was affected.

Figure 14A:
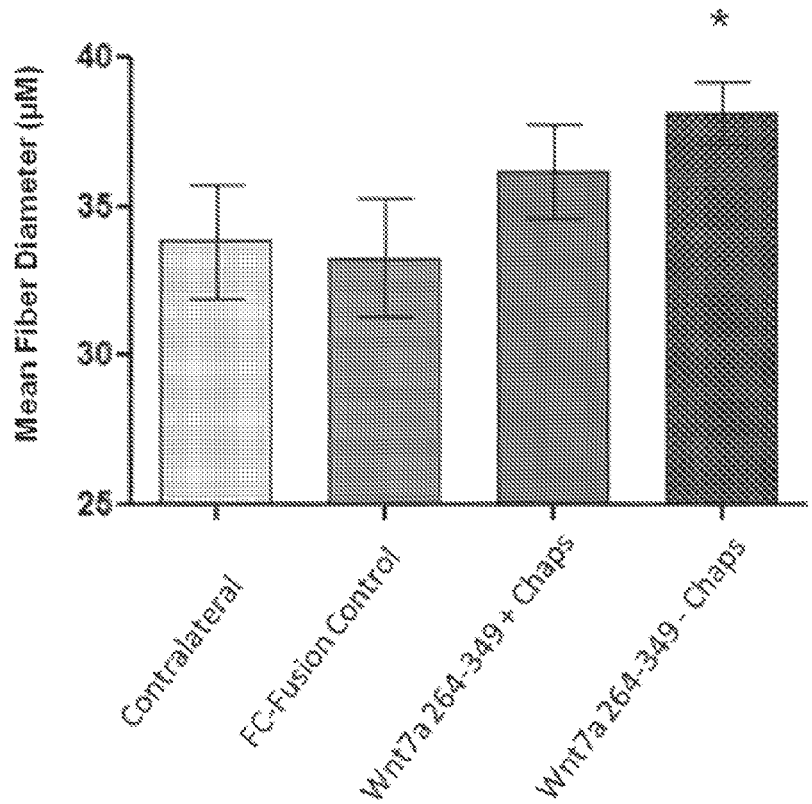
FIG. 14 shows that Wnt7a aa264-349 induces significant hypertrophy in vivo. Wnt7a aa264-349-Fc-fusion protein was compared with an Fc-fusion control in its ability to induce hypertrophy after single injection in to tibialis anterior muscle of the MDX dystrophinopathy mouse model. A) Median fiber ferets were calculated from 1000 values/animal and inter-animal mean of median plotted for each treatment group: contralateral (untreated) control, Fc-fusion control or Wnt7a 264-349-Fc-fusion protein formulated with or without CHAPS detergent. B) All fiber ferets/treatment groups plotted as a population analysis with medians and interquartile values plotted. C) Inter-treatment group values for median, mean and statistical significance. (*p≤0.05).
Figure 14B:
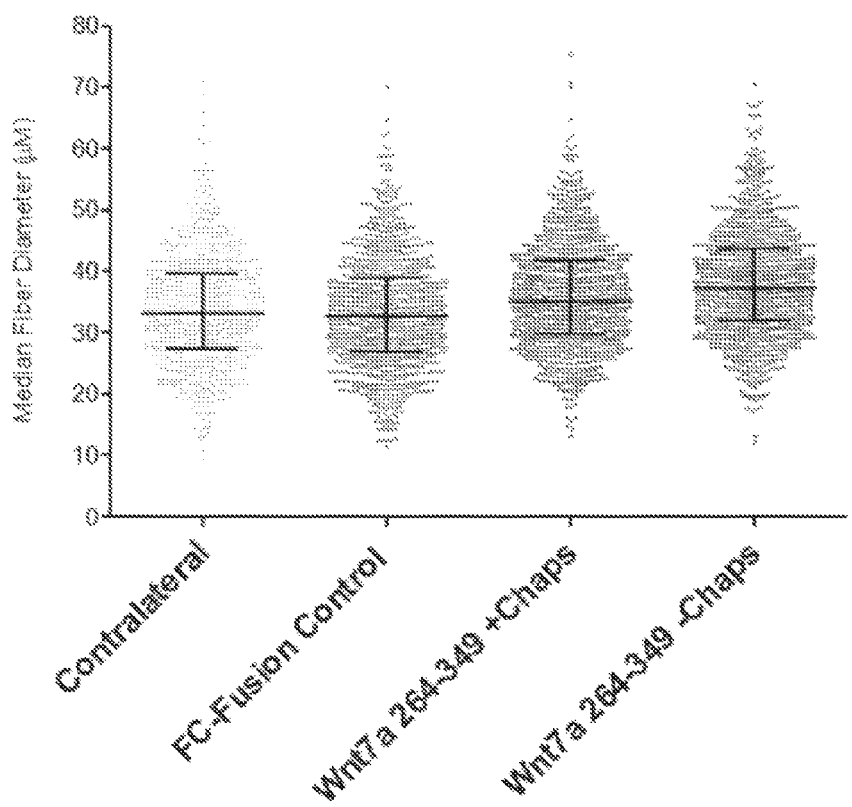

Truncated Wnt7a aa264-349 was also tested in the in vivo hypertrophy assay. 2.5 µg of a Wnt7a Fc-fusion protein was injected into the TA muscle of the dystrophinopathy MDX mouse model. After three weeks, significant hypertrophy was seen in comparison to an Fc-fusion control protein (FIG. 14). The Wnt fragment induced hypertrophy even when administered in a basic Phosphate Buffered Saline formulation. Therefore, is it clear that Wnt7a was successfully fragmented and/or fused to an Fc domain to improve production, formulation, and administration parameters and still retained in vitro and in vivo activity.

Example 9

Improved Pharmacokinetic Properties of Wnt Truncations and Fc-Fusion Proteins

Wnts are secreted proteins that drive cellular processes and tissue development and remodeling by acting in a local, paracrine or gradient signaling potential. In order to fully exploit the therapeutic potential of Wnt proteins, either as agonists of cellular and tissue regenerative processes or as inhibitors of aberrant trophic and neoplastic growth, a protein form with enhanced systemic delivery potential compared the corresponding native, unmodified Wnt protein is required.

A pharmacokinetic analysis was performed to assess the systemic delivery potential of the truncated Wnt7a and Wnt7a Fc-fusion proteins of the invention. A pharmacokinetic analysis was performed to assess the systemic delivery potential of the truncated Wnt7a and Wnt7a Fc-fusion proteins. A single bolus intravenous injection of the various Wnt proteins was performed in C57B16 mice. Serial blood draws were taken at multiple time points over a 48 hr period. Blood was collected in EDTA and processed to plasma. The plasma samples were assessed for Wnt7a protein using sandwich ELISA detection. Antibodies for detection of Wnt7a were raised against peptides from the C-terminal region of the protein and were previously optimized for detection of all engineered and truncated forms of the Wnt7a protein. An unmodified polyclonal antibody served as the coating antibody, and a biotinylated polyclonal antibody recognizing a different region of the Wnt7a protein was used for detection. Plates were coated overnight with unmodified Wnt7a antibody, then blocked with nonfat powdered milk. Purified Wnt7a protein variants were diluted in the same medium as the test samples and spiked with negative control mouse plasma to create a standard concentration curve. Standards and test samples were added to the plate and incubated for an hour. With washes in between each step, biotinylated Wnt7a antibody was added to the plate, followed by neutravidin-conjugated horseradish peroxidase. The ELISA was developed by adding TMB reagent for 10 minutes, followed by addition of sulfuric acid. Absorbance at 450 nm was read on a spectrophotometer, and data were analyzed using Softmax software. A comparative assessment of systemic half-life was made.

Figure 15A:
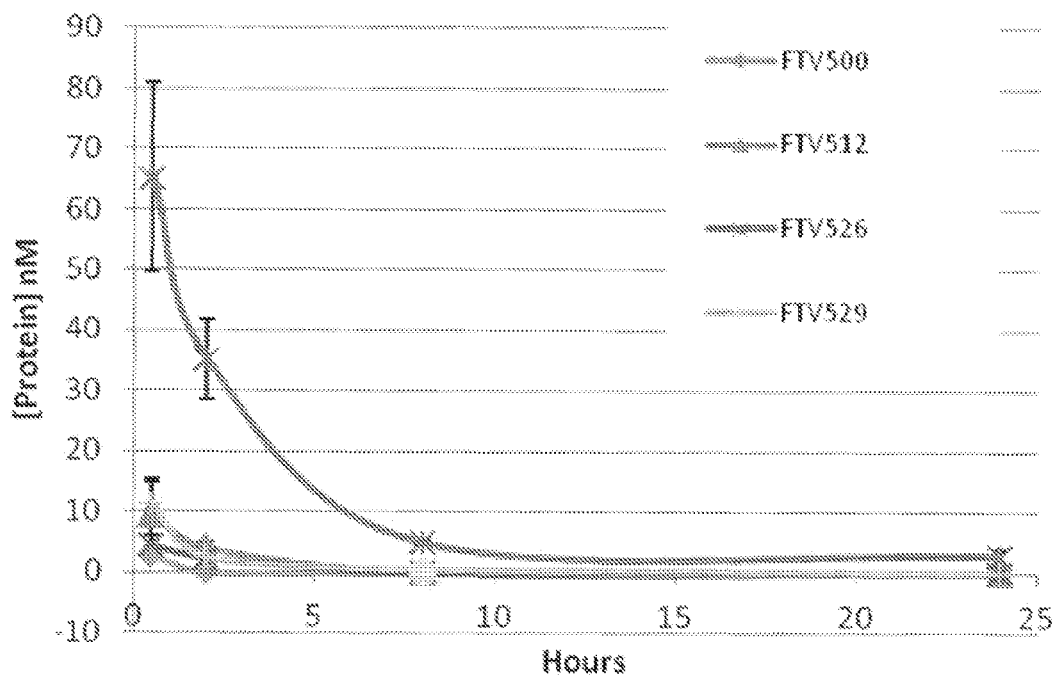
FIG. 15 shows the pharmacokinetic analysis of Wnt7a protein forms. Various Wnt7a protein forms were assessed in a single intravenous administration PK study in C57B16 mice. Full-length Wnt7a (FTV500), Wnt7a-Fc-fusion (FTV512), Wnt7a aa 264-349 fragment (FTV529), and Wnt7a aa 264-349-Fc-fusion protein (FTV526) were compared. A) Wnt7a-specific ELISA on mouse plasma drawn on the indicated time points. B) An expansion of the data sets, excluding FTV526 is shown.
Figure 15B:
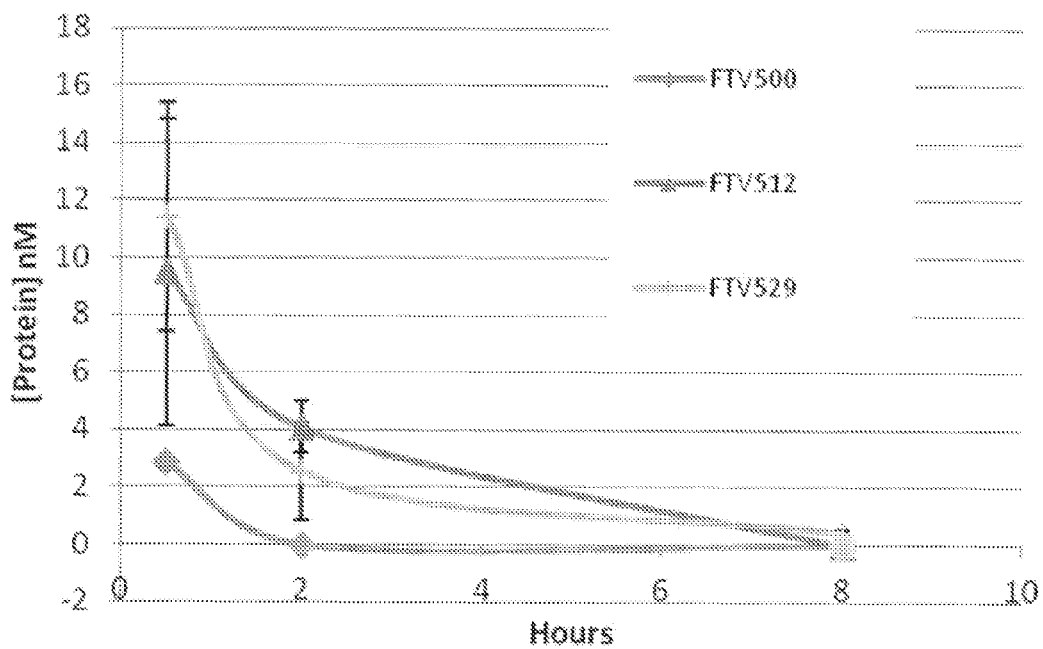

50 μg of full-length Wnt7a was administered (approximately 2 mg/kg) and equal molar amounts of the other Wnt variants were administered. As expected, the full-length Wnt7a protein (FTV500) was only detected systemically for the first time point (30 minutes post administration) after which it was not detectable (FIG. 15). The half-life of Wnt7a was significantly improved when administered as an Fc-fusion protein (FTV512). A significant increase in molecular weight and potential for the Fc-domain to facilitate retention and cycling via the neonate Fc receptor were probable factors contributing to the increased half-life. However, the half-life of the Wnt7a-Fc fusion was still relatively short.

Surprisingly, the very low molecular weight (calculated 11 KDa) Wnt7a truncation encompassing amino acids 264-349 (FTV529) performed equally well compared to the full-length Fc fusion protein, with clear detection at the 2hr time point, indicating that this form of the protein was more amenable to systemic delivery. The Wnt7a aa264-349 truncation expressed as an Fc-fusion protein showed the most significant systemic half-life extension over full-length Wnt7a, with six-fold greater detection at the 30 minute time point and clear detection over background at the 8 hour time point.

Therefore, this analysis clearly showed that the engineered Wnt proteins had improved systemic half-life and that the active, C-terminal fragment (amino acids 264-349) Fc-fusion protein out-performed others.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A biologically active isolated Wnt7a polypeptide comprising an N-terminal deletion, wherein the N-terminal deletion removes one or more lipidation sites and wherein the polypeptide is a Wnt7a polypeptide comprising:
   (a) SEQ ID NO: 2 having an N-terminal deletion of at least 100 amino acids and at most 234 amino acids and a sequence that is at least 95% identical thereto wherein the serine at amino acid position 206 of SEQ ID NO: 2 is removed by the deletion or, if present, is substituted for an Ala, and the sequence is at least 115 amino acids in length;
   (b) SEQ ID NO: 2 having an N-terminal deletion of at least 100 amino acids and at most 220 amino acids and a sequence that is at least 95% identical thereto;
   (c) an amino acid sequence at least 95% identical to the amino acid sequence set forth in SEQ ID NO: 3;
   (d) an amino acid sequence at least 95% identical to the amino acid sequence set forth in SEQ ID NO: 4 and which is at least 115 amino acids in length; or
   (e) an amino acid sequence comprising at least 115 amino acid residues having at least 70 contiguous amino acids identical to the amino acid sequence set forth in any one of SEQ ID NOs: 3-5;
   wherein the polypeptide is a fusion polypeptide.

2. The polypeptide of claim 1, wherein:
   the polypeptide comprises a biologically active Wnt7a polypeptide, wherein the polypeptide retains non-canonical Wnt7a signaling activity or, wherein the polypeptide has improved production yield compared to a naturally occurring Wnt7a polypeptide and/or improved secretory properties compared to a naturally occurring Wnt7a polypeptide and/or improved stability or half-life compared to a naturally occurring Wnt7a polypeptide.

3. The polypeptide of claim 1, wherein the polypeptide comprises the amino acid sequence set forth in any one of SEQ ID NOs: 3-5, wherein the polypeptide comprises at least 115, 116, 117, 118, 119, 120, 121, 122, 123, 124, 125, 126, 127, 128, or 129 contiguous amino acids of the amino acid sequence set forth in SEQ ID NO: 3.

4. The polypeptide of claim 1, wherein the polypeptide has increased solubility in an aqueous solution compared to a Wnt7a polypeptide having the amino acid sequence set forth in any one of SEQ ID NOs: 2 and 18-23, wherein the polypeptide binds a Frizzled receptor on the surface of a cell, and wherein
   (a) the polypeptide retains non-canonical Wnt signaling activity,
   (b) the polypeptide is not lipidated and retains non-canonical Wnt signaling activity;
   (c) the cell is a skeletal muscle satellite stem cell; or
   (d) binding of the polypeptide to the Frizzled receptor increases satellite stem cell expansion compared to the satellite stem cell expansion in the absence of the polypeptide.

5. The polypeptide of claim 1, wherein:
   (a) the polypeptide comprises an Fc-domain, does not have antibody-dependent cell-mediated cytotoxicity (ADCC) or complement-dependent cytotoxicity (CDC) activity, and/or wherein the polypeptide has improved production yield compared to a naturally occurring Wnt polypeptide, and/or wherein the polypeptide has improved secretory properties compared to a naturally occurring Wnt polypeptide, and/or wherein the polypeptide has improved stability or half-life compared to a naturally occurring Wnt polypeptide; and/or
   (b) the polypeptide comprises a native signal peptide, a heterologous signal peptide, or a hybrid of a native and a heterologous signal peptide, wherein the heterologous signal peptide is selected from the group consisting of: a CD33 signal peptide, an immunoglobulin signal peptide, a growth hormone signal peptide, an erythropoietin signal peptide, an albumin signal peptide, a secreted alkaline phosphatase signal peptide, and a viral signal peptide; and/or
   (c) the polypeptide comprises a heterologous protease cleavage site, wherein the heterologous protease cleavage site is selected from the group consisting of: a tobacco etch virus (TEV) protease cleavage site, a heparin cleavage site, a thrombin cleavage site, an enterokinase cleavage site and a Factor Xa cleavage site; and/or
   (d) the polypeptide comprises an epitope tag selected from the group consisting of: a HIS6 epitope, a MYC epitope, a FLAG epitope, a V5 epitope, a VSV-G epitope, and an HA epitope.

6. An isolated biologically active Wnt7a polypeptide comprising SEQ ID NO: 4 or a sequence having at least 90% sequence identity thereto which does not have a lipidation site; wherein the polypeptide is a fusion polypeptide.

7. The isolated biologically active Wnt7a polypeptide of claim 6, wherein the biological activity comprises non-canonical Wnt signaling activity.

8. A method of enhancing regeneration in muscle comprising administering a pharmaceutical composition comprising stem cells contacted with the isolated biologically active Wnt7a polypeptide of claim 6 to a patient in need thereof.

9. An isolated Wnt7a polypeptide according to SEQ ID NOs: 2 and 18-23 having an N-terminal deletion of 220 to 234 amino acids, or a sequence having at least 87% sequence identity thereto, wherein the isolated Wnt7a polypeptide retains or has increased biological activity compared to a wild-type Wnt7a peptide.

10. A polynucleotide encoding a biologically active Wnt7a polypeptide comprising SEQ ID NO: 4 or a sequence having at least 90% sequence identity thereto which does not have a lipidation site.

11. An isolated Wnt7a polypeptide consisting of SEQ ID NO: 5 or a fusion protein comprising a Wnt7a polypeptide consisting of SEQ ID NO: 5.

12. A vector comprising a polynucleotide encoding a biologically active Wnt7a polypeptide comprising SEQ ID NO: 4 or a sequence having at least 90% sequence identity thereto which does not have a lipidation site.

* * * * *

SEQUENCE LISTING

<160> NUMBER OF SEQ ID NOS: 44

<210> SEQ ID NO 1
<211> LENGTH: 1732
<212> TYPE: DNA
<213> ORGANISM: Homo sapiens

<400> SEQUENCE: 1

```
gaggggcggg ggctggaggc agcagcgccc ccgcactccc cgcgtctcgc acacttgcac      60
cggtcgctcg cgcgcagccc ggcgtcgccc cacgccgcgc tcgctcctcc ctccctcctc     120
ccgctccgtg gctcccgtgc tcctggcgag gctcaggcgc ggagcgcgcg gacgggcgca     180
ccgacagacg gccccgggga cgcctcggct cgcgcctccc gggcgggcta tgttgattgc     240
cccgccgggg ccggcccgcg ggatcagcac agcccggccc gcggccccgg cggccaatcg     300
ggactatgaa ccggaaagcg cggcgctgcc tgggccacct ctttctcagc ctgggcatgg     360
tctacctccg gatcggtggc ttctcctcag tggtagctct gggcgcaagc atcatctgta     420
acaagatccc aggcctggct cccagacagc gggcgatctg ccagagccgg cccgacgcca     480
tcatcgtcat aggagaaggc tcacaaatgg gcctggacga gtgtcagttt cagttccgca     540
atggccgctg gaactgctct gcactgggag agcgcaccgt cttcgggaag gagctcaaag     600
tggggagccg ggaggctgcg ttcacctacg ccatcattgc cgccggcgtg gcccacgcca     660
tcacagctgc ctgtacccag ggcaacctga gcgactgtgg ctgcgacaaa gagaagcaag     720
gccagtacca ccgggacgag ggctggaagt ggggtggctg ctctgccgac atccgctacg     780
gcatcggctt cgccaaggtc tttgtggatg cccgggagat caagcagaat gcccggactc     840
```

```
tcatgaactt gcacaacaac gaggcaggcc gaaagatcct ggaggagaac atgaagctgg    900
aatgtaagtg ccacggcgtg tcaggctcgt gcaccaccaa gacgtgctgg accacactgc    960
cacagtttcg ggagctgggc tacgtgctca aggacaagta caacgaggcc gttcacgtgg   1020
agcctgtgcg tgccagccgc aacaagcggc ccaccttcct gaagatcaag aagccactgt   1080
cgtaccgcaa gcccatggac acggacctgg tgtacatcga agtcgccc aactactgcg     1140 aggaggaccc ggtgaccggc agtgtgggca cccagggccg cgcctgcaac aagacggctc   1200
cccaggccag cggctgtgac ctcatgtgct gtgggcgtgg ctacaacacc caccagtacg   1260
cccgcgtgtg gcagtgcaac tgtaagttcc actggtgctg ctatgtcaag tgcaacacgt   1320
gcagcgagcg cacggagatg tacacgtgca agtgagcccc gtgtgcacac caccctcccg   1380
ctgcaagtca gattgctggg aggactggac cgtttccaag ctgcgggctc cctggcagga   1440
tgctgagctt gtcttttctg ctgaggaggg tacttttcct gggtttcctg caggcatccg   1500
tgggggaaaa aaaatctctc agagccctca actattctgt tccacaccca atgctgctcc   1560
accctccccc agacacagcc caggtccctc cgcggctgga gcgaagcctt ctgcagcagg   1620
aactctggac ccctgggcct catcacagca atatttaaca atttattctg ataaaaataa   1680
tattaattta tttaattaaa aagaattctt ccacaaaaaa aaaaaaaaaa aa            1732
```

<210> SEQ ID NO 2
<211> LENGTH: 349
<212> TYPE: PRT
<213> ORGANISM: Homo sapiens

<400> SEQUENCE: 2

```
Met Asn Arg Lys Ala Arg Arg Cys Leu Gly His Leu Phe Leu Ser Leu
1               5                  10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
```

-continued

```
             210                 215                 220
Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345
```

<210> SEQ ID NO 3
<211> LENGTH: 129
<212> TYPE: PRT
<213> ORGANISM: Homo sapiens

<400> SEQUENCE: 3

```
Phe Arg Glu Leu Gly Tyr Val Leu Lys Asp Lys Tyr Asn Glu Ala Val
1               5                   10                  15

His Val Glu Pro Val Arg Ala Ser Arg Asn Lys Arg Pro Thr Phe Leu
            20                  25                  30

Lys Ile Lys Lys Pro Leu Ser Tyr Arg Lys Pro Met Asp Thr Asp Leu
        35                  40                  45

Val Tyr Ile Glu Lys Ser Pro Asn Tyr Cys Glu Glu Asp Pro Val Thr
    50                  55                  60

Gly Ser Val Gly Thr Gln Gly Arg Ala Cys Asn Lys Thr Ala Pro Gln
65                  70                  75                  80

Ala Ser Gly Cys Asp Leu Met Cys Cys Gly Arg Gly Tyr Asn Thr His
                85                  90                  95

Gln Tyr Ala Arg Val Trp Gln Cys Asn Cys Lys Phe His Trp Cys Cys
            100                 105                 110

Tyr Val Lys Cys Asn Thr Cys Ser Glu Arg Thr Glu Met Tyr Thr Cys
        115                 120                 125

Lys
```

<210> SEQ ID NO 4
<211> LENGTH: 115
<212> TYPE: PRT
<213> ORGANISM: Homo sapiens

<400> SEQUENCE: 4

```
Ala Val His Val Glu Pro Val Arg Ala Ser Arg Asn Lys Arg Pro Thr
1               5                   10                  15

Phe Leu Lys Ile Lys Lys Pro Leu Ser Tyr Arg Lys Pro Met Asp Thr
            20                  25                  30

Asp Leu Val Tyr Ile Glu Lys Ser Pro Asn Tyr Cys Glu Glu Asp Pro
        35                  40                  45

Val Thr Gly Ser Val Gly Thr Gln Gly Arg Ala Cys Asn Lys Thr Ala
    50                  55                  60
```

```
Pro Gln Ala Ser Gly Cys Asp Leu Met Cys Cys Gly Arg Gly Tyr Asn
 65                  70                  75                  80

Thr His Gln Tyr Ala Arg Val Trp Gln Cys Asn Cys Lys Phe His Trp
                 85                  90                  95

Cys Cys Tyr Val Lys Cys Asn Thr Cys Ser Glu Arg Thr Glu Met Tyr
            100                 105                 110

Thr Cys Lys
        115

<210> SEQ ID NO 5
<211> LENGTH: 86
<212> TYPE: PRT
<213> ORGANISM: Homo sapiens

<400> SEQUENCE: 5

Met Asp Thr Asp Leu Val Tyr Ile Glu Lys Ser Pro Asn Tyr Cys Glu
 1               5                  10                  15

Glu Asp Pro Val Thr Gly Ser Val Gly Thr Gln Gly Arg Ala Cys Asn
                20                  25                  30

Lys Thr Ala Pro Gln Ala Ser Gly Cys Asp Leu Met Cys Cys Gly Arg
             35                  40                  45

Gly Tyr Asn Thr His Gln Tyr Ala Arg Val Trp Gln Cys Asn Cys Lys
 50                  55                  60

Phe His Trp Cys Cys Tyr Val Lys Cys Asn Thr Cys Ser Glu Arg Thr
 65                  70                  75                  80

Glu Met Tyr Thr Cys Lys
                85

<210> SEQ ID NO 6
<211> LENGTH: 163
<212> TYPE: PRT
<213> ORGANISM: Artificial Sequence
<220> FEATURE:
<223> OTHER INFORMATION: Fusion protein

<400> SEQUENCE: 6

Met Pro Leu Leu Leu Leu Leu Pro Leu Leu Trp Ala Gly Ala Leu Ala
 1               5                  10                  15

Met Asp Phe Arg Glu Leu Gly Tyr Val Leu Lys Asp Lys Tyr Asn Glu
                20                  25                  30

Ala Val His Val Glu Pro Val Arg Ala Ser Arg Asn Lys Arg Pro Thr
             35                  40                  45

Phe Leu Lys Ile Lys Lys Pro Leu Ser Tyr Arg Lys Pro Met Asp Thr
 50                  55                  60

Asp Leu Val Tyr Ile Glu Lys Ser Pro Asn Tyr Cys Glu Glu Asp Pro
 65                  70                  75                  80

Val Thr Gly Ser Val Gly Thr Gln Gly Arg Ala Cys Asn Lys Thr Ala
                85                  90                  95

Pro Gln Ala Ser Gly Cys Asp Leu Met Cys Cys Gly Arg Gly Tyr Asn
            100                 105                 110

Thr His Gln Tyr Ala Arg Val Trp Gln Cys Asn Cys Lys Phe His Trp
            115                 120                 125

Cys Cys Tyr Val Lys Cys Asn Thr Cys Ser Glu Arg Thr Glu Met Tyr
            130                 135                 140

Thr Cys Lys Glu Asn Leu Tyr Phe Gln Gly Gly Gly Ser His His His
145                 150                 155                 160
```

His His His

<210> SEQ ID NO 7
<211> LENGTH: 164
<212> TYPE: PRT
<213> ORGANISM: Artificial Sequence
<220> FEATURE:
<223> OTHER INFORMATION: Fusion protein

<400> SEQUENCE: 7

```
Met Pro Leu Leu Leu Leu Pro Leu Leu Trp Ala Gly Ala Leu Ala
1               5                   10                  15

Met Asp Phe Arg Glu Leu Gly Tyr Val Leu Lys Asp Lys Tyr Asn Glu
            20                  25                  30

Ala Val His Val Glu Pro Val Arg Ala Ser Arg Asn Lys Arg Pro Thr
        35                  40                  45

Phe Leu Lys Ile Lys Lys Pro Leu Ser Tyr Arg Lys Pro Met Asp Thr
    50                  55                  60

Asp Leu Val Tyr Ile Glu Lys Ser Pro Asn Tyr Cys Glu Glu Asp Pro
65                  70                  75                  80

Val Thr Gly Ser Val Gly Thr Gln Gly Arg Ala Cys Asn Lys Thr Ala
                85                  90                  95

Pro Gln Ala Ser Gly Cys Asp Leu Met Cys Cys Gly Arg Gly Tyr Asn
            100                 105                 110

Thr His Gln Tyr Ala Arg Val Trp Gln Cys Asn Cys Lys Phe His Trp
        115                 120                 125

Cys Cys Tyr Val Lys Cys Asn Thr Cys Ser Glu Arg Thr Glu Met Tyr
130                 135                 140

Thr Cys Lys Glu Asn Leu Tyr Phe Gln Gly Gly Gly Asp Tyr Lys Asp
145                 150                 155                 160

Asp Asp Asp Lys
```

<210> SEQ ID NO 8
<211> LENGTH: 166
<212> TYPE: PRT
<213> ORGANISM: Artificial Sequence
<220> FEATURE:
<223> OTHER INFORMATION: Fusion protein

<400> SEQUENCE: 8

```
Met Glu Thr Asp Thr Leu Leu Leu Trp Val Leu Leu Leu Trp Val Pro
1               5                   10                  15

Gly Ser Thr Gly Asp Phe Arg Glu Leu Gly Tyr Val Leu Lys Asp Lys
            20                  25                  30

Tyr Asn Glu Ala Val His Val Glu Pro Val Arg Ala Ser Arg Asn Lys
        35                  40                  45

Arg Pro Thr Phe Leu Lys Ile Lys Lys Pro Leu Ser Tyr Arg Lys Pro
    50                  55                  60

Met Asp Thr Asp Leu Val Tyr Ile Glu Lys Ser Pro Asn Tyr Cys Glu
65                  70                  75                  80

Glu Asp Pro Val Thr Gly Ser Val Gly Thr Gln Gly Arg Ala Cys Asn
                85                  90                  95

Lys Thr Ala Pro Gln Ala Ser Gly Cys Asp Leu Met Cys Cys Gly Arg
            100                 105                 110

Gly Tyr Asn Thr His Gln Tyr Ala Arg Val Trp Gln Cys Asn Cys Lys
        115                 120                 125

Phe His Trp Cys Cys Tyr Val Lys Cys Asn Thr Cys Ser Glu Arg Thr
```

```
                130                 135                 140
Glu Met Tyr Thr Cys Lys Glu Asn Leu Tyr Phe Gln Gly Gly Gly Ser
145                 150                 155                 160

His His His His His His
                165

<210> SEQ ID NO 9
<211> LENGTH: 167
<212> TYPE: PRT
<213> ORGANISM: Artificial Sequence
<220> FEATURE:
<223> OTHER INFORMATION: Fusion protein

<400> SEQUENCE: 9

Met Glu Thr Asp Thr Leu Leu Leu Trp Val Leu Leu Leu Trp Val Pro
1               5                   10                  15

Gly Ser Thr Gly Asp Phe Arg Glu Leu Gly Tyr Val Leu Lys Asp Lys
                20                  25                  30

Tyr Asn Glu Ala Val His Val Glu Pro Val Arg Ala Ser Arg Asn Lys
            35                  40                  45

Arg Pro Thr Phe Leu Lys Ile Lys Lys Pro Leu Ser Tyr Arg Lys Pro
        50                  55                  60

Met Asp Thr Asp Leu Val Tyr Ile Glu Lys Ser Pro Asn Tyr Cys Glu
65                  70                  75                  80

Glu Asp Pro Val Thr Gly Ser Val Gly Thr Gln Gly Arg Ala Cys Asn
                85                  90                  95

Lys Thr Ala Pro Gln Ala Ser Gly Cys Asp Leu Met Cys Cys Gly Arg
            100                 105                 110

Gly Tyr Asn Thr His Gln Tyr Ala Arg Val Trp Gln Cys Asn Cys Lys
        115                 120                 125

Phe His Trp Cys Cys Tyr Val Lys Cys Asn Thr Cys Ser Glu Arg Thr
    130                 135                 140

Glu Met Tyr Thr Cys Lys Glu Asn Leu Tyr Phe Gln Gly Gly Gly Asp
145                 150                 155                 160

Tyr Lys Asp Asp Asp Asp Lys
                165

<210> SEQ ID NO 10
<211> LENGTH: 149
<212> TYPE: PRT
<213> ORGANISM: Artificial Sequence
<220> FEATURE:
<223> OTHER INFORMATION: Fusion Protein

<400> SEQUENCE: 10

Met Pro Leu Leu Leu Leu Leu Pro Leu Leu Trp Ala Gly Ala Leu Ala
1               5                   10                  15

Met Asp Ala Val His Val Glu Pro Val Arg Ala Ser Arg Asn Lys Arg
                20                  25                  30

Pro Thr Phe Leu Lys Ile Lys Lys Pro Leu Ser Tyr Arg Lys Pro Met
            35                  40                  45

Asp Thr Asp Leu Val Tyr Ile Glu Lys Ser Pro Asn Tyr Cys Glu Glu
        50                  55                  60

Asp Pro Val Thr Gly Ser Val Gly Thr Gln Gly Arg Ala Cys Asn Lys
65                  70                  75                  80

Thr Ala Pro Gln Ala Ser Gly Cys Asp Leu Met Cys Cys Gly Arg Gly
                85                  90                  95
```

```
Tyr Asn Thr His Gln Tyr Ala Arg Val Trp Gln Cys Asn Cys Lys Phe
            100                 105                 110

His Trp Cys Cys Tyr Val Lys Cys Asn Thr Cys Ser Glu Arg Thr Glu
        115                 120                 125

Met Tyr Thr Cys Lys Glu Asn Leu Tyr Phe Gln Gly Gly Gly Ser His
130                 135                 140

His His His His His
145

<210> SEQ ID NO 11
<211> LENGTH: 150
<212> TYPE: PRT
<213> ORGANISM: Artificial Sequence
<220> FEATURE:
<223> OTHER INFORMATION: Fusion Protein

<400> SEQUENCE: 11

Met Pro Leu Leu Leu Leu Pro Leu Leu Trp Ala Gly Ala Leu Ala
1               5                   10                  15

Met Asp Ala Val His Val Glu Pro Val Arg Ala Ser Arg Asn Lys Arg
                20                  25                  30

Pro Thr Phe Leu Lys Ile Lys Lys Pro Leu Ser Tyr Arg Lys Pro Met
            35                  40                  45

Asp Thr Asp Leu Val Tyr Ile Glu Lys Ser Pro Asn Tyr Cys Glu Glu
50                  55                  60

Asp Pro Val Thr Gly Ser Val Gly Thr Gln Gly Arg Ala Cys Asn Lys
65                  70                  75                  80

Thr Ala Pro Gln Ala Ser Gly Cys Asp Leu Met Cys Cys Gly Arg Gly
                85                  90                  95

Tyr Asn Thr His Gln Tyr Ala Arg Val Trp Gln Cys Asn Cys Lys Phe
            100                 105                 110

His Trp Cys Cys Tyr Val Lys Cys Asn Thr Cys Ser Glu Arg Thr Glu
        115                 120                 125

Met Tyr Thr Cys Lys Glu Asn Leu Tyr Phe Gln Gly Gly Gly Asp Tyr
130                 135                 140

Lys Asp Asp Asp Lys
145                 150

<210> SEQ ID NO 12
<211> LENGTH: 152
<212> TYPE: PRT
<213> ORGANISM: Artificial Sequence
<220> FEATURE:
<223> OTHER INFORMATION: Fusion Protein

<400> SEQUENCE: 12

Met Glu Thr Asp Thr Leu Leu Leu Trp Val Leu Leu Leu Trp Val Pro
1               5                   10                  15

Gly Ser Thr Gly Asp Ala Val His Val Glu Pro Val Arg Ala Ser Arg
                20                  25                  30

Asn Lys Arg Pro Thr Phe Leu Lys Ile Lys Lys Pro Leu Ser Tyr Arg
            35                  40                  45

Lys Pro Met Asp Thr Asp Leu Val Tyr Ile Glu Lys Ser Pro Asn Tyr
        50                  55                  60

Cys Glu Glu Asp Pro Val Thr Gly Ser Val Gly Thr Gln Gly Arg Ala
65                  70                  75                  80

Cys Asn Lys Thr Ala Pro Gln Ala Ser Gly Cys Asp Leu Met Cys Cys
                85                  90                  95
```

Gly Arg Gly Tyr Asn Thr His Gln Tyr Ala Arg Val Trp Gln Cys Asn
                100                 105                 110

Cys Lys Phe His Trp Cys Cys Tyr Val Lys Cys Asn Thr Cys Ser Glu
            115                 120                 125

Arg Thr Glu Met Tyr Thr Cys Lys Glu Asn Leu Tyr Phe Gln Gly Gly
        130                 135                 140

Gly Ser His His His His His His
145                 150

<210> SEQ ID NO 13
<211> LENGTH: 153
<212> TYPE: PRT
<213> ORGANISM: Artificial Sequence
<220> FEATURE:
<223> OTHER INFORMATION: Fusion Protein

<400> SEQUENCE: 13

Met Glu Thr Asp Thr Leu Leu Leu Trp Val Leu Leu Leu Trp Val Pro
1               5                   10                  15

Gly Ser Thr Gly Asp Ala Val His Val Glu Pro Val Arg Ala Ser Arg
            20                  25                  30

Asn Lys Arg Pro Thr Phe Leu Lys Ile Lys Lys Pro Leu Ser Tyr Arg
        35                  40                  45

Lys Pro Met Asp Thr Asp Leu Val Tyr Ile Glu Lys Ser Pro Asn Tyr
    50                  55                  60

Cys Glu Glu Asp Pro Val Thr Gly Ser Val Gly Thr Gln Gly Arg Ala
65                  70                  75                  80

Cys Asn Lys Thr Ala Pro Gln Ala Ser Gly Cys Asp Leu Met Cys Cys
                85                  90                  95

Gly Arg Gly Tyr Asn Thr His Gln Tyr Ala Arg Val Trp Gln Cys Asn
                100                 105                 110

Cys Lys Phe His Trp Cys Cys Tyr Val Lys Cys Asn Thr Cys Ser Glu
            115                 120                 125

Arg Thr Glu Met Tyr Thr Cys Lys Glu Asn Leu Tyr Phe Gln Gly Gly
        130                 135                 140

Gly Asp Tyr Lys Asp Asp Asp Lys
145                 150

<210> SEQ ID NO 14
<211> LENGTH: 120
<212> TYPE: PRT
<213> ORGANISM: Artificial Sequence
<220> FEATURE:
<223> OTHER INFORMATION: Fusion Protein

<400> SEQUENCE: 14

Met Pro Leu Leu Leu Leu Leu Pro Leu Leu Trp Ala Gly Ala Leu Ala
1               5                   10                  15

Met Asp Met Asp Thr Asp Leu Val Tyr Ile Glu Lys Ser Pro Asn Tyr
            20                  25                  30

Cys Glu Glu Asp Pro Val Thr Gly Ser Val Gly Thr Gln Gly Arg Ala
        35                  40                  45

Cys Asn Lys Thr Ala Pro Gln Ala Ser Gly Cys Asp Leu Met Cys Cys
    50                  55                  60

Gly Arg Gly Tyr Asn Thr His Gln Tyr Ala Arg Val Trp Gln Cys Asn
65                  70                  75                  80

Cys Lys Phe His Trp Cys Cys Tyr Val Lys Cys Asn Thr Cys Ser Glu

```
              85                  90                  95
Arg Thr Glu Met Tyr Thr Cys Lys Glu Asn Leu Tyr Phe Gln Gly Gly
            100                 105                 110

Gly Ser His His His His His His
        115                 120

<210> SEQ ID NO 15
<211> LENGTH: 121
<212> TYPE: PRT
<213> ORGANISM: Artificial Sequence
<220> FEATURE:
<223> OTHER INFORMATION: Fusion Protein

<400> SEQUENCE: 15

Met Pro Leu Leu Leu Leu Pro Leu Leu Trp Ala Gly Ala Leu Ala
1               5                  10                  15

Met Asp Met Asp Thr Asp Leu Val Tyr Ile Glu Lys Ser Pro Asn Tyr
            20                  25                  30

Cys Glu Glu Asp Pro Val Thr Gly Ser Val Gly Thr Gln Gly Arg Ala
        35                  40                  45

Cys Asn Lys Thr Ala Pro Gln Ala Ser Gly Cys Asp Leu Met Cys Cys
    50                  55                  60

Gly Arg Gly Tyr Asn Thr His Gln Tyr Ala Arg Val Trp Gln Cys Asn
65                  70                  75                  80

Cys Lys Phe His Trp Cys Cys Tyr Val Lys Cys Asn Thr Cys Ser Glu
                85                  90                  95

Arg Thr Glu Met Tyr Thr Cys Lys Glu Asn Leu Tyr Phe Gln Gly Gly
            100                 105                 110

Gly Asp Tyr Lys Asp Asp Asp Lys
        115                 120

<210> SEQ ID NO 16
<211> LENGTH: 123
<212> TYPE: PRT
<213> ORGANISM: Artificial Sequence
<220> FEATURE:
<223> OTHER INFORMATION: Fusion Protein

<400> SEQUENCE: 16

Met Glu Thr Asp Thr Leu Leu Leu Trp Val Leu Leu Leu Trp Val Pro
1               5                  10                  15

Gly Ser Thr Gly Asp Met Asp Thr Asp Leu Val Tyr Ile Glu Lys Ser
            20                  25                  30

Pro Asn Tyr Cys Glu Glu Asp Pro Val Thr Gly Ser Val Gly Thr Gln
        35                  40                  45

Gly Arg Ala Cys Asn Lys Thr Ala Pro Gln Ala Ser Gly Cys Asp Leu
    50                  55                  60

Met Cys Cys Gly Arg Gly Tyr Asn Thr His Gln Tyr Ala Arg Val Trp
65                  70                  75                  80

Gln Cys Asn Cys Lys Phe His Trp Cys Cys Tyr Val Lys Cys Asn Thr
                85                  90                  95

Cys Ser Glu Arg Thr Glu Met Tyr Thr Cys Lys Glu Asn Leu Tyr Phe
            100                 105                 110

Gln Gly Gly Gly Ser His His His His His
        115                 120

<210> SEQ ID NO 17
<211> LENGTH: 124
```

<212> TYPE: PRT
<213> ORGANISM: Artificial Sequence
<220> FEATURE:
<223> OTHER INFORMATION: Fusion Protein

<400> SEQUENCE: 17

Met Glu Thr Asp Thr Leu Leu Leu Trp Val Leu Leu Trp Val Pro
1               5                   10                  15

Gly Ser Thr Gly Asp Met Asp Thr Asp Leu Val Tyr Ile Glu Lys Ser
            20                  25                  30

Pro Asn Tyr Cys Glu Glu Asp Pro Val Thr Gly Ser Val Gly Thr Gln
                35                  40                  45

Gly Arg Ala Cys Asn Lys Thr Ala Pro Gln Ala Ser Gly Cys Asp Leu
50                  55                  60

Met Cys Cys Gly Arg Gly Tyr Asn Thr His Gln Tyr Ala Arg Val Trp
65                  70                  75                  80

Gln Cys Asn Cys Lys Phe His Trp Cys Cys Tyr Val Lys Cys Asn Thr
                85                  90                  95

Cys Ser Glu Arg Thr Glu Met Tyr Thr Cys Lys Glu Asn Leu Tyr Phe
            100                 105                 110

Gln Gly Gly Gly Asp Tyr Lys Asp Asp Asp Lys
        115                 120

<210> SEQ ID NO 18
<211> LENGTH: 349
<212> TYPE: PRT
<213> ORGANISM: Mus musculus

<400> SEQUENCE: 18

Met Thr Arg Lys Ala Arg Arg Cys Leu Gly His Leu Phe Leu Ser Leu
1               5                   10                  15

Gly Ile Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
                35                  40                  45

Arg Ala Ile Cys Gln Ser Arg Pro Asp Ala Ile Ile Val Ile Gly Glu
50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu

```
                   210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
                275                 280                 285

Thr Gln Gly Arg Ala Cys Asn Lys Thr Ala Pro Gln Ala Ser Gly Cys
                290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
                340                 345

<210> SEQ ID NO 19
<211> LENGTH: 349
<212> TYPE: PRT
<213> ORGANISM: Rattus norvegicus

<400> SEQUENCE: 19

Met Thr Arg Lys Ala Arg Arg Cys Leu Gly His Leu Phe Leu Ser Leu
1               5                   10                  15

Gly Ile Val Tyr Leu Arg Ile Gly Asp Phe Ser Ser Val Val Ala Leu
                20                  25                  30

Gly Ala Ser Ile Ile Cys Asn Lys Ile Pro Gly Leu Ala Pro Arg Gln
                35                  40                  45

Arg Ala Ile Cys Gln Ser Arg Pro Asp Ala Ile Ile Val Ile Gly Glu
                50                  55                  60

Gly Ser Gln Met Gly Leu Asp Glu Cys Gln Phe Gln Phe Arg Asn Gly
65              70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
                100                 105                 110

Ala Gly Val Ala His Ala Ile Thr Ala Ala Cys Thr Gln Gly Asn Leu
                115                 120                 125

Ser Asp Cys Gly Cys Asp Lys Glu Lys Gln Gly Gln Tyr His Arg Asp
                130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
                180                 185                 190

Glu Glu Asn Met Lys Leu Glu Cys Lys Cys His Gly Val Ser Gly Ser
                195                 200                 205

Cys Thr Thr Lys Thr Cys Trp Thr Thr Leu Pro Gln Phe Arg Glu Leu
                210                 215                 220

Gly Tyr Val Leu Lys Asp Lys Tyr Asn Glu Ala Val His Val Glu Pro
225                 230                 235                 240
```

Val Arg Ala Ser Arg Asn Lys Arg Pro Thr Phe Leu Lys Ile Lys Lys
            245                 250                 255

Pro Leu Ser Tyr Arg Lys Pro Met Asp Thr Asp Leu Val Tyr Ile Glu
        260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
        290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 20
<211> LENGTH: 349
<212> TYPE: PRT
<213> ORGANISM: Gallus gallus

<400> SEQUENCE: 20

Met Asn Arg Lys Thr Arg Arg Trp Ile Phe His Ile Phe Leu Ser Leu
1               5                   10                  15

Gly Ile Val Tyr Ile Lys Ile Gly Gly Phe Ser Ser Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Ile Asn Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Lys Glu
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Lys Phe Arg Glu Leu
    210                 215                 220

Gly Tyr Ile Leu Lys Asp Lys Tyr Asn Glu Ala Val Gln Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

```
Lys Ser Pro Asn Tyr Cys Glu Glu Asp Pro Val Thr Gly Ser Val Gly
            275                 280                 285

Thr Gln Gly Arg Met Cys Asn Lys Thr Ala Gln Gln Ser Asn Gly Cys
            290                 295                 300

Asp Leu Met Cys Cys Gly Arg Gly Tyr Asn Thr His Gln Tyr Ser Arg
305                 310                 315                 320

Val Trp Gln Cys Asn Cys Lys Phe His Trp Cys Cys Tyr Val Lys Cys
                    325                 330                 335

Asn Thr Cys Ser Glu Arg Thr Glu Val Tyr Thr Cys Lys
            340                 345

<210> SEQ ID NO 21
<211> LENGTH: 349
<212> TYPE: PRT
<213> ORGANISM: Danio rerio

<400> SEQUENCE: 21

Met Ser Arg Lys Thr Arg Arg Trp Ile Phe His Ile Phe Leu Cys Leu
1               5                   10                  15

Gly Ile Ile Tyr Leu Lys Ile Gly Gly Phe Ser Ser Val Val Ala Leu
            20                  25                  30

Gly Ala Ser Ile Ile Cys Asn Lys Ile Pro Gly Leu Ala Pro Arg Gln
            35                  40                  45

Arg Thr Ile Cys Gln Ser Arg Pro Asp Ala Ile Ile Val Ile Gly Glu
            50                  55                  60

Gly Ala Gln Met Gly Ile Asn Glu Cys Gln Phe Gln Phe Lys Asn Gly
65              70                  75                  80

Arg Trp Asn Cys Ser Ala Leu Gly Glu Arg Thr Val Phe Gly Lys Glu
                85                  90                  95

Leu Lys Val Gly Ser Lys Glu Ala Ala Phe Thr Tyr Ala Ile Ile Ala
            100                 105                 110

Ala Gly Val Ala His Ala Ile Thr Ala Ala Cys Thr Gln Gly Thr Leu
            115                 120                 125

Ser Gly Cys Gly Cys Asp Lys Glu Lys Gln Gly Phe Tyr Asn Gln Glu
            130                 135                 140

Glu Gly Trp Lys Trp Gly Gly Cys Ser Ala Asp Ile Arg Tyr Gly Leu
145                 150                 155                 160

Ser Phe Ser Lys Val Phe Leu Asp Ala Arg Glu Ile Lys Gln Asn Ala
                165                 170                 175

Arg Thr Leu Met Asn Leu His Asn Asn Glu Val Gly Arg Lys Ile Leu
            180                 185                 190

Glu Lys Asn Met Arg Leu Glu Cys Lys Cys His Gly Val Ser Gly Ser
            195                 200                 205

Cys Thr Thr Lys Thr Cys Trp Thr Thr Leu Pro Lys Phe Arg Gln Leu
210                 215                 220

Gly Tyr Ile Leu Lys Glu Arg Tyr Asn His Ala Val His Val Glu Pro
225                 230                 235                 240

Val Arg Ala Ser Arg Asn Lys Arg Pro Ala Phe Leu Lys Val Lys Lys
                245                 250                 255

Pro Tyr Ser Tyr Arg Lys Pro Met Asp Thr Asp Leu Val Tyr Ile Glu
            260                 265                 270

Lys Ser Pro Asn Tyr Cys Glu Ala Asp Pro Val Thr Gly Ser Met Gly
            275                 280                 285

Thr Gln Gly Arg Ile Cys Asn Lys Thr Ala Gln His Thr Asn Gly Cys
```

```
            290                 295                 300
Asp Leu Met Cys Cys Gly Arg Gly Tyr Asn Thr His Gln Tyr Ser Arg
305                 310                 315                 320

Val Trp Gln Cys Asn Cys Lys Phe Leu Trp Cys Cys Tyr Val Lys Cys
                325                 330                 335

Asn Thr Cys Ser Glu Arg Thr Glu Val Tyr Thr Cys Lys
            340                 345
```

<210> SEQ ID NO 22
<211> LENGTH: 349
<212> TYPE: PRT
<213> ORGANISM: Sus scrofa

<400> SEQUENCE: 22

```
Met Asn Arg Lys Ala Arg Arg Cys Leu Gly His Leu Phe Leu Ser Leu
1               5                   10                  15

Gly Leu Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Val Ile Gly Glu
    50                  55                  60

Gly Ser Gln Met Gly Leu Asp Glu Cys Gln Phe Gln Phe Arg Asn Gly
65              70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
290                 295                 300

Asp Leu Met Cys Cys Gly Arg Gly Tyr Asn Thr His Gln Tyr Ala Arg
305                 310                 315                 320
```

Val Trp Gln Cys Asn Cys Lys Phe His Trp Cys Cys Tyr Val Lys Cys
                325                 330                 335

Asn Thr Cys Ser Glu Arg Thr Glu Val Tyr Thr Cys Lys
            340                 345

<210> SEQ ID NO 23
<211> LENGTH: 349
<212> TYPE: PRT
<213> ORGANISM: Bos taurus

<400> SEQUENCE: 23

Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Ala Phe Leu Lys Ile Lys Lys
                245                 250                 255

Pro Leu Ser Tyr Arg Lys Pro Met Asp Thr Glu Leu Val Tyr Ile Glu
            260                 265                 270

Lys Ser Pro Ser Tyr Cys Glu Glu Asp Pro Ala Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Val Tyr Thr Cys Lys
            340                 345

<210> SEQ ID NO 24
<211> LENGTH: 29
<212> TYPE: DNA
<213> ORGANISM: Artificial Sequence
<220> FEATURE:
<223> OTHER INFORMATION: Polynucleotide sequences used to construct Wnt
      expression vectors

<400> SEQUENCE: 24
gcatcatatg gccgttcacg tggagcctg                                    29

<210> SEQ ID NO 25
<211> LENGTH: 34
<212> TYPE: DNA
<213> ORGANISM: Artificial Sequence
<220> FEATURE:
<223> OTHER INFORMATION: Polynucleotide sequences used to construct Wnt
      expression vectors

<400> SEQUENCE: 25
gcatgcggcc gctcacttgc acgtgtacat ctcc                              34

<210> SEQ ID NO 26
<211> LENGTH: 28
<212> TYPE: DNA
<213> ORGANISM: Artificial Sequence
<220> FEATURE:
<223> OTHER INFORMATION: Polynucleotide sequences used to construct Wnt
      expression vectors

<400> SEQUENCE: 26
gcatccatgg ccgttcacgt ggagcctg                                     28

<210> SEQ ID NO 27
<211> LENGTH: 54
<212> TYPE: DNA
<213> ORGANISM: Homo sapiens

<400> SEQUENCE: 27
atgcccctgc tgctgctcct ccctctgctg tgggctggcg ctctggccat ggat        54

<210> SEQ ID NO 28
<211> LENGTH: 18
<212> TYPE: PRT
<213> ORGANISM: Homo sapiens

<400> SEQUENCE: 28

Met Pro Leu Leu Leu Leu Leu Pro Leu Leu Trp Ala Gly Ala Leu Ala
1               5                   10                  15

Met Asp

<210> SEQ ID NO 29
<211> LENGTH: 63
<212> TYPE: DNA
<213> ORGANISM: Homo sapiens

<400> SEQUENCE: 29
atggagacag acacactcct gctatgggta ctgctgctct gggttccagg ttccactggt    60
gac                                                                  63

<210> SEQ ID NO 30
<211> LENGTH: 21
<212> TYPE: PRT

<213> ORGANISM: Homo sapiens

<400> SEQUENCE: 30

Met Glu Thr Asp Thr Leu Leu Leu Trp Val Leu Leu Leu Trp Val Pro
1               5                   10                  15

Gly Ser Thr Gly Asp
            20

<210> SEQ ID NO 31
<211> LENGTH: 147
<212> TYPE: PRT
<213> ORGANISM: Artificial Sequence
<220> FEATURE:
<223> OTHER INFORMATION: Fusion polypeptide comprising amino acid
      221-349 of human Wnt7a

<400> SEQUENCE: 31

Met Pro Leu Leu Leu Leu Leu Pro Leu Leu Trp Ala Gly Ala Leu Ala
1               5                   10                  15

Met Asp Phe Arg Glu Leu Gly Tyr Val Leu Lys Asp Lys Tyr Asn Glu
            20                  25                  30

Ala Val His Val Glu Pro Val Arg Ala Ser Arg Asn Lys Arg Pro Thr
        35                  40                  45

Phe Leu Lys Ile Lys Lys Pro Leu Ser Tyr Arg Lys Pro Met Asp Thr
    50                  55                  60

Asp Leu Val Tyr Ile Glu Lys Ser Pro Asn Tyr Cys Glu Glu Asp Pro
65                  70                  75                  80

Val Thr Gly Ser Val Gly Thr Gln Gly Arg Ala Cys Asn Lys Thr Ala
                85                  90                  95

Pro Gln Ala Ser Gly Cys Asp Leu Met Cys Cys Gly Arg Gly Tyr Asn
            100                 105                 110

Thr His Gln Tyr Ala Arg Val Trp Gln Cys Asn Cys Lys Phe His Trp
        115                 120                 125

Cys Cys Tyr Val Lys Cys Asn Thr Cys Ser Glu Arg Thr Glu Met Tyr
    130                 135                 140

Thr Cys Lys
145

<210> SEQ ID NO 32
<211> LENGTH: 150
<212> TYPE: PRT
<213> ORGANISM: Artificial Sequence
<220> FEATURE:
<223> OTHER INFORMATION: Fusion polypeptide comprising amino acid
      221-349 of human Wnt7a

<400> SEQUENCE: 32

Met Glu Thr Asp Thr Leu Leu Leu Trp Val Leu Leu Leu Trp Val Pro
1               5                   10                  15

Gly Ser Thr Gly Asp Phe Arg Glu Leu Gly Tyr Val Leu Lys Asp Lys
            20                  25                  30

Tyr Asn Glu Ala Val His Val Glu Pro Val Arg Ala Ser Arg Asn Lys
        35                  40                  45

Arg Pro Thr Phe Leu Lys Ile Lys Lys Pro Leu Ser Tyr Arg Lys Pro
    50                  55                  60

Met Asp Thr Asp Leu Val Tyr Ile Glu Lys Ser Pro Asn Tyr Cys Glu
65                  70                  75                  80

Glu Asp Pro Val Thr Gly Ser Val Gly Thr Gln Gly Arg Ala Cys Asn
                85                  90                  95

Lys Thr Ala Pro Gln Ala Ser Gly Cys Asp Leu Met Cys Cys Gly Arg
            100                 105                 110

Gly Tyr Asn Thr His Gln Tyr Ala Arg Val Trp Gln Cys Asn Cys Lys
        115                 120                 125

Phe His Trp Cys Cys Tyr Val Lys Cys Asn Thr Cys Ser Glu Arg Thr
    130                 135                 140

Glu Met Tyr Thr Cys Lys
145             150

<210> SEQ ID NO 33
<211> LENGTH: 133
<212> TYPE: PRT
<213> ORGANISM: Artificial Sequence
<220> FEATURE:
<223> OTHER INFORMATION: Fusion polypeptide comprising amino acid
      235-349 of human Wnt7a

<400> SEQUENCE: 33

Met Pro Leu Leu Leu Leu Pro Leu Leu Trp Ala Gly Ala Leu Ala
1               5                   10                  15

Met Asp Ala Val His Val Glu Pro Val Arg Ala Ser Arg Asn Lys Arg
            20                  25                  30

Pro Thr Phe Leu Lys Ile Lys Lys Pro Leu Ser Tyr Arg Lys Pro Met
        35                  40                  45

Asp Thr Asp Leu Val Tyr Ile Glu Lys Ser Pro Asn Tyr Cys Glu Glu
    50                  55                  60

Asp Pro Val Thr Gly Ser Val Gly Thr Gln Gly Arg Ala Cys Asn Lys
65                  70                  75                  80

Thr Ala Pro Gln Ala Ser Gly Cys Asp Leu Met Cys Cys Gly Arg Gly
                85                  90                  95

Tyr Asn Thr His Gln Tyr Ala Arg Val Trp Gln Cys Asn Cys Lys Phe
            100                 105                 110

His Trp Cys Cys Tyr Val Lys Cys Asn Thr Cys Ser Glu Arg Thr Glu
        115                 120                 125

Met Tyr Thr Cys Lys
    130

<210> SEQ ID NO 34
<211> LENGTH: 136
<212> TYPE: PRT
<213> ORGANISM: Artificial Sequence
<220> FEATURE:
<223> OTHER INFORMATION: Fusion polypeptide comprising amino acid
      235-349 of human Wnt7a

<400> SEQUENCE: 34

Met Glu Thr Asp Thr Leu Leu Leu Trp Val Leu Leu Leu Trp Val Pro
1               5                   10                  15

Gly Ser Thr Gly Asp Ala Val His Val Glu Pro Val Arg Ala Ser Arg
            20                  25                  30

Asn Lys Arg Pro Thr Phe Leu Lys Ile Lys Lys Pro Leu Ser Tyr Arg
        35                  40                  45

Lys Pro Met Asp Thr Asp Leu Val Tyr Ile Glu Lys Ser Pro Asn Tyr
    50                  55                  60

Cys Glu Glu Asp Pro Val Thr Gly Ser Val Gly Thr Gln Gly Arg Ala
65                  70                  75                  80

Cys Asn Lys Thr Ala Pro Gln Ala Ser Gly Cys Asp Leu Met Cys Cys
                85                  90                  95

```
Gly Arg Gly Tyr Asn Thr His Gln Tyr Ala Arg Val Trp Gln Cys Asn
            100                 105                 110

Cys Lys Phe His Trp Cys Cys Tyr Val Lys Cys Asn Thr Cys Ser Glu
        115                 120                 125

Arg Thr Glu Met Tyr Thr Cys Lys
        130                 135

<210> SEQ ID NO 35
<211> LENGTH: 104
<212> TYPE: PRT
<213> ORGANISM: Artificial Sequence
<220> FEATURE:
<223> OTHER INFORMATION: Fusion polypeptide comprising amino acid
      264-349 of human Wnt7a

<400> SEQUENCE: 35

Met Pro Leu Leu Leu Leu Pro Leu Leu Trp Ala Gly Ala Leu Ala
1               5                   10                  15

Met Asp Met Asp Thr Asp Leu Val Tyr Ile Glu Lys Ser Pro Asn Tyr
            20                  25                  30

Cys Glu Glu Asp Pro Val Thr Gly Ser Val Gly Thr Gln Gly Arg Ala
        35                  40                  45

Cys Asn Lys Thr Ala Pro Gln Ala Ser Gly Cys Asp Leu Met Cys Cys
    50                  55                  60

Gly Arg Gly Tyr Asn Thr His Gln Tyr Ala Arg Val Trp Gln Cys Asn
65                  70                  75                  80

Cys Lys Phe His Trp Cys Cys Tyr Val Lys Cys Asn Thr Cys Ser Glu
                85                  90                  95

Arg Thr Glu Met Tyr Thr Cys Lys
                100

<210> SEQ ID NO 36
<211> LENGTH: 107
<212> TYPE: PRT
<213> ORGANISM: Artificial Sequence
<220> FEATURE:
<223> OTHER INFORMATION: Fusion polypeptide comprising amino acid
      264-349 of human Wnt7a

<400> SEQUENCE: 36

Met Glu Thr Asp Thr Leu Leu Leu Trp Val Leu Leu Leu Trp Val Pro
1               5                   10                  15

Gly Ser Thr Gly Asp Met Asp Thr Asp Leu Val Tyr Ile Glu Lys Ser
            20                  25                  30

Pro Asn Tyr Cys Glu Glu Asp Pro Val Thr Gly Ser Val Gly Thr Gln
        35                  40                  45

Gly Arg Ala Cys Asn Lys Thr Ala Pro Gln Ala Ser Gly Cys Asp Leu
    50                  55                  60

Met Cys Cys Gly Arg Gly Tyr Asn Thr His Gln Tyr Ala Arg Val Trp
65                  70                  75                  80

Gln Cys Asn Cys Lys Phe His Trp Cys Cys Tyr Val Lys Cys Asn Thr
                85                  90                  95

Cys Ser Glu Arg Thr Glu Met Tyr Thr Cys Lys
                100                 105

<210> SEQ ID NO 37
<211> LENGTH: 376
<212> TYPE: PRT
<213> ORGANISM: Artificial Sequence
```

<220> FEATURE:
<223> OTHER INFORMATION: Fusion protein, CD33 Leader, 235-349, Linker, FC-Domain

<400> SEQUENCE: 37

| | | | | | | | | | | | | | | |
|---|---|---|---|---|---|---|---|---|---|---|---|---|---|---|
| Met | Pro | Leu | Leu | Leu | Leu | Pro | Leu | Leu | Trp | Ala | Gly | Ala | Leu | Ala |
| 1 | | | 5 | | | | | 10 | | | | | 15 | |
| Met | Asp | Ala | Val | His | Val | Glu | Pro | Val | Arg | Ala | Ser | Arg | Asn | Lys | Arg |
| | | 20 | | | | | 25 | | | | | 30 | | |
| Pro | Thr | Phe | Leu | Lys | Ile | Lys | Lys | Pro | Leu | Ser | Tyr | Arg | Lys | Pro | Met |
| | | 35 | | | | 40 | | | | | 45 | | | | |
| Asp | Thr | Asp | Leu | Val | Tyr | Ile | Glu | Lys | Ser | Pro | Asn | Tyr | Cys | Glu | Glu |
| | 50 | | | | | 55 | | | | | 60 | | | | |
| Asp | Pro | Val | Thr | Gly | Ser | Val | Gly | Thr | Gln | Gly | Arg | Ala | Cys | Asn | Lys |
| 65 | | | | 70 | | | | | 75 | | | | | 80 | |
| Thr | Ala | Pro | Gln | Ala | Ser | Gly | Cys | Asp | Leu | Met | Cys | Cys | Gly | Arg | Gly |
| | | | | 85 | | | | 90 | | | | | 95 | | |
| Tyr | Asn | Thr | His | Gln | Tyr | Ala | Arg | Val | Trp | Gln | Cys | Asn | Cys | Lys | Phe |
| | | | 100 | | | | | 105 | | | | | 110 | | |
| His | Trp | Cys | Cys | Tyr | Val | Lys | Cys | Asn | Thr | Cys | Ser | Glu | Arg | Thr | Glu |
| | | | 115 | | | | | 120 | | | | | 125 | | |
| Met | Tyr | Thr | Cys | Lys | Gly | Thr | Gly | Gly | Gly | Ser | Gly | Gly | Gly | Gly |
| | 130 | | | | | 135 | | | | | 140 | | | | |
| Ser | Gly | Gly | Gly | Gly | Ser | Asp | Lys | Thr | His | Thr | Cys | Pro | Pro | Cys | Pro |
| 145 | | | | | 150 | | | | | 155 | | | | | 160 |
| Ala | Pro | Pro | Val | Ala | Gly | Pro | Ser | Val | Phe | Leu | Phe | Pro | Pro | Lys | Pro |
| | | | | 165 | | | | | 170 | | | | | 175 | |
| Lys | Asp | Thr | Leu | Met | Ile | Ser | Arg | Thr | Pro | Glu | Val | Thr | Cys | Val | Val |
| | | | 180 | | | | | 185 | | | | | 190 | | |
| Val | Asp | Val | Ser | His | Glu | Asp | Pro | Glu | Val | Lys | Phe | Asn | Trp | Tyr | Val |
| | | | 195 | | | | | 200 | | | | | 205 | | |
| Asp | Gly | Val | Glu | Val | His | Asn | Ala | Lys | Thr | Lys | Pro | Arg | Glu | Glu | Gln |
| | | 210 | | | | | 215 | | | | | 220 | | | |
| Tyr | Asn | Ser | Thr | Tyr | Arg | Val | Val | Ser | Val | Leu | Thr | Val | Leu | His | Gln |
| 225 | | | | | 230 | | | | | 235 | | | | | 240 |
| Asp | Trp | Leu | Asn | Gly | Lys | Glu | Tyr | Lys | Cys | Lys | Val | Ser | Asn | Lys | Gly |
| | | | | 245 | | | | | 250 | | | | | 255 | |
| Leu | Pro | Ser | Ser | Ile | Glu | Lys | Thr | Ile | Ser | Lys | Ala | Lys | Gly | Gln | Pro |
| | | | 260 | | | | | 265 | | | | | 270 | | |
| Arg | Glu | Pro | Gln | Val | Tyr | Thr | Leu | Pro | Pro | Ser | Arg | Glu | Glu | Met | Thr |
| | | 275 | | | | | 280 | | | | | 285 | | | |
| Lys | Asn | Gln | Val | Ser | Leu | Thr | Cys | Leu | Val | Lys | Gly | Phe | Tyr | Pro | Ser |
| | 290 | | | | | 295 | | | | | 300 | | | | |
| Asp | Ile | Ala | Val | Glu | Trp | Glu | Ser | Asn | Gly | Gln | Pro | Glu | Asn | Asn | Tyr |
| 305 | | | | | 310 | | | | | 315 | | | | | 320 |
| Lys | Thr | Thr | Pro | Pro | Val | Leu | Asp | Ser | Asp | Gly | Ser | Phe | Phe | Leu | Tyr |
| | | | | 325 | | | | | 330 | | | | | 335 | |
| Ser | Lys | Leu | Thr | Val | Asp | Lys | Ser | Arg | Trp | Gln | Gln | Gly | Asn | Val | Phe |
| | | | 340 | | | | | 345 | | | | | 350 | | |
| Ser | Cys | Ser | Val | Met | His | Glu | Ala | Leu | His | Asn | His | Tyr | Thr | Gln | Lys |
| | | | 355 | | | | | 360 | | | | | 365 | | |
| Ser | Leu | Ser | Leu | Ser | Pro | Gly | Lys |
| | | | 370 | | | | 375 |

<210> SEQ ID NO 38
<211> LENGTH: 379
<212> TYPE: PRT
<213> ORGANISM: Artificial Sequence
<220> FEATURE:
<223> OTHER INFORMATION: Fusion protein, IgG Kappa Leader, 235-349, Linker, FC-Domain

<400> SEQUENCE: 38

```
Met Glu Thr Asp Thr Leu Leu Leu Trp Val Leu Leu Trp Val Pro
1               5                   10                  15

Gly Ser Thr Gly Asp Ala Val His Val Glu Pro Val Arg Ala Ser Arg
            20                  25                  30

Asn Lys Arg Pro Thr Phe Leu Lys Ile Lys Pro Leu Ser Tyr Arg
            35                  40                  45

Lys Pro Met Asp Thr Asp Leu Val Tyr Ile Glu Lys Ser Pro Asn Tyr
50                  55                      60

Cys Glu Glu Asp Pro Val Thr Gly Ser Val Gly Thr Gln Gly Arg Ala
65                  70                  75                  80

Cys Asn Lys Thr Ala Pro Gln Ala Ser Gly Cys Asp Leu Met Cys Cys
                85                  90                  95

Gly Arg Gly Tyr Asn Thr His Gln Tyr Ala Arg Val Trp Gln Cys Asn
                100                 105                 110

Cys Lys Phe His Trp Cys Cys Tyr Val Lys Cys Asn Thr Cys Ser Glu
            115                 120                 125

Arg Thr Glu Met Tyr Thr Cys Lys Gly Thr Gly Gly Gly Ser Gly
            130                 135                 140

Gly Gly Gly Ser Gly Gly Gly Ser Asp Lys Thr His Thr Cys Pro
145                 150                 155                 160

Pro Cys Pro Ala Pro Pro Val Ala Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
            195                 200                 205

Trp Tyr Val Asp Gly Val Glu Val His Asn Ala Lys Thr Lys Pro Arg
            210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Gly Leu Pro Ser Ser Ile Glu Lys Thr Ile Ser Lys Ala Lys
                260                 265                 270

Gly Gln Pro Arg Glu Pro Gln Val Tyr Thr Leu Pro Pro Ser Arg Glu
            275                 280                 285

Glu Met Thr Lys Asn Gln Val Ser Leu Thr Cys Leu Val Lys Gly Phe
290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
            355                 360                 365
```

Thr Gln Lys Ser Leu Ser Leu Ser Pro Gly Lys
    370                 375

<210> SEQ ID NO 39
<211> LENGTH: 347
<212> TYPE: PRT
<213> ORGANISM: Artificial Sequence
<220> FEATURE:
<223> OTHER INFORMATION: Fusion protein, CD33 Leader, 264-349, Linker,
      FC-Domain

<400> SEQUENCE: 39

Met Pro Leu Leu Leu Leu Pro Leu Leu Trp Ala Gly Ala Leu Ala
1               5                   10                  15

Met Asp Met Asp Thr Asp Leu Val Tyr Ile Glu Lys Ser Pro Asn Tyr
            20                  25                  30

Cys Glu Glu Asp Pro Val Thr Gly Ser Val Gly Thr Gln Gly Arg Ala
        35                  40                  45

Cys Asn Lys Thr Ala Pro Gln Ala Ser Gly Cys Asp Leu Met Cys Cys
    50                  55                  60

Gly Arg Gly Tyr Asn Thr His Gln Tyr Ala Arg Val Trp Gln Cys Asn
65                  70                  75                  80

Cys Lys Phe His Trp Cys Cys Tyr Val Lys Cys Asn Thr Cys Ser Glu
                85                  90                  95

Arg Thr Glu Met Tyr Thr Cys Lys Gly Thr Gly Gly Gly Ser Gly
            100                 105                 110

Gly Gly Gly Ser Gly Gly Gly Ser Asp Lys Thr His Thr Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Lys Phe Asn
                165                 170                 175

Trp Tyr Val Asp Gly Val Glu Val His Asn Ala Lys Thr Lys Pro Arg
            180                 185                 190

Glu Glu Gln Tyr Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 40
<211> LENGTH: 350
<212> TYPE: PRT
<213> ORGANISM: Artificial Sequence
<220> FEATURE:
<223> OTHER INFORMATION: Fusion protein, IgG Kappa Leader, 264-349, Linker, FC-Domain

<400> SEQUENCE: 40

```
Met Glu Thr Asp Thr Leu Leu Leu Trp Val Leu Leu Leu Trp Val Pro
1               5                   10                  15

Gly Ser Thr Gly Asp Met Asp Thr Asp Leu Val Tyr Ile Glu Lys Ser
            20                  25                  30

Pro Asn Tyr Cys Glu Glu Asp Pro Val Thr Gly Ser Val Gly Thr Gln
            35                  40                  45

Gly Arg Ala Cys Asn Lys Thr Ala Pro Gln Ala Ser Gly Cys Asp Leu
        50                  55                  60

Met Cys Cys Gly Arg Gly Tyr Asn Thr His Gln Tyr Ala Arg Val Trp
65                  70                  75                  80

Gln Cys Asn Cys Lys Phe His Trp Cys Cys Tyr Val Lys Cys Asn Thr
                85                  90                  95

Cys Ser Glu Arg Thr Glu Met Tyr Thr Cys Lys Gly Thr Gly Gly Gly
            100                 105                 110

Gly Ser Gly Gly Gly Gly Ser Gly Gly Gly Gly Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350
```

```
<210> SEQ ID NO 41
<211> LENGTH: 383
<212> TYPE: PRT
<213> ORGANISM: Artificial Sequence
<220> FEATURE:
<223> OTHER INFORMATION: Fusion protein, CD33 Leader, FC-domain, linker,
      Tev, 235-349

<400> SEQUENCE: 41

Met Pro Leu Leu Leu Leu Pro Leu Leu Trp Ala Gly Ala Leu Ala
1               5                   10                  15

Met Asp Asp Lys Thr His Thr Cys Pro Pro Cys Pro Ala Pro Val
                20                  25                  30

Ala Gly Pro Ser Val Phe Leu Phe Pro Pro Lys Pro Lys Asp Thr Leu
                35                  40                  45

Met Ile Ser Arg Thr Pro Glu Val Thr Cys Val Val Val Asp Val Ser
            50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
                100                 105                 110

Gly Lys Glu Tyr Lys Cys Lys Val Ser Asn Lys Gly Leu Pro Ser Ser
                115                 120                 125

Ile Glu Lys Thr Ile Ser Lys Ala Lys Gly Gln Pro Arg Glu Pro Gln
                130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
                180                 185                 190

Pro Val Leu Asp Ser Asp Gly Ser Phe Phe Leu Tyr Ser Lys Leu Thr
                195                 200                 205

Val Asp Lys Ser Arg Trp Gln Gln Gly Asn Val Phe Ser Cys Ser Val
                210                 215                 220

Met His Glu Ala Leu His Asn His Tyr Thr Gln Lys Ser Leu Ser Leu
225                 230                 235                 240

Ser Pro Gly Lys Gly Thr Gly Gly Gly Ser Gly Gly Gly Ser
                245                 250                 255

Gly Gly Gly Gly Ser Glu Asn Leu Tyr Phe Gln Gly Ala Val His Val
                260                 265                 270

Glu Pro Val Arg Ala Ser Arg Asn Lys Arg Pro Thr Phe Leu Lys Ile
                275                 280                 285

Lys Lys Pro Leu Ser Tyr Arg Lys Pro Met Asp Thr Asp Leu Val Tyr
                290                 295                 300

Ile Glu Lys Ser Pro Asn Tyr Cys Glu Glu Asp Pro Val Thr Gly Ser
305                 310                 315                 320

Val Gly Thr Gln Gly Arg Ala Cys Asn Lys Thr Ala Pro Gln Ala Ser
                325                 330                 335

Gly Cys Asp Leu Met Cys Cys Gly Arg Gly Tyr Asn Thr His Gln Tyr
                340                 345                 350

Ala Arg Val Trp Gln Cys Asn Cys Lys Phe His Trp Cys Cys Tyr Val
                355                 360                 365
```

```
Lys Cys Asn Thr Cys Ser Glu Arg Thr Glu Met Tyr Thr Cys Lys
        370                 375                 380
```

```
<210> SEQ ID NO 42
<211> LENGTH: 387
<212> TYPE: PRT
<213> ORGANISM: Artificial Sequence
<220> FEATURE:
<223> OTHER INFORMATION: Fusion protein, IgG Kappa Leader, FC-domain,
      linker, Tev, 235-349

<400> SEQUENCE: 42

Met Glu Thr Asp Thr Leu Leu Leu Trp Val Leu Leu Trp Val Pro
1               5                   10                  15

Gly Ser Thr Gly Asp Ala Asp Lys Thr His Thr Cys Pro Pro Cys Pro
            20                  25                  30

Ala Pro Pro Val Ala Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Gly
        115                 120                 125

Leu Pro Ser Ser Ile Glu Lys Thr Ile Ser Lys Ala Lys Gly Gln Pro
    130                 135                 140

Arg Glu Pro Gln Val Tyr Thr Leu Pro Pro Ser Arg Glu Glu Met Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys Gly Thr Gly Gly Gly Ser Gly
                245                 250                 255

Gly Gly Gly Ser Gly Gly Gly Ser Glu Asn Leu Tyr Phe Gln Gly
            260                 265                 270

Ala Val His Val Glu Pro Val Arg Ala Ser Arg Asn Lys Arg Pro Thr
        275                 280                 285

Phe Leu Lys Ile Lys Lys Pro Leu Ser Tyr Arg Lys Pro Met Asp Thr
    290                 295                 300

Asp Leu Val Tyr Ile Glu Lys Ser Pro Asn Tyr Cys Glu Glu Asp Pro
305                 310                 315                 320

Val Thr Gly Ser Val Gly Thr Gln Gly Arg Ala Cys Asn Lys Thr Ala
                325                 330                 335

Pro Gln Ala Ser Gly Cys Asp Leu Met Cys Cys Gly Arg Gly Tyr Asn
            340                 345                 350
```

```
Thr His Gln Tyr Ala Arg Val Trp Gln Cys Asn Cys Lys Phe His Trp
        355                 360                 365

Cys Cys Tyr Val Lys Cys Asn Thr Cys Ser Glu Arg Thr Glu Met Tyr
        370                 375                 380

Thr Cys Lys
385

<210> SEQ ID NO 43
<211> LENGTH: 354
<212> TYPE: PRT
<213> ORGANISM: Artificial Sequence
<220> FEATURE:
<223> OTHER INFORMATION: Fusion protein, CD33 Leader, FC-domain, linker,
      Tev, 264-349

<400> SEQUENCE: 43

Met Pro Leu Leu Leu Leu Pro Leu Leu Trp Ala Gly Ala Leu Ala
1               5                   10                  15

Met Asp Asp Lys Thr His Thr Cys Pro Pro Cys Pro Ala Pro Val
            20                  25                  30

Ala Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
50                  55                  60

His Glu Asp Pro Glu Val Lys Phe Asn Trp Tyr Val Asp Gly Val Glu
65              70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Gly Leu Pro Ser Ser
        115                 120                 125

Ile Glu Lys Thr Ile Ser Lys Ala Lys Gly Gln Pro Arg Glu Pro Gln
    130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys Gly Thr Gly Gly Gly Ser Gly Gly Gly Gly Ser
                245                 250                 255

Gly Gly Gly Gly Ser Glu Asn Leu Tyr Phe Gln Gly Met Asp Thr Asp
            260                 265                 270

Leu Val Tyr Ile Glu Lys Ser Pro Asn Tyr Cys Glu Gly Asp Pro Val
        275                 280                 285

Thr Gly Ser Val Gly Thr Gln Gly Arg Ala Cys Asn Lys Thr Ala Pro
    290                 295                 300

Gln Ala Ser Gly Cys Asp Leu Met Cys Cys Gly Arg Gly Tyr Asn Thr
```

```
                305                 310                 315                 320

His Gln Tyr Ala Arg Val Trp Gln Cys Asn Cys Lys Phe His Trp Cys
                325                 330                 335

Cys Tyr Val Lys Cys Asn Thr Cys Ser Glu Arg Thr Glu Met Tyr Thr
                340                 345                 350

Cys Lys

<210> SEQ ID NO 44
<211> LENGTH: 358
<212> TYPE: PRT
<213> ORGANISM: Artificial Sequence
<220> FEATURE:
<223> OTHER INFORMATION: Fusion protein, IgG Kappa Leader, FC-domain,
      linker, Tev, 264-349

<400> SEQUENCE: 44

Met Glu Thr Asp Thr Leu Leu Leu Trp Val Leu Leu Leu Trp Val Pro
1               5                   10                  15

Gly Ser Thr Gly Asp Ala Asp Lys Thr His Thr Cys Pro Pro Cys Pro
                20                  25                  30

Ala Pro Pro Val Ala Gly Pro Ser Val Phe Leu Phe Pro Pro Lys Pro
                35                  40                  45

Lys Asp Thr Leu Met Ile Ser Arg Thr Pro Glu Val Thr Cys Val Val
            50                  55                  60

Val Asp Val Ser His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
                100                 105                 110

Asp Trp Leu Asn Gly Lys Glu Tyr Lys Cys Lys Val Ser Asn Lys Gly
            115                 120                 125

Leu Pro Ser Ser Ile Glu Lys Thr Ile Ser Lys Ala Lys Gly Gln Pro
            130                 135                 140

Arg Glu Pro Gln Val Tyr Thr Leu Pro Pro Ser Arg Glu Glu Met Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
                180                 185                 190

Lys Thr Thr Pro Pro Val Leu Asp Ser Asp Gly Ser Phe Phe Leu Tyr
            195                 200                 205

Ser Lys Leu Thr Val Asp Lys Ser Arg Trp Gln Gln Gly Asn Val Phe
210                 215                 220

Ser Cys Ser Val Met His Glu Ala Leu His Asn His Tyr Thr Gln Lys
225                 230                 235                 240

Ser Leu Ser Leu Ser Pro Gly Lys Gly Thr Gly Gly Gly Gly Ser Gly
                245                 250                 255

Gly Gly Ser Gly Gly Gly Ser Glu Asn Leu Tyr Phe Gln Gly
                260                 265                 270

Met Asp Thr Asp Leu Val Tyr Ile Glu Lys Ser Pro Asn Tyr Cys Glu
            275                 280                 285

Glu Asp Pro Val Thr Gly Ser Val Gly Thr Gln Gly Arg Ala Cys Asn
    290                 295                 300

Lys Thr Ala Pro Gln Ala Ser Gly Cys Asp Leu Met Cys Cys Gly Arg
```

```
                    305                 310                 315                 320
Gly Tyr Asn Thr His Gln Tyr Ala Arg Val Trp Gln Cys Asn Cys Lys
                325                 330                 335

Phe His Trp Cys Cys Tyr Val Lys Cys Asn Thr Cys Ser Glu Arg Thr
            340                 345                 350

Glu Met Tyr Thr Cys Lys
            355
```